United States Patent
Zhang et al.

(10) Patent No.: US 7,283,228 B2
(45) Date of Patent: Oct. 16, 2007

(54) PROCESS AND APPARATUS FOR SEGREGATION AND TESTING BY SPECTRAL ANALYSIS OF SOLID DEPOSITS DERIVED FROM LIQUID MIXTURES

(75) Inventors: Dongmao Zhang, West Lafayette, IN (US); Dor Ben-Amotz, West Lafayette, IN (US); Yong Xie, West Lafayette, IN (US); Vincent J. Davisson, West Lafayette, IN (US); Melissa Mrozek, Lafayette, IN (US); Corasi Ortiz, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 421 days.

(21) Appl. No.: 10/821,231

(22) Filed: Apr. 8, 2004

(65) Prior Publication Data

US 2005/0275837 A1    Dec. 15, 2005

Related U.S. Application Data

(60) Provisional application No. 60/554,701, filed on Mar. 19, 2004, provisional application No. 60/551,311, filed on Mar. 8, 2004, provisional application No. 60/490,057, filed on Jul. 25, 2003, provisional application No. 60/462,083, filed on Apr. 11, 2003, provisional application No. 60/462,472, filed on Apr. 11, 2003.

(51) Int. Cl.
*G01J 3/44* (2006.01)
*G01N 21/65* (2006.01)
*G01N 1/00* (2006.01)

(52) U.S. Cl. .................. 356/301; 356/36; 356/72; 356/244

(58) Field of Classification Search .................. 356/36, 356/38, 301, 244
See application file for complete search history.

(56) References Cited

U.S. PATENT DOCUMENTS

| | | | |
|---|---|---|---|
| 4,552,723 | A | 11/1985 | Adams et al. |
| 4,823,009 | A | 4/1989 | Biemann et al. |
| 5,334,837 | A | 8/1994 | Ikeda et al. |
| 5,605,838 | A | 2/1997 | Backhaus et al. |
| 5,772,964 | A | 6/1998 | Prevost et al. |
| 5,869,001 | A | 2/1999 | Backhaus et al. |
| 6,406,777 | B1 | 6/2002 | Boss et al. |
| 6,569,979 | B1 | 5/2003 | Strother et al. |
| 6,614,523 | B1 | 9/2003 | Boss et al. |

OTHER PUBLICATIONS

M. Schuerenberg, C. Luebbert, H. Eickhoff, M. Kalkum, H. Lehrach, E. Nordhoff, "Prestructured MALDI-MS Sample Supports," *Anal. Chem.* 72, (2000) 3436-3442.

*Primary Examiner*—F. L. Evans
(74) *Attorney, Agent, or Firm*—R. Neil Sudol; Henry D. Coleman; William J. Sapone

(57) ABSTRACT

Micro-droplets of liquid confining organic molecules of interest are dried on selected planar solvo-phobic substrates under conditions facilitating segregated precipitation of the larger, less soluable analytes toward edge portions of the deposit. Micro-spectrometer imaging using white light and FTIR false color can identify points of interest, and the same optics generally directed perpendicularly to the substrates selectively captures normal Raman spectra from selected points in the deposit. The spectra are manipulated using various data techniques to extract reliable information concerning analytes present at pico-Molar levels. The selected spots can also be subjected to FTIR spectroscopy followed by MALDI mass spectroscopy to obtain a variety of information from the identical specimen.

40 Claims, 33 Drawing Sheets

Fig. 5A
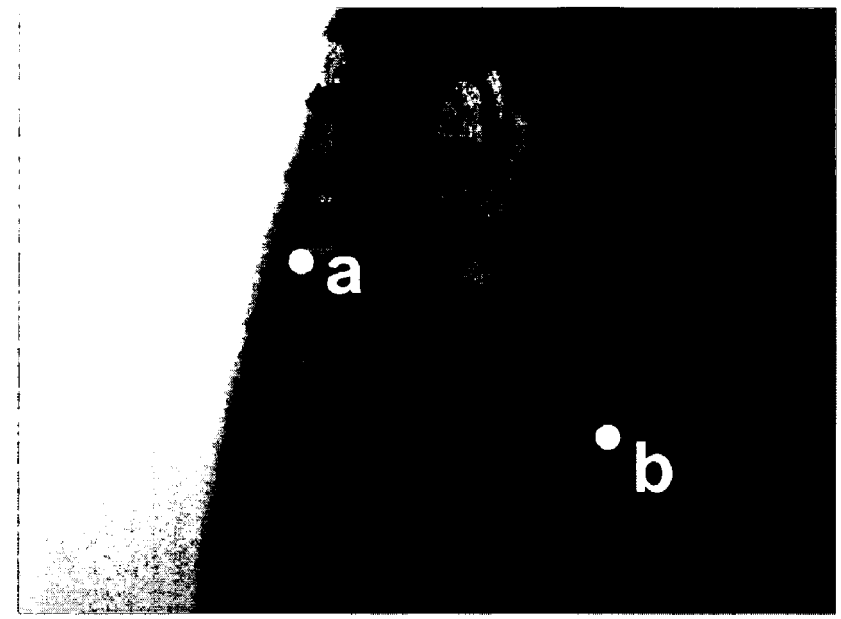
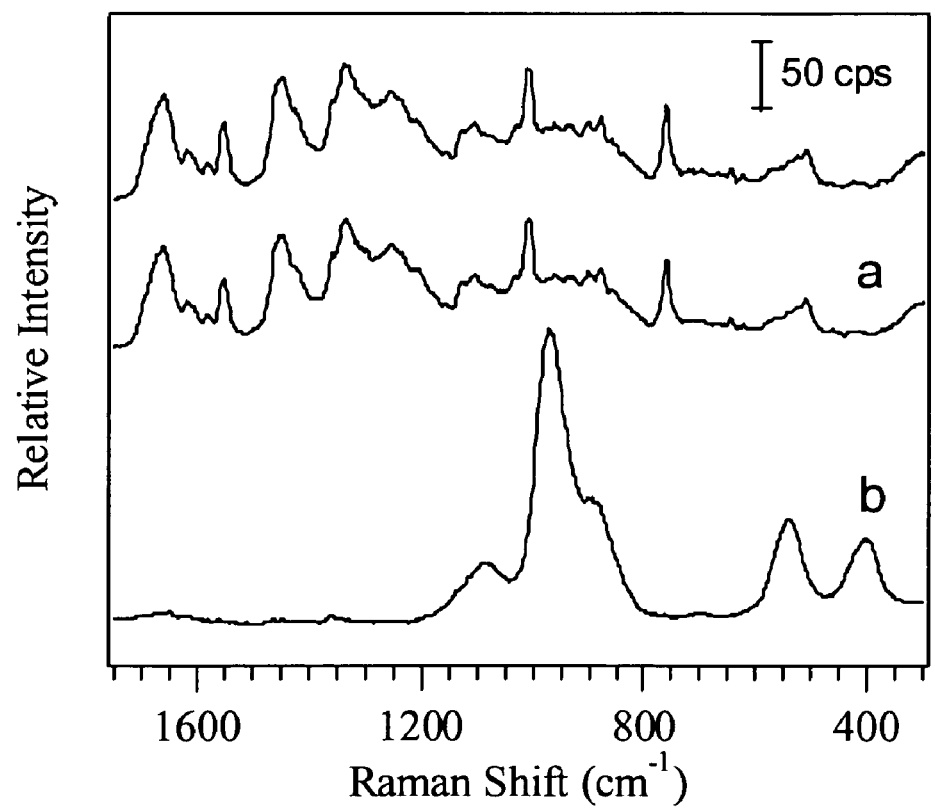
Fig. 5B

Fig. 6A
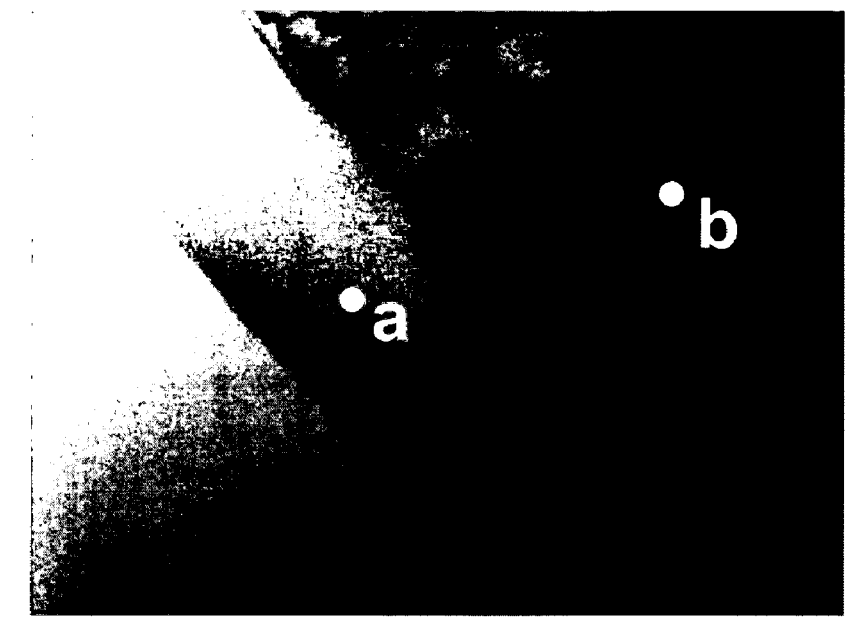
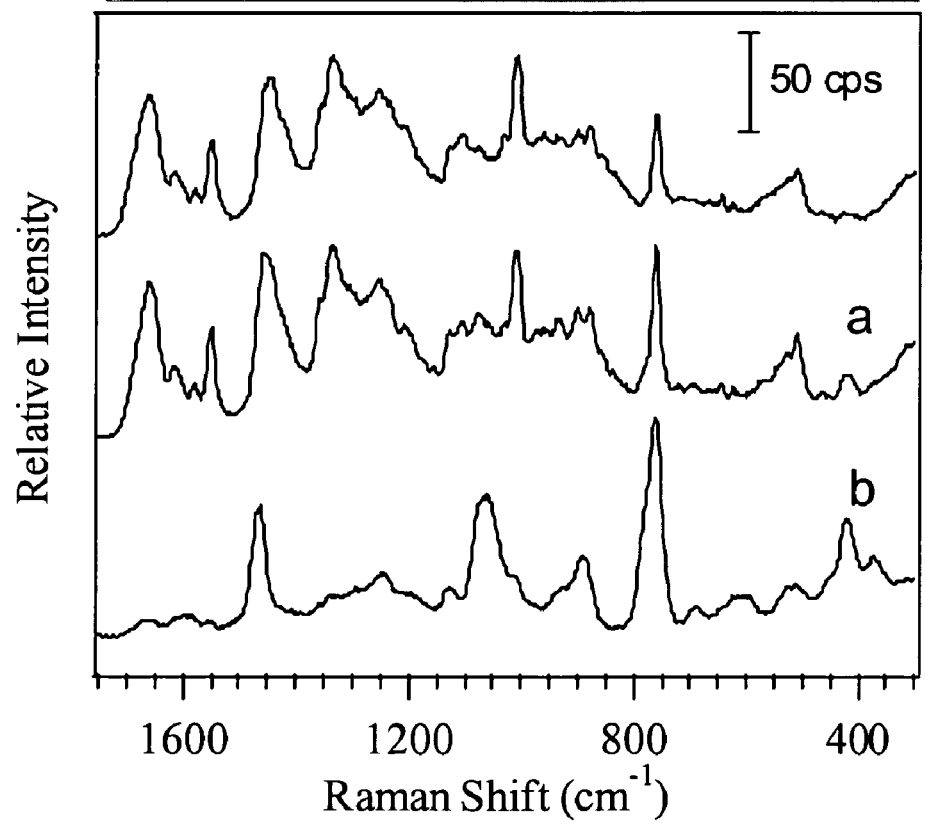
Fig. 6B

FIG. 11A

```
  1  MGSNKSKPKD  ASQRRRSLEP  AENVHGAGGG  AFPASQTPSK  PASADGHRGP  SAAFAPAAAE
 61  PKLFGGFNSS  DTVTSPQRAG  PLAGGVTTFV  ALYDYESRTE  TDLSFKKGER  LQIVNNTEGD
121  WWLAHSLSTG  QTGYIPSNYV  APSDSIQAEE  WYFGKITRRE  SERLLLNAEN  PRGTFLVRES
181  ETTKGAYCLS  VSDFDNAKGL  NVKHYKIRKL  DSGGFYITSR  TQFNSLQQLV  AYYSKHADGL
241  CHRLTTVCPT  SKPQTQGLAK  DAWEIPRESL  RLEVKLGQGC  FGEVWMGTWN  GTTRVAIKTL
301  KPGTMSPEAF  LQEAQVMKKL  RHEKLVQLYA  VVSEEPIYIV  TEYMSKGSLL  DFLKGETGKY
361  LRLPQLVDMA  AQIASGMAYV  ERMNYVHRDL  RAANILVGEN  LVCKVADFGL  ARLIEDNEYT
421  ARQGAKFPIK  WTAPEAALYG  RFTIKSDVWS  FGILLTELTT  KGRVPYPGMV  NREVLDQVER
481  GYRMPCPPEC  PESLHDLMCQ  CWRKEPEERP  TFEYLQAFLE  DYFTSTEPQY  QPGENL
```

FIG. 11B (1) Src Y-216[210-220]: LDSGGFYITSR

Src pY216[210-220]: LDSGGF(pY)ITSR (2) Src Y-419[413-422]: LIEDNEYTAR

Src pY419[413-422]: LIEDNE(pY)TAR (3) Src Y-530[505-536]: EPEERPTFEYLQAFLEDYFTSTEPQYQPGENL

Src pY-530[505-536]: EPEERPTFEYLQAFLEDYFTSTEPQ(pY)QPGENL (4) Src Y-530[524-536]: TSTEPQYQPGENL

Src pY-530[524-536]: TSTEPQ(pY)QPGENL

FIG. 26
A
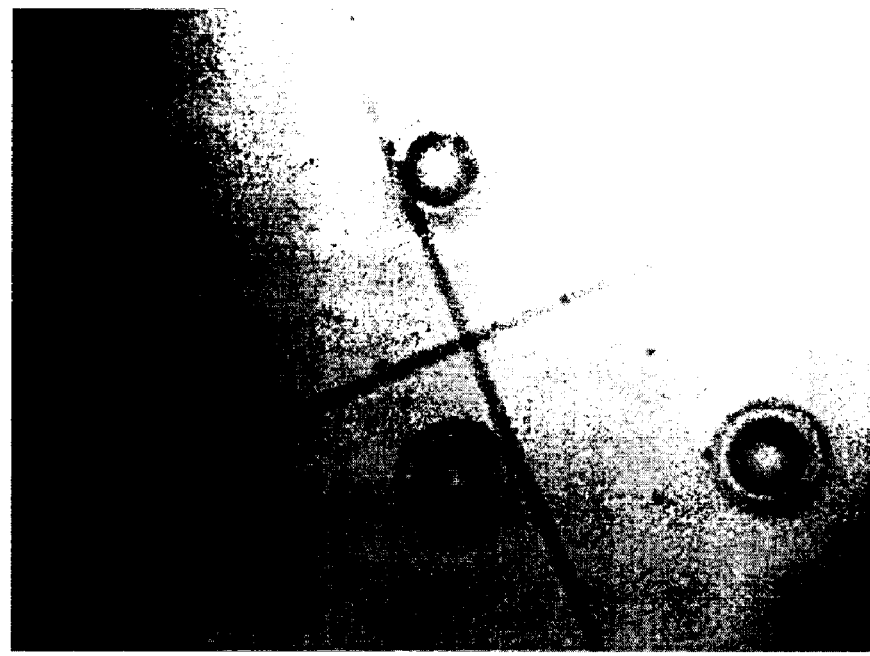
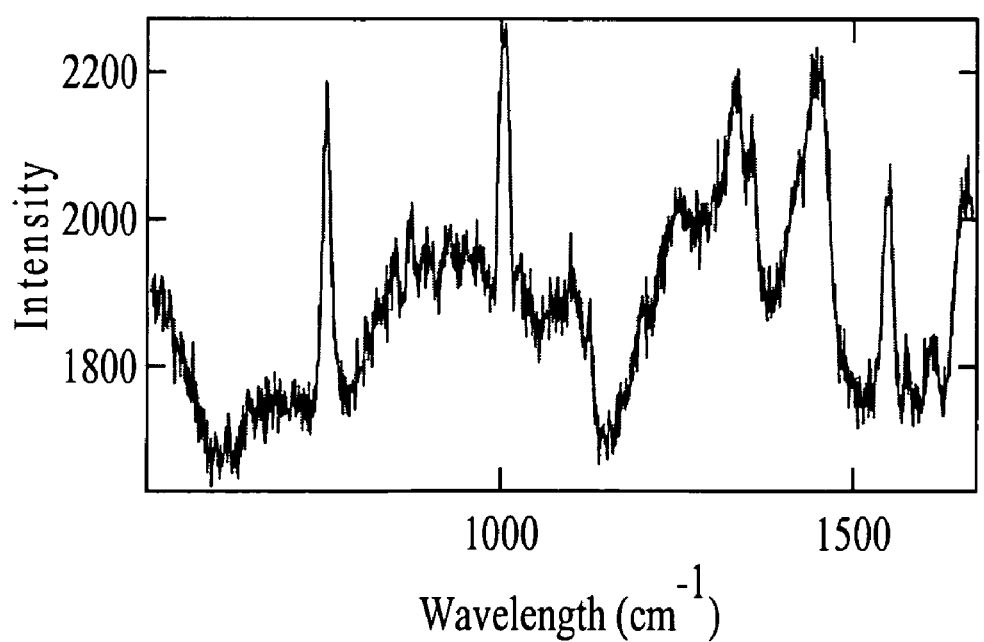
B

Fig. 28A
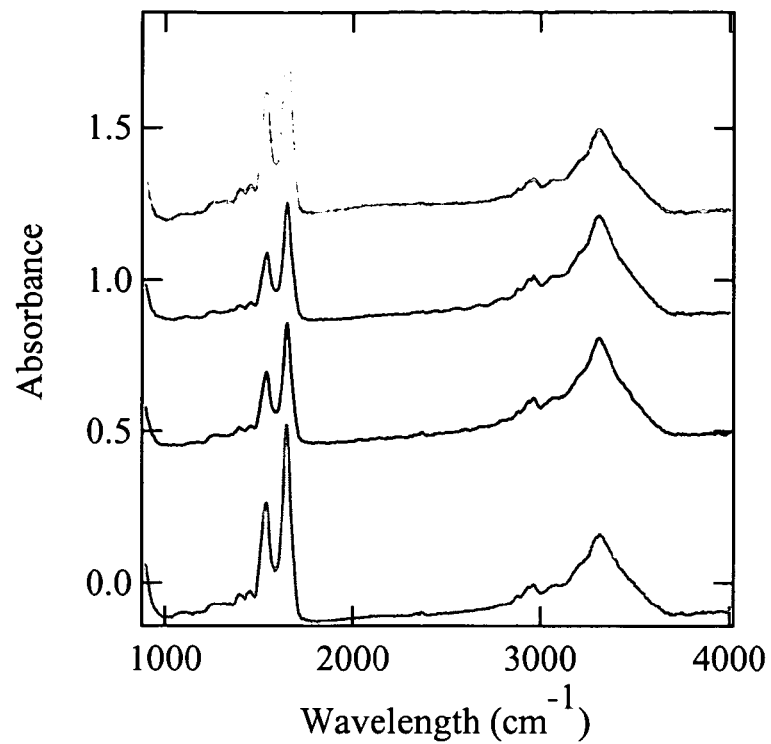
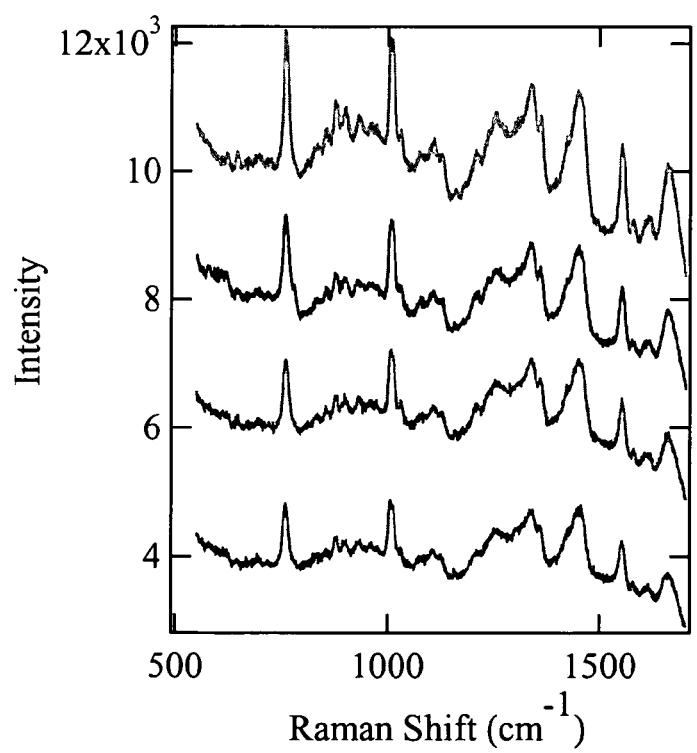
Fig. 28B

Fig. 29A
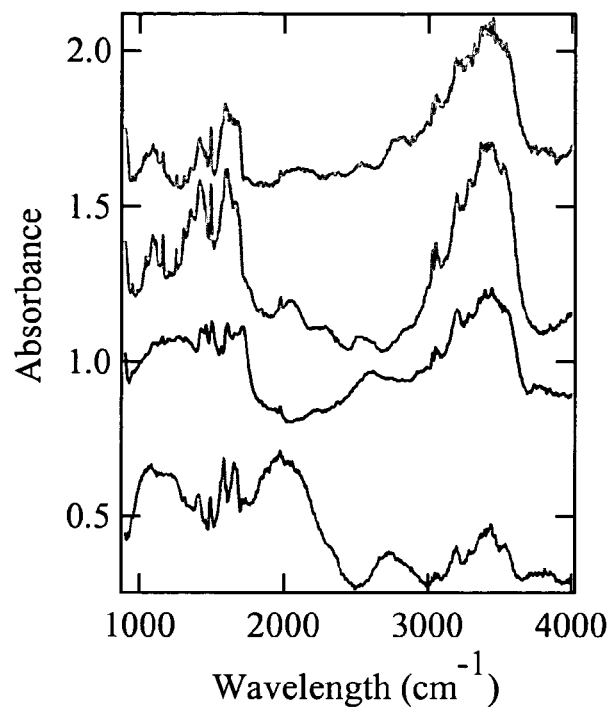
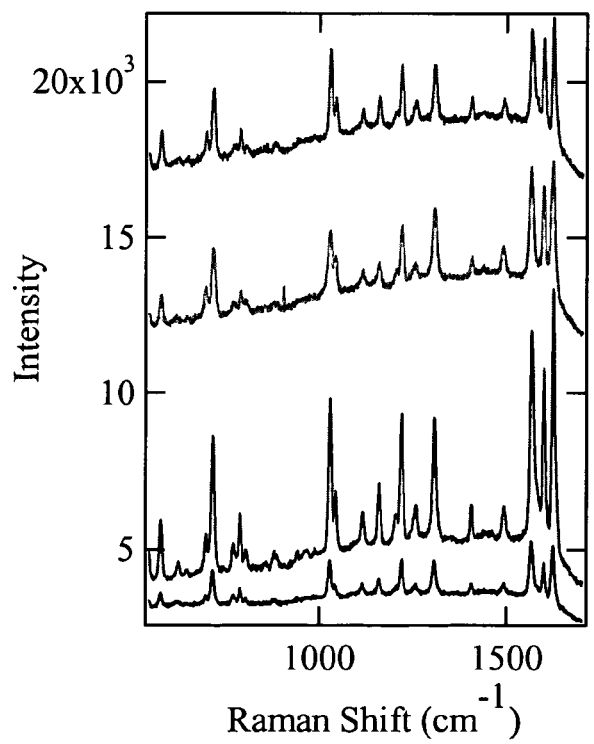
Fig. 29B

SEQUENCE LISTING

```
<160> NUMBER OF SEQ ID NOS: 1

<210> SEQ ID NO 1
<211> LENGTH: 536
<212> TYPE: PRT
<213> ORGANISM: Homo sapiens

<400> SEQUENCE: 1

Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30

Pro Ala Ser Gln Thr Pro Ser Lys Pro Ala Ser Ala Asp Gly His Arg
        35                  40                  45

Gly Pro Ser Ala Ala Phe Ala Pro Ala Ala Ala Glu Pro Lys Leu Phe
    50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
        115                 120                 125

Thr Gly Gln Thr Gly Tyr Ile Pro Ser Asn Tyr Val Ala Pro Ser Asp
    130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
    210                 215                 220
```

-continued

```
Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
                260                 265                 270

Glu Val Lys Leu Gly Gln Gly Cys Phe Gly Glu Val Trp Met Gly Thr
                275                 280                 285

Trp Asn Gly Thr Thr Arg Val Ala Ile Lys Thr Leu Lys Pro Gly Thr
                290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
                340                 345                 350

Leu Lys Gly Glu Thr Gly Lys Tyr Leu Arg Leu Pro Gln Leu Val Asp
                355                 360                 365

Met Ala Ala Gln Ile Ala Ser Gly Met Ala Tyr Val Glu Arg Met Asn
370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
                420                 425                 430

Ala Pro Glu Ala Ala Leu Tyr Gly Arg Phe Thr Ile Lys Ser Asp Val
                435                 440                 445

Trp Ser Phe Gly Ile Leu Leu Thr Glu Leu Thr Thr Lys Gly Arg Val
450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
                500                 505                 510

Glu Tyr Leu Gln Ala Phe Leu Glu Asp Tyr Phe Thr Ser Thr Glu Pro
                515                 520                 525

Gln Tyr Gln Pro Gly Glu Asn Leu
                530                 535
```

PROCESS AND APPARATUS FOR SEGREGATION AND TESTING BY SPECTRAL ANALYSIS OF SOLID DEPOSITS DERIVED FROM LIQUID MIXTURES

CROSS-REFERENCE TO RELATED APPLICATIONS

This application is based on and claims benefit to U.S. provisional application 60/462,083 and 60/462,472, both filed on Apr. 11, 2003, 60/490,057 filed Jul. 25, 2003, 60/554,701 filed Mar. 19, 2004, and 60/551,311 filed Mar. 8, 2004.

BACKGROUND

This invention pertains to the combined use of solid substrates, micro-deposition techniques, spectral imaging methods, and data processing to facilitate the concentration and separate detection of biological polymers, oligomers, and monomers including proteins, peptides, polysaccharides, glycans, nucleotides, and other analytes including smaller molecules, impurities and buffers, in a liquid mixture, using spectral analysis such as normal Raman spectroscopy, infrared spectroscopy and matrix-assisted laser desorption/ionization (MALDI) time-of-flight mass spectrometry. The term "normal Raman" is specifically adopted to distinguish the spectral imaging methods that are preferred for use in the present invention from surface-enhanced Raman spectroscopy (SERS).

Raman spectroscopy is increasingly being recognized as an important analytical tool, particularly in pharmaceutical, biomedical and biological applications, as a result of Raman's high chemical "fingerprint" information content. The vibrational spectral features present in normal Raman spectra collected from many organic molecules contain molecular "finger prints" that can be used to identify, distinguish and even quantify the molecules of different structure, conformation, branching or chemical modification. Likewise, infrared (IR) spectroscopy is a useful tool in the non-destructive analysis of materials including biological and other organic analytes. U.S. Pat. No. 5,334,837 to Ikeda et al. describes micro analytical methods and associated apparatus for detecting and quantifying organic compounds with very high sensitivity using IR spectroscopy in which drops of a liquid sample are deposited on a hydrophobic layer of from about 0.1 to 25 μm thickness located on an IR reflective or refractive surface of a sample holder that generally has a hydrophilic substrate, which can be stainless steel. Reduced suppression of absorption of infrared radiation by the hydrophobic layer is said to be achieved by reducing the thickness of the hydrophobic layer to between about 8 μm and 16 μm. Depressions or pin-holes of about 200 μm diameter spaced on 5 to 10 mm centers are provided that generally protrude through the hydrophobic layer to the hydrophilic substrate to act as condensing nuclei for the sample solution. A liquid sample solution placed in contact with a depression or hole is said to ball up while drying so as to leave a coherent concentrated dried sample in and/or adjacent to the depression or hole for subsequent examination. While there is a discussion of possible co-elution of specimen liquid to a mass analyzer for simultaneous testing, there is no provision for Raman analysis, nor is there any provision for mass spectral analysis of the identical sample. There is also no discussion of any intentional separation of the liquid sample constituents in the depression or hole of the sample holder.

Advantages of Raman relative to other vibrational spectroscopies, such as mid-IR and near-IR absorption or reflectance, include the relative insensitivity of Raman to water as well as Raman's compatibility with optical microscopy and CCD camera detection methods. However, since Raman scattering has a much lower cross-section than fluorescence, normal Raman spectral features can be easily obscured by even trace quantities of fluorescent impurities. Furthermore, Raman scattering from solvents containing buffering agents can overwhelm the normal Raman scattering from biological compounds that are present at much lower concentrations. The signal integration time for Raman is also generally greater than for some other vibrational spectroscopes. Although normal Raman spectroscopy has typically been restricted to high concentration condensed phase materials, that is liquids and solids, recent studies have demonstrated methods for obtaining high quality normal Raman spectra of biological compounds derived from increasingly lower concentration solutions. For example, a Raman system with enhanced collection efficiency has reportedly obtained normal Raman spectra from protein solutions with concentrations in the $10^{-4}$ M range. A liquid core waveguide has reportedly been used to measure normal Raman spectra of proteins in the $10^{-5}$ M concentration range with a total of about 10 nmol of protein probed using a 24 mW, 532 nm, excitation laser with an integration time of 3 minutes.

Various methods have previously been used to combat fluorescence background interference, none of which are universally applicable. Since fluorescence requires optical absorption, fluorescence can in some cases be effectively suppressed by using an excitation laser of either longer or shorter wavelength than the chromophore absorption band. Alternatively, fluorescence can be suppressed using time-resolved methods with gated or lock-in detection to distinguish Raman scattering from delayed fluorescence. A less sophisticated, but often quite effective, method for reducing fluorescence is photo-bleaching of the fluorescent compounds by prolonged exposure to the Raman excitation laser. In addition, fluorescence can be quenched by conductive solid substrates such as metals or graphitic materials. However, since efficient quenching requires direct contact with the conductive solid substrate, this method is only applicable to monolayer structures. Raman spectroscopy on such monolayer structures require either very high laser powers and cryogenic cooling, or electromagnetic and/or resonance enhancement of the monolayer Raman scattering, i.e. resonance Raman (RR) techniques.

Since Raman is a scattering rather than absorption process Raman testing can be performed on either optically transparent or opaque samples and substrates. Furthermore, no optical tagging or other chemical pre-processing of the sample is required, although additional benefit can in some cases be derived from the use of Raman tags. A large number of previous studies have described the use of RR and SERS to increase the Raman scattering cross section of various compounds, including biological materials. RR enhancement requires an analyte with a chromophore that absorbs at the wavelength of excitation, which for most proteins is in the UV. Furthermore, RR only enhances Raman features that are strongly coupled to the chromophore and thus can omit other important structural information. An additional limitation of RR is the optical damage induced by heating and/or photochemistry. SERS, on the other hand, can provide even larger enhancement than RR using suitable nano-structured metal substrates. Key limitations of SERS include the generation of spurious background signals, optical damage susceptibility and often poor reproducibility, both in terms of absolute intensity and spectral shape. It is also noteworthy that most SERS studies of biological compounds have been performed using mM analyte concentrations. These comments should not be taken to imply that RR and SERS are not tremendously powerful bio-molecule analysis methods that can provide valuable structural and kinetic information and unrivaled single-molecule sensitivity.

The most powerful current methods for proteomic diagnostics are those based on mass spectroscopy, particularly MALDI TOF MS, as these may be used to determine amino acid sequence, post-translational modification and even protein-protein interactions. High detection sensitivity combined with high sample throughput can be achieved with the use of a pre-structured sample support that confines each diagnostic specimen to a spot of less than 200 µm diameter. This sample geometry is achieved with stainless steel sample supports coated with a 30 to 50 µm thick polytetrafluoroethylene (PTFE) layer onto which an array of gold islands is deposited using a photolithographic mask. The islands, formed as 200 µm diameter round disks located at 2.25 mm spacing, act as hydrophilic sample anchors that hold liquid sample droplets in place during solvent evaporation. The water-repellent PTFE surface surrounding each island ensures that the droplets remain located on the gold islands so that, after evaporation, uniform specimens of known geometry are located at predetermined positions on the support (Bruker Anchorchip). However, accurate quantification remains a significant challenge and ambiguities can exist in the analysis of biological and organic analytes of different structure but equal mass. Thus the sensitivity of normal Raman spectroscopy to differences in conformation, branching and binding can be useful to compliment mass spectroscopy by providing a valuable additional dimension of chemical structure information. Furthermore, normal Raman can in some cases lead to a stand-alone detection, identification and/or quantification method for proteomic analysis.

Thus, there remains a need for a method for separating and detecting the presence of analytes, particularly proteomic analytes, at very low concentrations in liquid specimens containing much larger concentrations of other molecules of potentially masking character. There remains a further need for non-destructive testing procedures for selected analytes that can be repeatedly performed on any given specimen, preferably using multiple techniques to accumulate a library of information on a given sample. There also remains a need for very simply eliminating fluorescence interference from the normal Raman spectra of impure solids, for example, biological amino acids and proteins. There is also a need for a sample support that can be used in IR spectroscopy, Raman spectroscopy and MALDI mass spectroscopy that exhibits low optical absorbance, high optical reflectance, little or no interfering background signals, and, a non-wetting interaction with the analyte solution, i.e., low solvent affinity, and that is useful with a range of solvents. There is a further need for methods of handling extremely small volumes of sample liquids containing analytes at very small concentration.

SUMMARY OF THE INVENTION

The analyte segregation and testing method of the present invention starts with the formation of a suitable sample support. The sample support used in the analyte segregation method of the present invention must be compatible with the measurement of normal Raman scattering spectra in the sense that they produce minimal interfering background signals such as luminescence and/or Raman scattering from the substrate alone. Further, these same performance characteristics for the sample support also allow its use as a sample holder for a common specimen to be tested by normal Raman, IR spectroscopy, and MALDI. The sample supports are generally formed to include a substantially planar substrate, which can be either reflective or transmissive of the range of spectra of interest. In a preferred embodiment, a reflective planar substrate includes a metallic surface on the substrate having a roughness of less than about one-tenth the wavelength of the radiation to be applied to specimens. Suitable substrates include nominally flat gold foil or gold coated glass, and planar polished stainless steel. Other metals that can be used include silver, platinum, titanium, aluminum, and alloys of these and other metals. Transmissive substrates may include inorganic materials, for example, quartz, germanium, gallium arsenide, or zinc sulfide, and polymeric materials such as polyethylene, polypropylene, polycarbonate, polyacrylate, polymethacrylate, polyethyleneterephthalate, and polystyrene.

Except possibly in the case of a naturally solvophobic metal, a solvophobic enhancement layer, having a thickness of less than about 100 nm and preferably having a thickness of less than about one-quarter the wavelength of the radiation of interest, is added to cover the substrate surface to inhibit spreading of a specimen liquid to an undesirable extent. The solvophobic enhancement layer can be formed, for example, from a fluorinated polymer, a fluorinated hydrocarbon, or a thiol derivative of a hydrocarbon. A self-assembled organic monolayer (SAM) particularly suitable for use on gold can be formed from alkyl chains with terminal thiol groups that bind to the gold surface. While SAMs are generally not as stable or robust as polymeric coatings, the solvo-phobic character of the alkyl chains can be manipulated by suitable selection of organic residues. The coated substrate sample supports have an advantage of also being solvo-phobic to many polar solvents, thus limiting or controlling the spread of a deposited drop.

The analyte segregation can be achieved in the present method by depositing droplets of an analyte solution, which can include buffers and contaminants, on a selected sample support and then drying each droplet in such a way that the analyte and other compounds accumulate in physically separated regions. The deposit of the micro-droplet can be performed by manual micropipette depositions of 1-10 µl solution volumes to produce sample spots of 0.5-5 mm diameter. However even smaller volumes can be deposited using ink-jet micro-printing, for example of 8 nl solution volumes to produce spots of 15 µm diameter containing less than 25 fmol of an organic analyte of interest. Standardization of the procedure and apparatus can be accomplished using a micro-droplet from a known standard solution of a given molecule. Sources for the micro-droplet can include any of an array of chromatographic fractions derived from any separation method such as, for example, high pressure liquid chromatography, capillary electrophoresis, reverse phase high pressure liquid chromatography, with or without pre- or post-separation or digestion of proteins to peptides, when proteins are the analyte in the sample.

Following the deposit of the micro-droplet on the selected sample support, the solvent can be evaporated from the micro-droplet under conditions that promote accumulation of the target analyte and the buffer or other compounds as spatially separated precipitates. It has been observed that deposits of biological polymers and oligomers including proteins, peptides, nucleotides, and other less soluble molecular analytes from a drop of liquid placed on a non-wetting substrate often accumulate in a circular ring formed during the evaporation process. This ring forming effect, sometimes referred to as the "coffee-ring" effect, localizes the deposited analyte and thus facilitates additional detection. Generally, the larger, less soluble components tend to precipitate near the edges of the deposit, while buffers and other more soluble compounds are distributed throughout the deposit region and more concentrated toward a central portion of the deposit. This analyte segregation method can also be used advantageously to segregate different analyte components in a mixture, such as compounds of different chemical composition and/or structure and thus facilitate the analysis of each separate component. The evaporation conditions required for optimal segregation can include temperature and other parameters that influence evaporation rate, such as the control of vapor phase convection of the solvent during the evaporation process. While the efficiency of this segregation process can in general depend on a number of variables, the process is generally applicable to biological compounds when using one of the previously identified substrates and evaporating in ambient or desiccated air at normal room temperature. This method can also be applied at other lower or higher temperatures under various atmospheric conditions. Potential advantages of various conditions include higher evaporation speed (such as at higher temperature) or improved segregation of different components (such as in higher solvent vapor pressure atmosphere). In some applications, high temperatures that might lead to degradation or denaturation of the biological compounds are to be avoided. This physical separation can be achieved by depositing a micro-droplet of solution, typically between 10 nl and 10 μl on a selected substrate. The total time required for deposition and solvent evaporation at normal room temperature is typically about 10 minutes for μl depositions and only about 1 minute for nl depositions, which is roughly comparable to the time required for normal Raman signal collection.

After solvent evaporation, collection of normal Raman spectra from the segregated analyte deposits can be achieved using an epi-illuminated micro-spectrometer focused on a selected small portion of the deposit ranging between about 1 μm to about 100 μm in diameter. Spectral imaging methods can be used to locate and measure the normal Raman spectra from regions containing the analyte of interest. Pre-scans using IR spectroscopy can be used to identify regions of particular interest. High quality normal Raman spectral data can be collected of proteins derived from concentrations down to about 0.1 μM and protein surface densities down to about 1 pg per square μm of surface area using a 12 mW, 633 nm, HeNe laser with integration times ranging from about 5 seconds to about 500 seconds. This lower limit of surface density corresponds to about 0.1 fmol per square μm of surface area for a protein of 10,000 g/mol molecular weight. Lasers of other wavelengths and of other power can be used, in either continuous or pulsed mode, as long as the total energy delivered to the deposited analyte is insufficient to produce damage to the deposited analyte. Continuous lasers delivering up to 100 mW per square μm of surface area can generally be used without producing optical damage to proteins. Lasers having power greater than 1 Watt may be used when employing substrates and wavelengths selected to have very low substrate optical absorption and thus low optically induced heating. The spectral data can be collected using a portion of the laser delivery optics.

The spectral data can then analyzed using a variety of numerical techniques intended to enhance the ability to detect a given molecule of interest. One technique involves using a Savistky-Golay second derivative algorithm to supress both broadband background and pixel noise while retaining the desired Raman spectral features. Another technique involves normalizing the output of the second derivative algorithim in order to suppress intensity variations that can occur due to drifts in laser power or optical alignment, changes in the number of analyte molecules within the optical collection region, or other effects unrelated to analyte chemistry. Another technique involves classifying the previously processed spectra with a partial least square discriminant program to cluster specimens having common contents together. Yet another technique involves plotting the pseudo probabilities of various classified spectra belonging to a given group, which again clusters specimens having common characteristics together. Still another technique involves subtracting the normalized spectral outputs of two specimens to detect any spectral differences indicating differences in the specimen contents.

A key advantageous feature of the analyte segregation method of the present invention is that the method facilitates the concentration or agglomeration of analytes of interest in essentially pure solid form at surface densities compatible with normal Raman detection and IR spectroscopy without any interference from buffer or other compounds that may be originally present in a deposited micro-drop in a 100-fold or greater excess thus facilitating the measurement of normal Raman and other spectra. The entire deposition and spectral data collection process can be performed in only a few minutes. This method can also be used to very effectively remove fluorescence, buffer and other contaminant introduced interferences from normal Raman spectra. The procedure can be used to segregate and identify proteins and other organic polymers and oligomers dispersed at μM concentration levels in liquids that also contain inorganic or organic buffer compounds and other contaminants at mM concentration.

The analyte segregation method of the present invention that facilitates the concentration or agglomeration of biological polymers such as proteins, peptides, and other molecules of interest can be used with a variety of spectral detection procedures including, for example, THz spectroscopy; far infrared spectroscopy; infrared spectroscopy; normal Raman spectroscopy, resonance Raman spectroscopy; visible spectroscopy; reflectance spectroscopy and microscopy; transmittance spectroscopy; ultraviolet spectroscopy; far ultraviolet or vacuum ultraviolet spectroscopy; x-ray spectroscopy; optical rotatory dispersion; circular dichroism including ultraviolet, visible and infrared; fluorescence and phosphorescence spectroscopy; atomic adsorption; magnetic resonance including nuclear magnetic resonance, electron paramagnetic resonance, electron spin resonance; and mass spectrometry, including variations of ionization methods such as electron impact, chemical ionisation, matrix assisted laser desorption ionization, and detection methods, including sector detection, quadrupole detection, ion-trap, time-of-flight, and Fourier transform.

Additional features and advantages of the present invention will become apparent to those skilled in the art from a consideration of the following discussion of preferred embodiments and examples, which reference the accompanying drawings.

BRIEF DESCRIPTION OF THE DRAWINGS

FIG. 5A is a white light optical image of a region near the edge of an about 4 mm diameter circular deposit of a 10 µL volume of solution containing 10 µM lysozyme and 1 mM PBS on a 50 nm PTFE on stainless steel sample support.

FIG. 5B shows the corresponding Raman spectra (a) and (b) taken from regions a and b, respectively, shown in FIG. 5A. The top spectrum in FIG. 5B is the Raman spectrum a similarly deposited sample of a solution of 10 µM lysozyme without any buffer. All spectral acquisition times were 60 seconds.

FIG. 6A is a white light optical image of a region near the edge of an about 4 mm diameter circular deposit of a 10 µL volume of solution containing 10 µM lysozyme and 1 mM Tris-HCl buffer on a 50 nm PTFE on stainless steel sample support.

FIG. 6B shows the corresponding Raman spectra (a) and (b) taken from regions a and b, respectively, shown in FIG. 6A. The top spectrum in FIG. 6B is the same as the top spectrum in FIG. 5B.

FIG. 11A shows the amino acid sequence of proto-oncogene tyrosine-protein kinase Src (EC 2.7.1.112) (p60-src) (c-src), P12931 from NCBI (National Center for Biotechnology Information) website. The sequence is 536 amino acids long.

FIG. 11B shows the amino acid sequences of four peptides. The numbers after Y denotes the Tyr phosphorylation site, while the numbers in square brackets denote the location of the sequence in the p60-src protein. The first three peptides Y-216, Y-419 and Y-530[505-536] are the same as those produces by tryptic digestion of the human p60-src protein. Note that corresponding tyrosine sites in proteins homologous to the chicken p60-src protein are Y-213, Y-416 and Y-527.

FIG. 26A is a white light image of several ring deposits from a 96×96 drop array formed by micro-printing.

FIG. 26B is a normal Raman shift spectrum of lysozyme taken from one of the ring deposits shown in FIG. 26A.

FIG. 28 shows four FTIR absorbance spectra and four Raman shift spectra of lysozyme taken from the same four points within the "hot spot" identified in FIG. 27B.

FIG. 29 shows spectra derived in a manner similar to that of FIG. 28 from a different specimen of carbamazepine.

DESCRIPTION OF PREFERRED EMBODIMENTS

Figure 33:
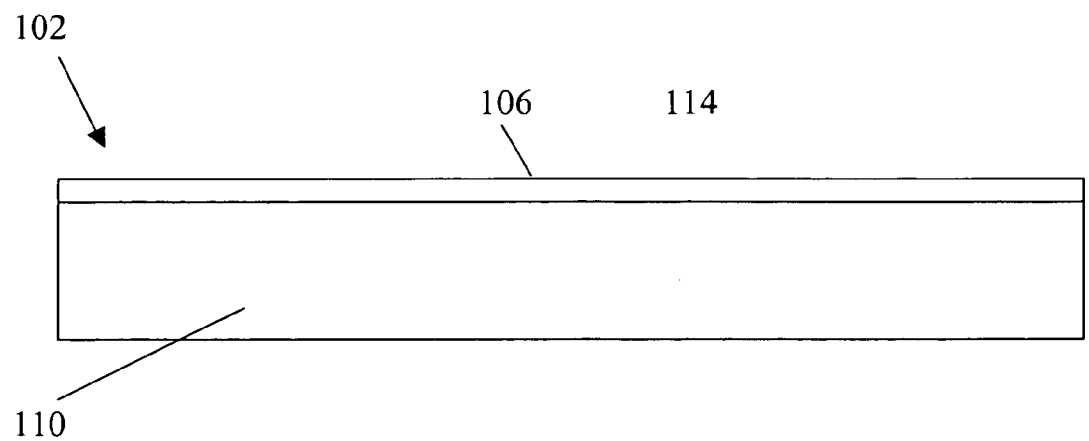
FIG. 33 is a schematic side elevational view of a molecular sample support in accordance with the present invention.
Figure 34:
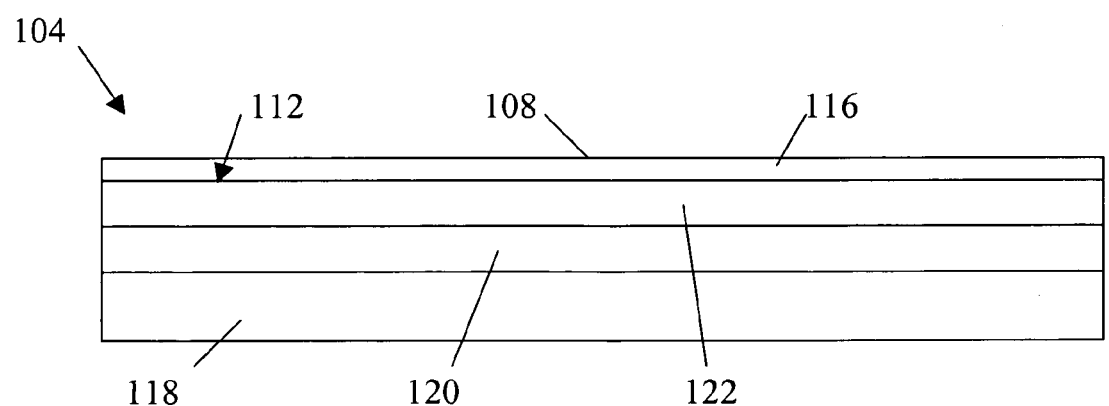
FIG. 34 is a schematic side elevational view of another molecular sample support in accordance with the present invention.

The analyte segregation and testing methods of the present invention generally requires a substantially planar solvophobic sample support 102 (FIG. 33) or 104 (FIG. 34) having an optically smooth surface 106, 108 desirably producing minimal interfering background signals such as luminescence and/or Raman scattering from the sample support alone. The sample supports 102, 104 are selected for their ability to diminish or restrict spreading of the sample and, preferably, to increase by surface tension the contact angle between the solvent of the sample and the surface. The sample supports 102, 104 generally comprise a substrate 110, 112 covered by a solvophobic enhancement layer 114, 116. Suitable substrates 110 (FIG. 33) can include nominally flat metals such as gold, silver, platinum, titanium, aluminum, and alloys of these and other metals. The methods of the present invention can be practiced with substrates 110 consisting essentially of gold, which can be in the form of merely gold foil of about 0.1 mm thickness, or substrates 112 including a glass layer 118 coated with a layer 120 of about 10-100 nm of chromium and over coated with a layer 122 of about 10-100 nm of gold. The glass portion 118 of the substrate 112 can comprise a glass slide or cover slip, which. exhibits a flat surface. A preferred sample support 102 can be constructed from a substrate 110 having a gold surface, such as previously described, further modified with a self-assembled organic monolayer forming the solvophobic enhancement layer 114. A self-assembled organic monolayer 114 particularly suitable for use on gold can be formed from alkyl chains with terminal thiol groups that bind to the gold surface. The solvophobic character of the alkyl chains can be manipulated by suitable selection of organic residues. A further preferred substrate 110 is stainless steel coated with an about 50 nm layer of PTFE forming the solvophobic enhancement layer 114. The PTFE layer can be applied by spin coating at least one layer of a diluted PTFE resin material on the surface of the low background substrate. For example, a sample support having a solvophobic layer of less than about 50 microns can be made by spin coating a Teflon®. AF solution (Grade 400S1-100-1), available from DuPont (Wilmington, Del.) diluted with Fluorient FC-40, available from 3M Company (Minneapolis, Minn.) onto a gold layer that had been vacuum coated onto a glass support. The PTFE layer can be applied to a variety of substrates including optically transmissive as well as optically reflective surfaces.

The analyte segregation can be achieved in the present method by depositing droplets of an analyte solution, typically between about 10 pL and 10 µL, which can be an analyte-buffer mixture, on a selected sample support. A preferred source of the micro-droplet includes a direct output from any chromatographic separation apparatus, for example, high pressure liquid chromatography, capillary electrophoresis, reverse phase high pressure liquid chromatography. Deposition can be performed manually, or by using various automated micro-deposition or micro-printing techniques including methods generally known as piezoelectric "ink-jet" techniques. The later techniques permit more than one droplet to be placed on the sample support at the same precise location, generally spaced by sufficient time to permit drying of each droplet before addition of a subsequent droplet, thus enabling increased analyte density at a given droplet location.

Following the deposit of the droplet on the selected sample support, the solvent can be evaporated from the micro-droplet under conditions that promote accumulation of the analyte and buffer or other compounds as spatially separated precipitates that accumulate in physically separated regions of the solid sample support. The evaporation conditions for optimal segregation can be regulated by control of the immediate environment of the deposit region including temperature, solvent vapor pressure, convection rates and other parameters. The evaporative process generally can be terminated when the specimen is visibly dry even though the specimen may retain some small portion of the largely evaporated solvent. Even prolonged evaporative conditions at low to moderate temperatures appear to have little further effect on most proteins, peptides and other larger bio-molecules.

After solvent evaporation, collection of normal Raman and other spectra from the segregated analyte deposits can be achieved by focusing on an appropriate portion of the remaining deposit. It may be beneficial in some circumstances to initially scan the deposit using visible or IR wavelength to identify regions within the deposit of particular interest. Normal Raman spectra can be collected using an epi-illuminated micro-spectrometer using a 12 mW, 633 nm, HeNe laser with integration times ranging from about 5 seconds to about 500 seconds. The laser is focused on a selected small portion of the deposit ranging between about 1 µm to about 100 µm in diameter with the laser beam arranged substantially perpendicularly to the substrate. The spectral data is preferably collected from reflective sample supports using a portion of the laser delivery optics. Other spectra, for example, infrared and visible spectroscopy, can also be collected from the regions containing the analyte of interest, generally using other radiation sources and other collection optics, preferably connected to at least part of the same objective lens system to ensure identity of the sample target.

The spectral data can then analyzed using a number of numerical techniques intended to enhance the ability to detect a given molecule of interest. The specific methods of the present invention including the numerical techniques are disclosed in the following examples:

EXAMPLE SET A

Figure 1:
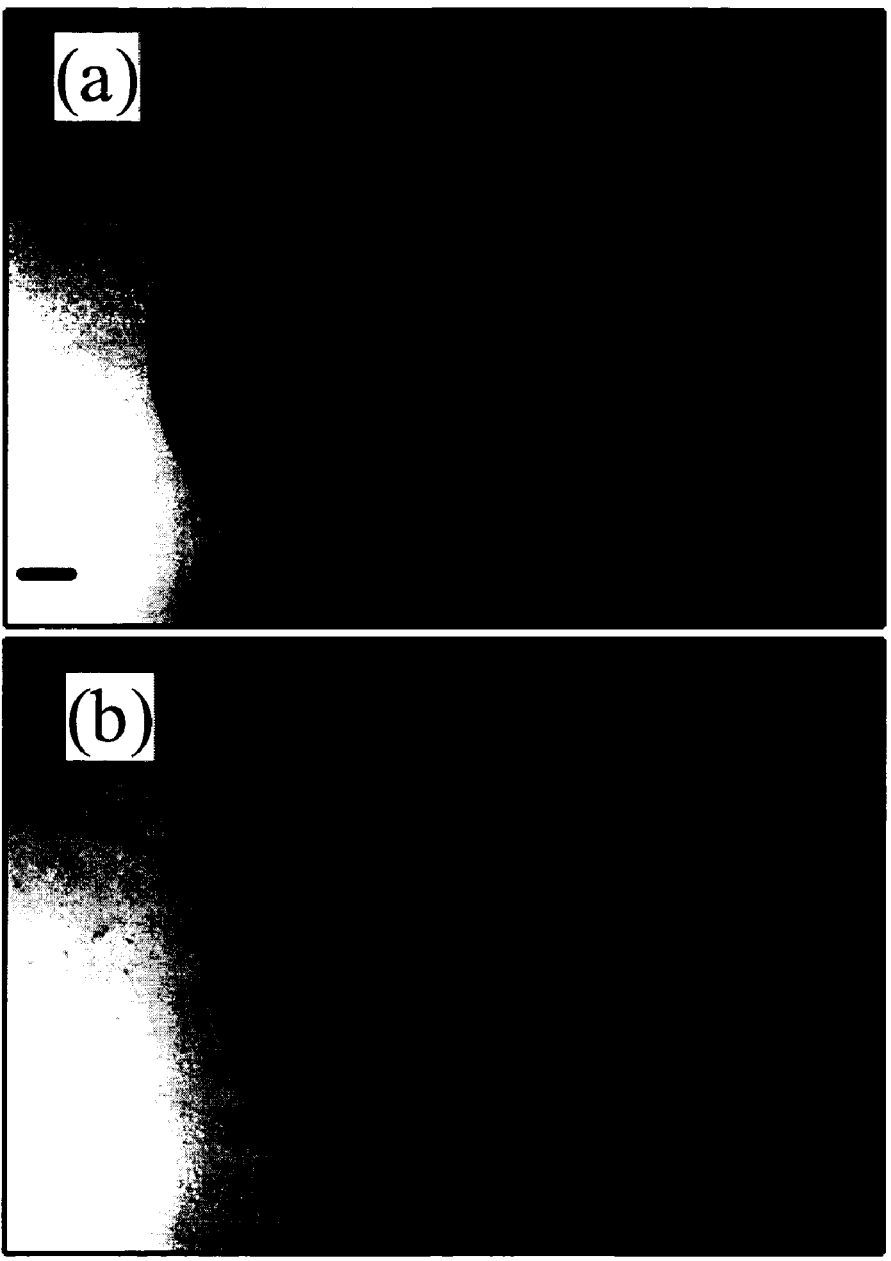
FIGS. 1(a) and 1(b) are white light images of O-phospho-L-serine (a) and myoglobin (b) on a sample support of polished stainless steel coated with 50 nm of PTFE after solvent evaporation. The deposition volume for both samples is 4 µl. The concentrations of the deposited solutions are 10 mM for O-phospho-L-serine and 60 µM myoglobin. The bar in image (a) is 50 µm long and both images have the same magnification.

For the first example of the methods of the present invention that also demonstrates a significant reduction in undesirable fluorescence background, O-phospho-L-serine (Cat. No. P-0878, Lot 21K1389, Purity of 99%), myoglobin (Cat. No. M-0630, Lot 110K7034, Purity of 95-100%) and lysozyme (From chicken egg white) were obtained from Sigma. Synthetic human insulin (Humulin®) was provided by Eli Lilly & Co. High purity water (18.2 MΩcm$^{-1}$) generated with MilliQ plus system (Millipore) was used to prepare a saturated O-phospho-L-serine (~10 mM) and 60 µM myoglobin solution. 4 µL droplets of saturated O-phospho-L-serine and 60 µM myoglobin are deposited and dried on a substrate of polished stainless steel coated with 50 nm of PTFE. FIG. 1 shows the morphologies of the O-phospho-L-serine (a) and myoglobin (b) on the sample support after solvent evaporation. Both images are of the same size, the bar in image (a) represents 50 µm. Although the deposited volume is the same for both samples (4 µl), the spot size of myoglobin after solvent evaporation is about 3 times larger in diameter than that of O-phospho-L-serine. The spot size appears to be dependent on factors other than merely the characteristics of the solvent and sample support surface as might be expected.

Figure 2:
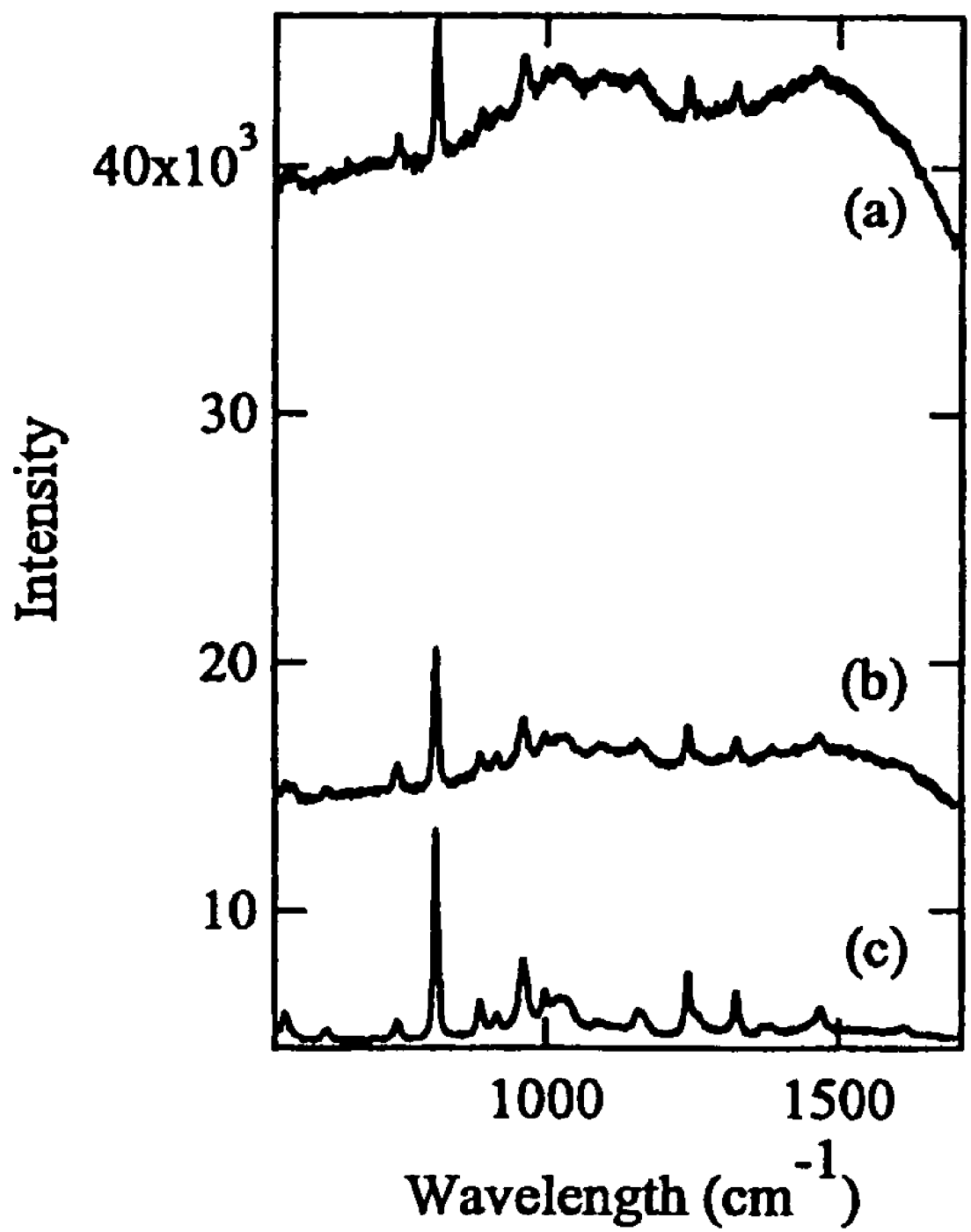
FIG. 2 is a graphical presentation of the Raman spectra obtained from O-phospho-L-serine. Spectra (a) and (b) were obtained from a powder specimen while spectrum (c) was from a solution deposited according to the present invention. Spectra (a) and (b) were obtained after 7 minutes and 65 minutes of laser pre-illumination, respectively, while spectrum (c) was obtained with no pre-illumination. A laser power of 12 mW (at the sample) and an integration time of 10 seconds were used to collect each spectrum.

FIG. 2 compares the fluorescence background reduction results obtained from an O-phospho-L-serine sample using either the photobleaching technique with the results obtained from the isolation of a sample on a 50 nm PTFE on stainless steel sample support. Spectra (a) and (b) were collected from the solid powder subsequent to photobleaching (using the Raman excitation laser) for 7 min and 65 min, respectively. Spectrum (c) was obtained from a crystal formed on the substrate without prior laser illumination. All of the spectra were obtained using a 20× objective and an integration time of 10 seconds.

Figure 3:
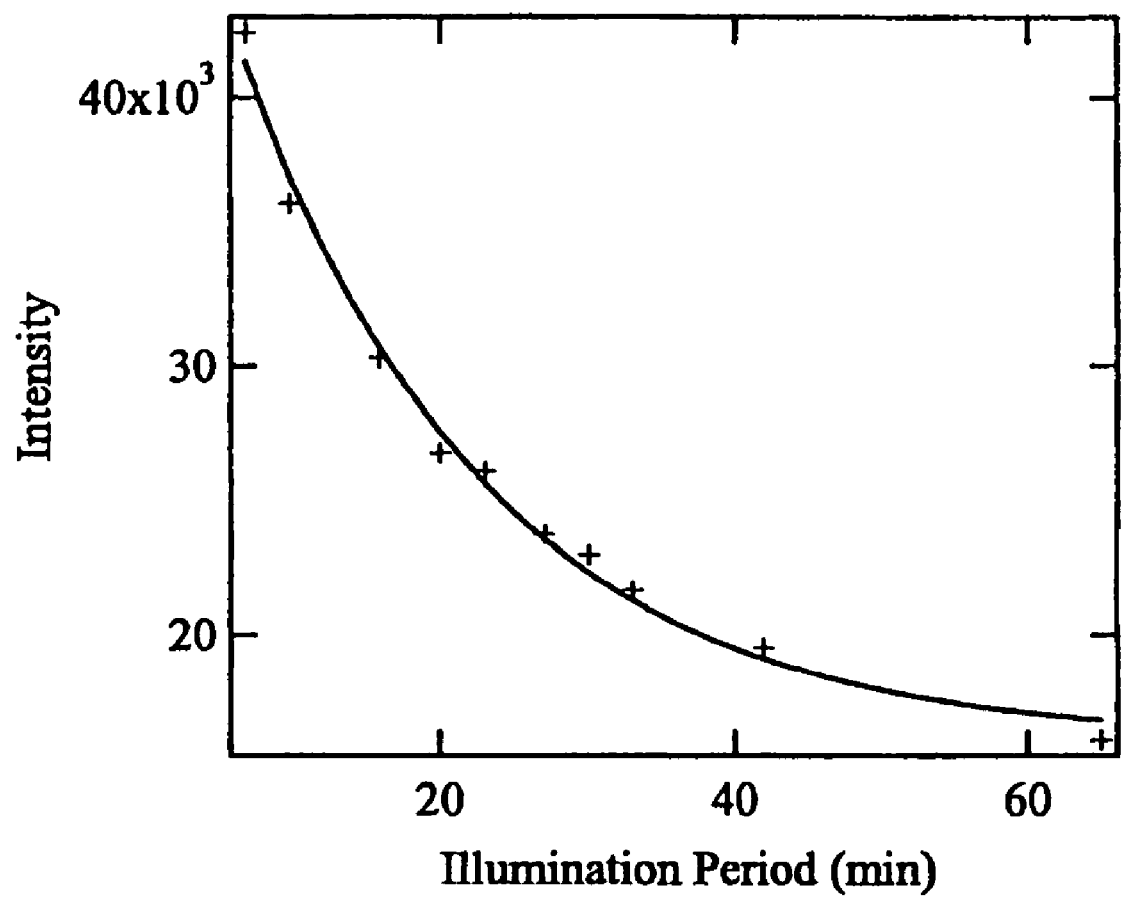
FIG. 3 is a graph of the spectral intensities at 1300 cm$^{-1}$ in the series of Raman spectra of O-phospho-L-serine powder, after photobleaching for different illumination periods. The experimental data points are fit to an exponential curve.

A series of photobleaching spectra collected after different periods of laser illumination indicate that partial photobleaching takes place with an exponential 1/e time constant of about 17 minutes under the stated experimental conditions. FIG. 3 shows the signal intensity at 1300 cm$^{-1}$ of the series of spectra each obtained with an integration time of 10 seconds, after different periods of continuous laser illumination as indicated on the horizontal axis. The exponential fit curve shown in FIG. 3, $I(t)=16016+38631e^{-0.06t}$, indicates that photobleaching can only reduce the background to about 16,000 counts after prolonged laser exposure, while the method of the present invention produced an initial background of only about 5,000 counts. Thus, the deposition and resulting analyte segregation according to the present invention reduced the initial fluorescence background by more than a factor of 10 (from over 50,000 counts to 5,000 counts). The small residual background remaining in the inventive deposit is relatively insignificant since the background intensity is smaller than that of the analyte Raman features. This residual background is not due to the substrate, which produces a background of less than 100 counts. Since the residual background can be further decreased by photobleaching, the background appears to be due to a small amount of fluorescence contamination remaining in the region of the amino acid deposit.

Figure 4:
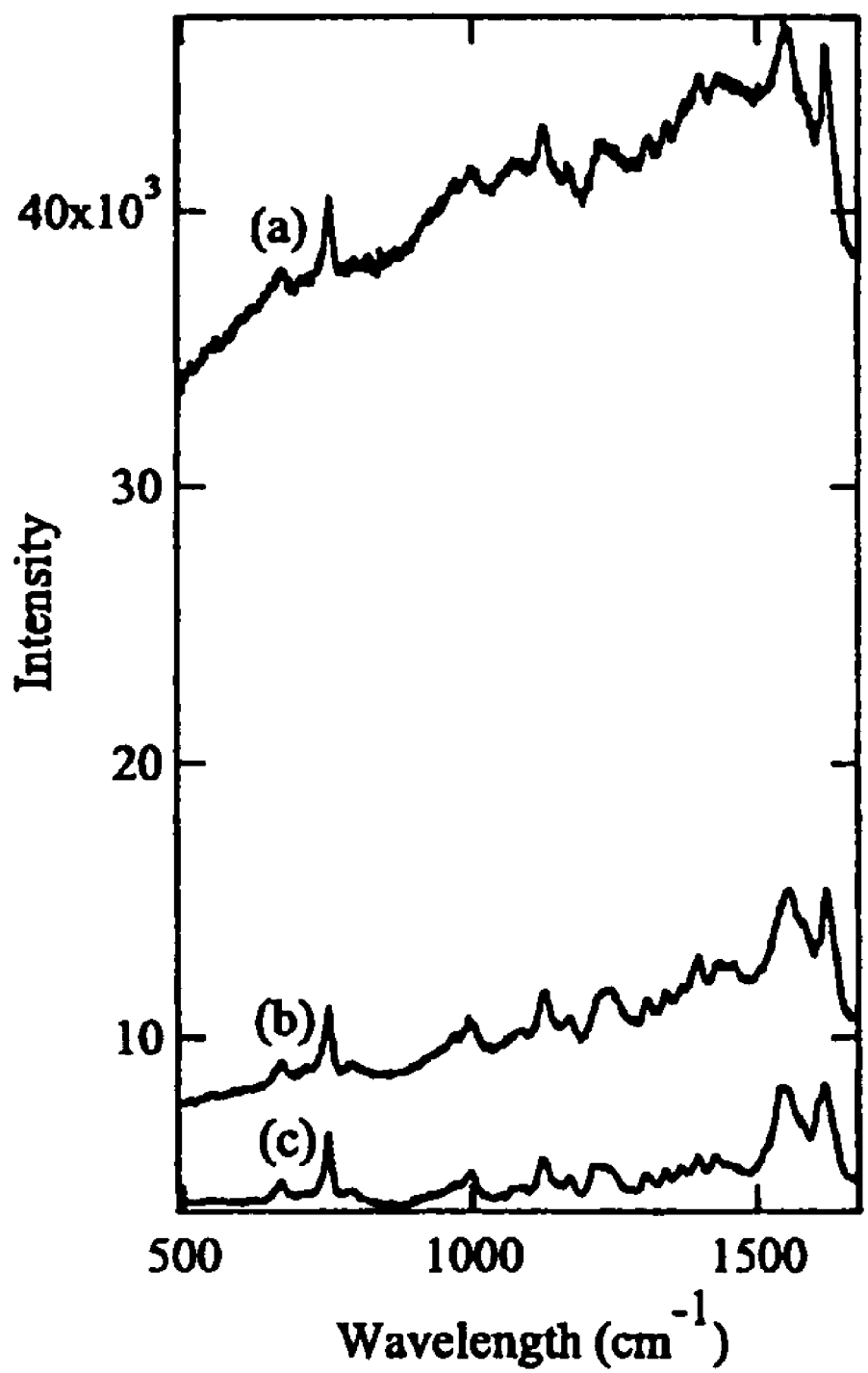
FIG. 4 is a graphical presentation of Raman spectra obtained from myoglobin. Spectra (a) and (b) were obtained from a compressed pellet of myoglobin powder while spectrum (c) was from a solution deposited according to the present invention. Spectrum (b) was obtained after one hour of laser pre-illumination, while the other spectra were obtained with no pre-illumination. A laser power of 0.25 mW (at the sample) and an integration time of 200 seconds were used to collect all three spectra.

As a further example of the protein analyte-buffer segregation methods of the present invention, the Raman spectra of myoglobin is shown in FIG. 4. Spectra (a) and (b) were produced from a compressed pellet of the powdered sample. Spectrum (c) was produced from a selected region of the ring shown in FIG. 1(b) adjacent the outer edge of the deposit. Spectra (a) and (c) were obtained with no pre-illumination while spectrum (b) was obtained after one hour of illumination. All the spectra are taken with an 80× objective and integration time of 200 seconds and a reduced laser power of 0.25 mW, in order to avoid thermal damage produced by optical absorption. As in the case of O-phospho-L-serine, the analyte segregation method of the present invention is again much more efficient and effective than the photobleaching method in reducing fluorescence interferences.

Even in the absence of significant fluorescence interference, the present method produces much higher quality Raman spectra than that those obtained directly from a solid protein powder. This may be due to the fact that the protein solids are typically composed of very thin fibers or flakes, each of which contain too little solid material to produce strong Raman scattering, even after careful optical alignment. Furthermore, although compression of the protein powder into a pellet produces somewhat better results, our experience indicates that Raman spectra obtained from protein pellets are invariably lower in quality than those obtained from the deposits of the same protein in accordance with the present invention when subjected to the same optical excitation and collection conditions.

The image and Raman spectra shown in FIG. 5 illustrate the segregation of protein and buffer species following precipitation on a 50 nm PTFE on stainless steel sample support. The white light optical image in FIG. 5A is that of an about 300 μm×250 μm region near the edge of an about 4 mm diameter circular deposit of a 10 μl volume of solution containing 10 μM lysozyme and 1 mM PBS buffer. The protein and buffer precipitates that formed on the sample support, following solvent evaporation, are evident in this image.

The Raman spectra derived from different regions are shown in FIG. 5B. Spectrum (a) was collected near the edge of the deposition region, while spectrum (b) was collected from a large solid deposit present nearby. The different shapes of these spectra clearly indicate that they derive from different chemical species. For comparison purposes, the top spectrum in FIG. 5B shows a Raman spectrum of a similarly deposited sample of a solution of 10 μM lysozyme without any buffer. The similarity between the top spectrum and spectrum (a) demonstrates that essentially pure lysozyme has segregated away from the buffer upon solvent evaporation. This segregation is further supported by comparison to previously published Raman spectra of crystalline and aqueous lysozyme. The spectrum obtained from region (b) in FIG. 5A, however, is characteristic of the solid dibasic phosphate buffer that has prominent Raman bands at 985, 870, and 514 $cm^{-1}$.

The image and Raman spectra shown in FIG. 6 illustrate the segregation of the same protein and a different buffer species following precipitation again on a 50 nm PTFE on stainless steel sample support. The white light optical image in FIG. 6A is of a similar region near the edge of a similar deposit of a 10 μl volume of solution containing 10 μM lysozyme and 1 mM Tris-HCl buffer. The protein and buffer precipitates that formed on the sample support, following solvent evaporation, are again evident in this image. Normal Raman spectra derived from the identified regions of FIG. 6A are shown in FIG. 6B. Spectrum (a) was collected near the edge of the deposition region, while spectrum (b) was collected from a large deposit present nearby. The different shapes of these spectra clearly indicate that they derive from different chemical species. For comparison purposes, the top spectrum in FIG. 6B is the same as that shown in FIG. 5B and shows a Raman spectrum of a similarly deposited sample of a solution of 10 μM lysozyme without any buffer. The similarity between the top spectrum and spectrum (a) demonstrates that essentially pure lysozyme has segregated away from the buffer upon solvent evaporation. The spectrum obtained from region (b) in FIG. 6A, however, shows prominent Raman bands at 804, 1072, and 1474 $cm^{-1}$, which correspond well to those of the Tris cation.

The absence of any discernible buffer bands in the lysozyme spectra, 5(a) and 6(a) indicates that the protein has deposited in essentially pure form using the methods of the present invention. Micro-Raman measurements near the edge of the deposition region are thus able to identify the protein present in 100-fold excess buffer solutions. The lysozyme spectrum shown in FIGS. 5B and 6B has a comparable signal-to-noise ratio to that reported by others only from solutions of much higher protein concentration and with no buffer. Furthermore, the present spectra were obtained without any solvent or substrate background subtraction, while previous protein solution studies required careful subtraction of the water spectral component from the protein spectra. Furthermore, these previous protein solution studies did not address the issue of potential interference from additional solution components, such as concentrated buffer or trace fluorescence impurities, which would undoubtedly complicate the solvent subtraction procedure and introduce additional noise.

Figures 7A, 7B:
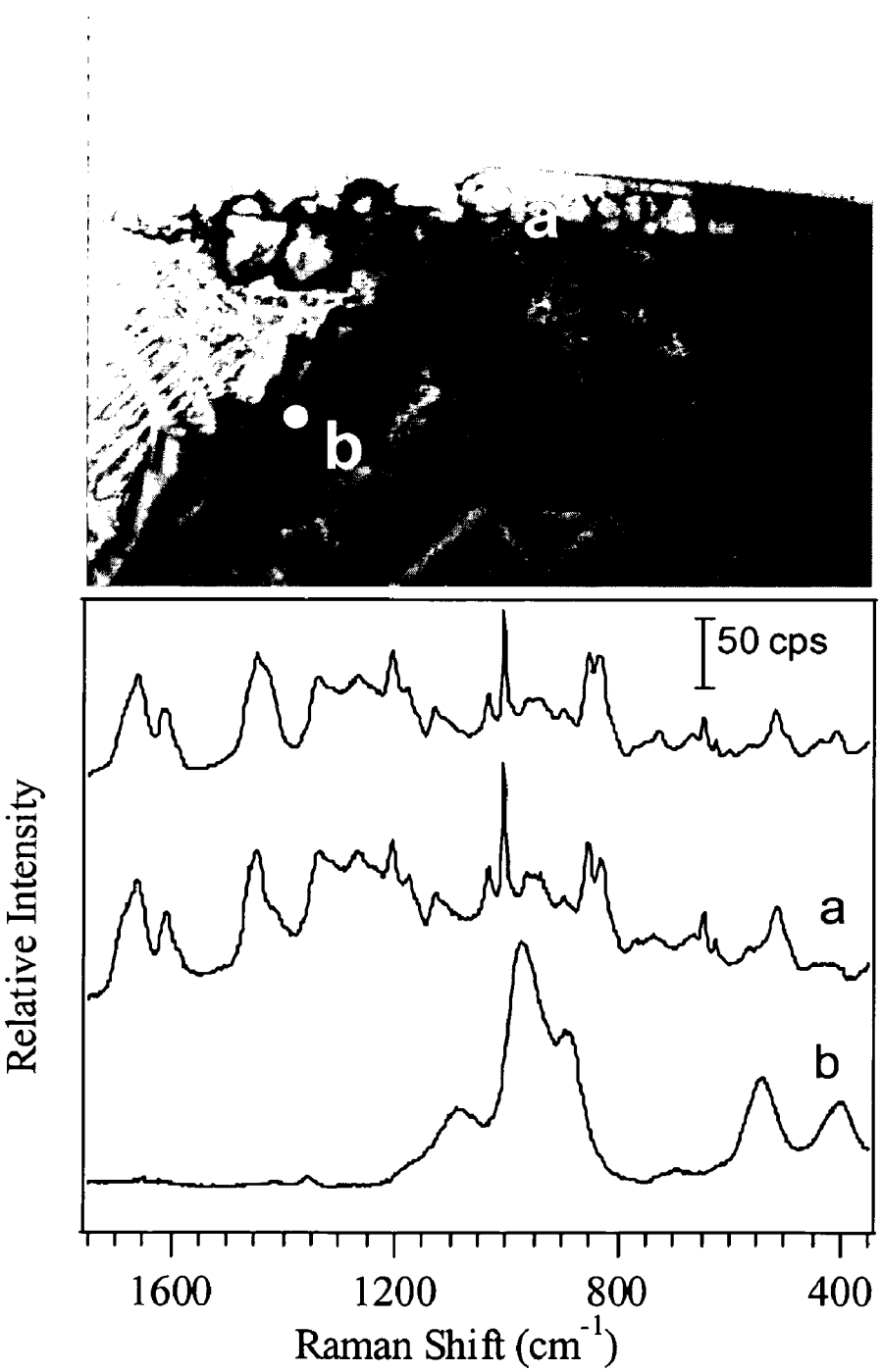
FIG. 7A is a white light optical image of a region near the edge of an about 4 mm diameter circular deposit of a 10 µl volume of solution containing 100 µM human insulin and 10 mM PBS buffer on a 50 nm PTFE on stainless steel sample support.
FIG. 7B shows the corresponding Raman spectra (a) and (b) taken from regions a and b, respectively, shown in FIG. 7A with spectral acquisition times of 60 seconds. The top spectrum in FIG. 7B is the Raman spectrum of lyophilized solid human insulin taken with a 400 second integration time (×30 for scaling purposes).
Figures 8A, 8B:
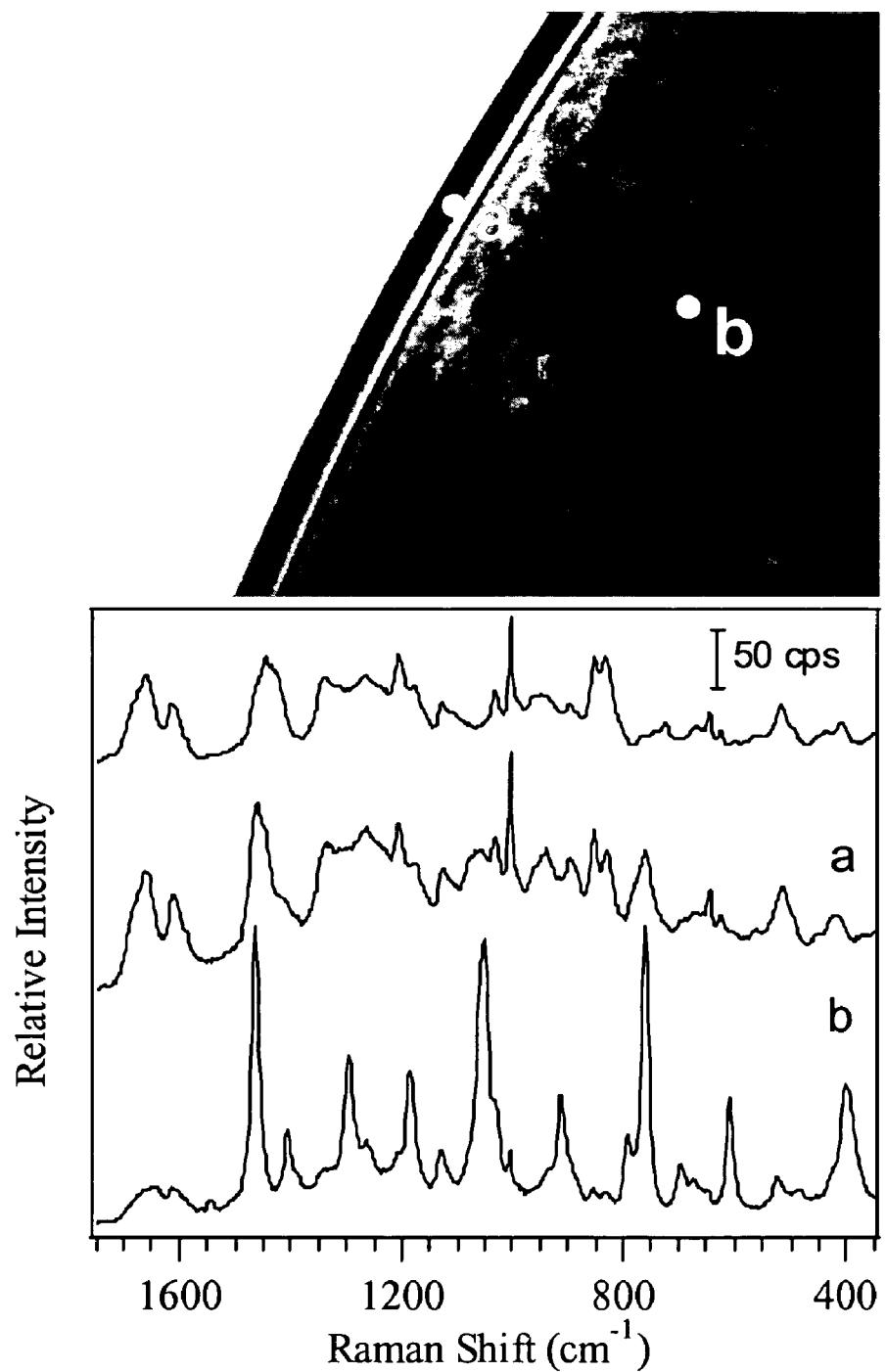
FIG. 8A is a white light optical image of a region near the edge of an about 4 mm diameter circular deposit of a 10 µl volume of solution containing 100 µM human insulin and 10 mM Tris-HCl buffer on a 50 nm PTFE on stainless steel sample support.
FIG. 8B shows the corresponding Raman spectra (a) and (b) taken from regions a and b, respectively, shown in FIG. 8A with spectral acquisition times of 60 seconds. The top spectrum in FIG. 8B is the same as the top spectrum in FIG. 7B.

The generality of the analyte-buffer segregation method of the present invention can be seen from the results shown in FIGS. 7 and 8 for different protein/buffer combinations. The white light optical image in FIG. 7A is from an edge portion of a deposit a 10 μl volume of a solution containing 10 μM synthetic human insulin and 1 mM PBS buffer. The white light optical image in FIG. 8A is from an edge portion of a deposit of a 10 μL volume of a solution containing 10 μM synthetic human insulin and 1 mM Tris-HCl buffer. Raman spectra were again collected from the different regions on the deposited sample spots, and representative spectra are shown in FIGS. 7B and 8B respectively. Spectrum (a) was collected in each instance near the outer edge of the deposited sample spot, where an about 100 μm wide band of precipitated material can be seen in each image. Spectrum (b) was collected in each instance from a region closer to the center of the deposited sample spot. Again, in both FIGS. 7B and 8B, the spectra collected from the two regions differ dramatically. The top spectrum in both FIGS. 7B and 8B, provided for comparison, are the spectrum obtained from lyophilized solid human insulin. The similarity between the top spectrum and spectrum (a) in FIGS. 7B and 8B again indicates that the synthetic human insulin protein is deposited in essentially pure form near the outer edge of the deposited sample. This is further supported by comparisons of the observed Raman spectra to previous reports of the Raman spectra of human insulin. Spectrum (b) of FIG. 7B, on the other hand, again shows prominent Raman bands corresponding to those of the PBS buffer while the spectrum (b) of FIG. 8B shows a spectrum that correspond well to that of the Tris cation. Thus again, the protein and buffer species have segregated after deposition onto the 50 nm PTFE on stainless steel sample support of the present invention, enabling high-quality Raman spectra to be obtained for the protein without interference from the buffer that is present in much higher quantity.

EXAMPLE SET B

For this example demonstrating the high level of analyte discrimination that can be achieved using the methods of the present invention, four peptides were synthetically prepared that have the same amino acid sequence, and differ only in the site of phosphorylation. These four peptides have the same sequence found at the carbonyl terminus (residues 521-533) of the $pp60^{c-src}$ protein tyrosine kinase. When phosphorylated at Tyr-527, this fragment will suppress $pp60^{src}$ activity by binding, either inter- or intra-molecularly, to the SH2 domain of $pp60^{c-src}$. The peptides used in this work were synthesized either in non-phosphorylated form, nP, or phosphorylated at one of three different residues, Ser-522, (sP), Thr-523, (tP), and Tyr-527, (yP), as described in Table 1, which also contains the abbreviated notations used in this example to designate each peptide.

TABLE 1

Peptide sequence, phosphorylation site, and short-hand notation.

| Peptide sequence | Notation |
| --- | --- |
| $H_2N$-Thr-Ser-Thr-Glu-Pro-Gln-Tyr-Gln-Pro-Gly-Glu-Asn-Leu-OH | nP |
| $H_2N$-Thr-Ser-Thr-Glu-Pro-Gln-Tyr($PO_3H_2$)-Gln-Pro-Gly-Glu-Asn-Leu-OH | yP |
| $H_2N$-Thr-Ser-Thr($PO_3H_2$)-Glu-Pro-Gln-Tyr-Gln-Pro-Gly-Glu-Asn-Leu-OH | tP |
| $H_2N$-Thr-Ser($PO_3H_2$)-Thr-Glu-Pro-Gln-Tyr-Gln-Pro-Gly-Glu-Asn-Leu-OH | sP |

Before performing any measurements, the synthetically prepared peptides were purified using reverse-phase HPLC and analyzed using mass spectroscopy (MS) in the Macromolecular Structure Facility at Purdue University. All the peptides were dissolved in high purity water (Millipore) with a peptide concentration of 100 µM. A 10 µL volume of each peptide solution was separately deposited on a substrate consisting of polished stainless coated with 50 nm of PTFE and dried in air at ambient temperature. Each peptide formed a ring on the sample support surface after drying. The spectra are taken with a micro-Raman system employing an 80× objective used to focus 12 mW of He—Ne laser light (632.8 nm) substantially perpendicularly onto the sample surface with spot size of about 2 µm. Raman spectra were collected using a CCD detector-based spectrometer with an integration time of 100 seconds.

Figure 9:
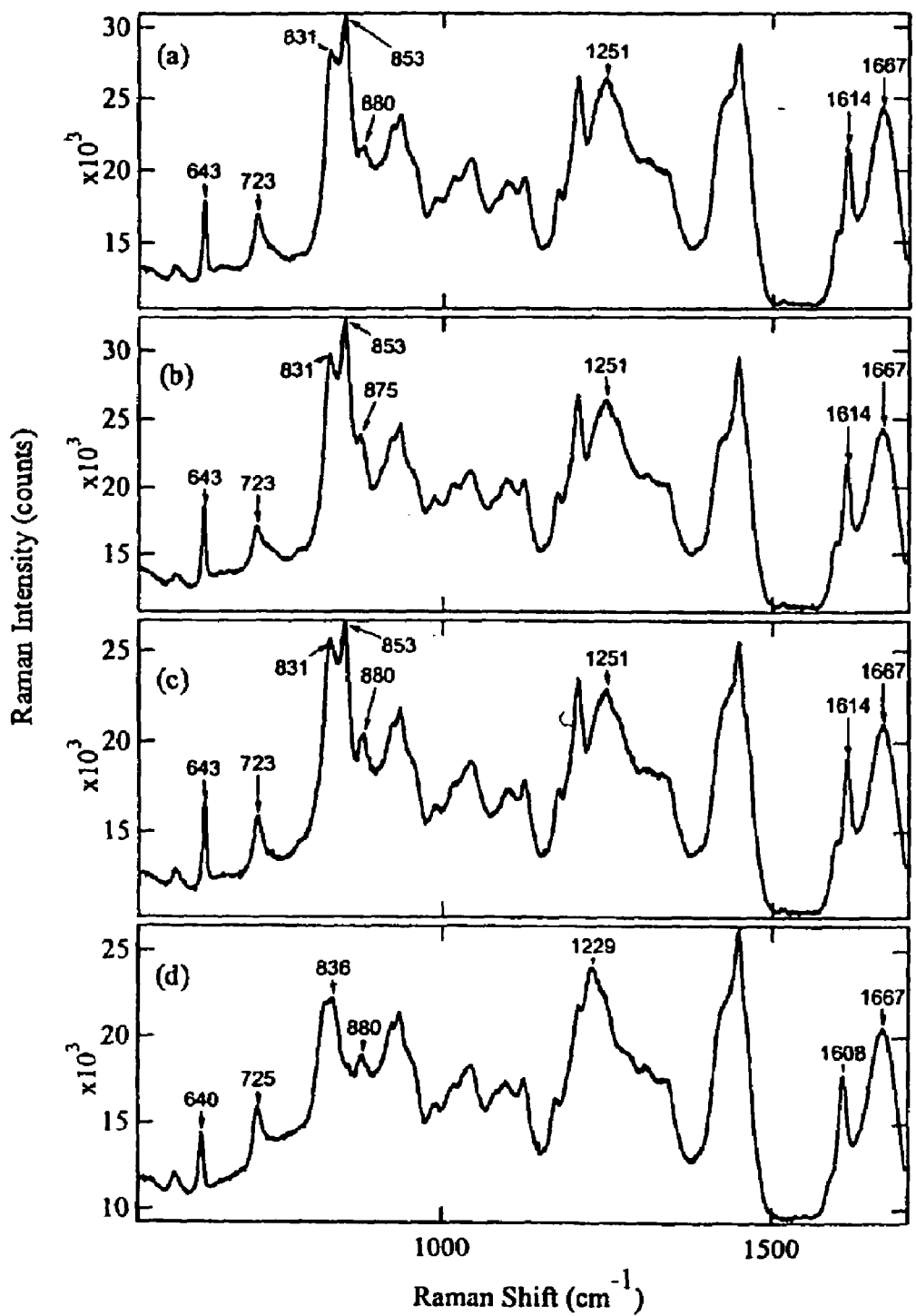
FIGS. 9a-d show the non-enhanced spontaneous Raman spectra taken using the methods of the present invention of four synthetically prepared peptides that have the same amino acid sequence, and differ only in the site of phosphorylation. The volume, 10 µl, and the concentration, 100 µM, of the deposited solution is the same for all samples, as is the integration time, 100 seconds, and laser power, 12 mW.

The spectra shown in FIG. 9 are (a)nP, (b)sP, (c) tP and (d) yP, respectively. The phosphorylation on tyrosine can be seen to introduce more appreciable spectral changes from the non-phosphorylated form than serine or threonine phosphorylation. This may be primarily due to the strong resonance of the strongly Raman active aromatic chromophore present in the side-chain of tyrosine. Some of the spectral differences between yP and nP are very similar to those observed in previously reported resonance Raman studies. Namely, the signal intensity of the 853 $cm^{-1}$ band from the Fermi-resonance tyrosine doublet is reduced dramatically. Also, the peak positions of bands 1614 $cm^{-1}$ (ring stretch), 1251 $cm^{-1}$ (ring-O stretch) are shifted to 1608 $cm^{-1}$ and 1229 $cm^{-1}$, respectively. Furthermore, the 643 $cm^{-1}$ (the ring deformation mode) and 723 $cm^{-1}$ bands are shifted to 640 $cm^{-1}$ and 724 $cm^{-1}$, respectively. The Raman spectral signatures of tyrosine are more easily discerned than those of the non-aromatic serine and threonine amino acid residues. The most noticeable spectral differences among the spectra of tP13mer, sP13mer and nP13mer appear in the region between 750 $cm^{-1}$ and 900 $cm^{-1}$. More specifically, the 880 $cm^{-1}$ band of tP is more intense than that of nP, and is shifted to 875 $cm^{-1}$ in sP. Although these differences are subtle when compared to the larger changes observed upon phosphorylation of tyrosine, they are nevertheless highly reproducible when the spectra were taken from samples deposited on the sample support surfaces of the present invention.

Prior to the classification, all the spectra were processed using a Savistky-Golay second derivative algorithm with a 15 pixel window to remove any fluorescence background. Spectral classification was performed with a partial least square (PLS) discriminant program. The classification error can be determined using the leave-one-out method in which each spectrum in the data set is used as a testing sample after training the PLS algorithm using the remaining spectra. A plot of the leave-one-out PLS classification results can be used to visualize the separability of the Raman spectra obtained from different peptides. In particular, the coordinates of each spectral-vector to a point in the plot are defined by the pseudo-probabilities that this particular spectrum belongs to each class in the training set. One should note that by the nature of the PLS discriminant analysis, the pseudo-probability may be either negative or positive numbers, but the summation of all pseudo-probabilities for each class is necessarily equal to one.

Figure 10:
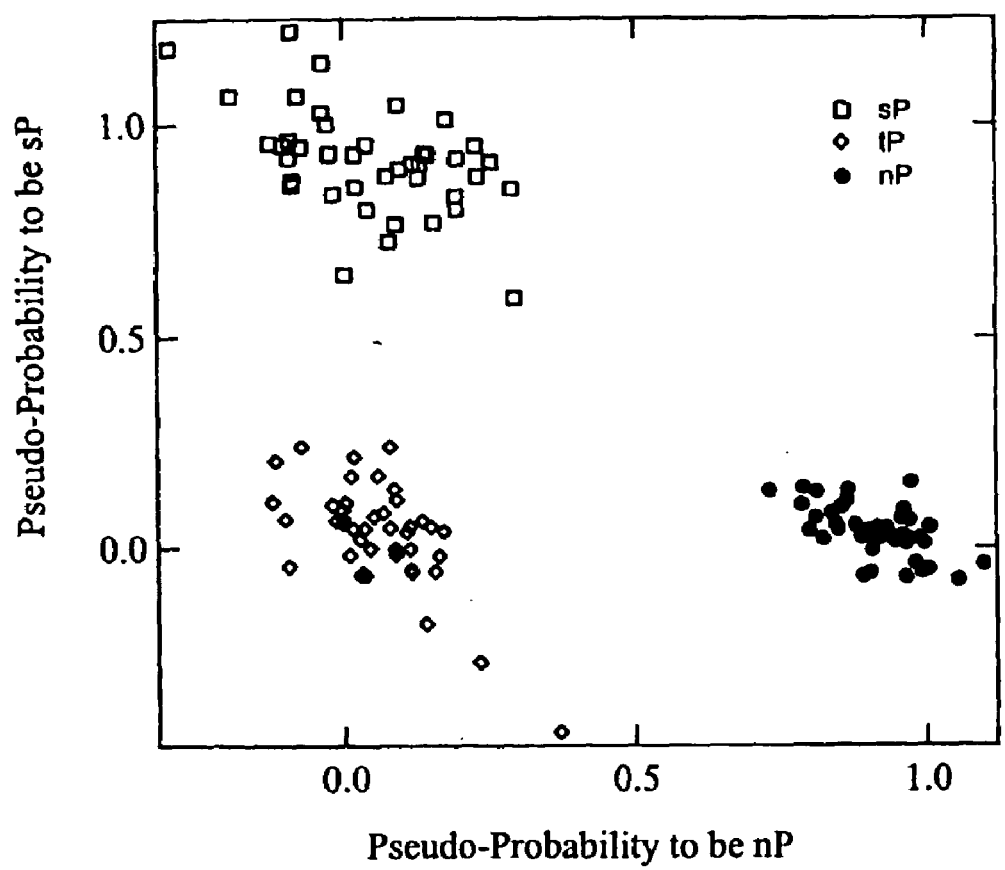
FIG. 10 shows the classification results on the collected spectra for the four synthetically prepared peptides using PLS discriminant analysis with leave-one-out validation method. Each point represents a complete spectrum whose coordinates are the pseudo-probabilities that this particular spectrum belongs to nP and tP. The true identity of each peptide is indicated by the shape of the marker used for each point. The yP peptide results are not shown since this peptide is much easier to spectroscopically distinguish from the other three peptides shown.

The spectral differences between the Raman spectra obtained from specimens prepared according to the methods of the present invention of all four peptides are sufficient to facilitate accurate PLS classifications. FIG. 10 shows a plot for the PLS results for sP, tP and nP, obtained as described above. The yP peptide results are not shown since this peptide is much easier to spectroscopically distinguish for the other three peptides shown. The identity of each peptide is indicated by the shape of the marker used for each point, and the clear separation between the sample clusters indicates that, in spite of the subtle differences between the spectra of these three peptides, the differences when analyzed according to the methods of the present invention are sufficient for highly accurate and reproducible PLS classification.

EXAMPLE SET C

The present example set demonstrates that the present invention can be used to detect and quantify Tyr phosphorylation in tryptic digests of physiologically important proteins. While the peptides used in this example set are produced synthetically, three of them have the same sequence as peptides obtained by tryptic digest of p60c-src, with phosphorylation sites at Y-216, Y-419 and Y-530, respectively, as shown in the sequence in FIG. 11A. The fourth peptide is a shorter variant of the above Y-530 containing peptide. The peptides have varying lengths of between 11 and 32 residues and some contain both Tyr and Phe aromatic residues while others contain multiple Tyr residues. Although the four peptides have quite different Raman spectra, tyrosine phosphorylation induces similar spectral changes in all of the peptides. Furthermore, the present example shows that with the help of a partial least squares PLS multivariate calibration algorithm, the present invention can be used to determine the degree of phosphorylation in a peptide mixture with a standard deviation of ±2%.

The sequences of the four src-peptides used in this study are shown in FIG. 11B. The numbers that indicate the position of each amino acid refer to the proto-oncogene tyrosine-protein kinase src (EC 2.7.1.112) (p60c-src) (c-src) sequence shown in FIG. 11(A). The numbers appearing after the letter Y shown in FIG. 11(B) denote the Tyr phosphorylation site, while the numbers in square brackets denote the location of the sequence in the p60-src protein. The three synthetic src-peptides, Y-216, Y-419, and Y-530[505-536], and the corresponding phosphotyrosyl peptides, were obtained from Alpha Diagnostic Intl. (San Antonio, Tex., USA). The fourth src-peptide, Y-530[524-536], and the phosphorylated derivative thereof were purchased from Bachem (King of Prussia, Pa., USA). The peptides are all certified as 99-100% pure except the pY-216 peptide that is certified as 95% pure.

Aqueous solutions (100 µM) of all the peptides were prepared by dissolving each solid peptide in ultrapure water (Ultrapure Water from VWR), except the longer Y-530 and pY-530 peptides pairs, which were prepared as 50 µM solutions. The pY-530 [505-536] solution needs to be prepared freshly to avoid dephosphorylation, which can be confirmed by MALDI-TOF MS spectra, not shown. A 5 μl volume of each solution was deposited on a substrate consisting of polished stainless steel plate coated with 50 nm of PTFE. After drying in air, normal Raman spectra were collected from the visible ring of peptide using a micro-Raman system having an 80× microscope objective to focus the 12 mW excitation laser (He—Ne, 632.8 nm) to a diameter of about 2 μm perpendicularly on the peptide ring, and each spectrum was integrated for 100 seconds.

Figure 12:
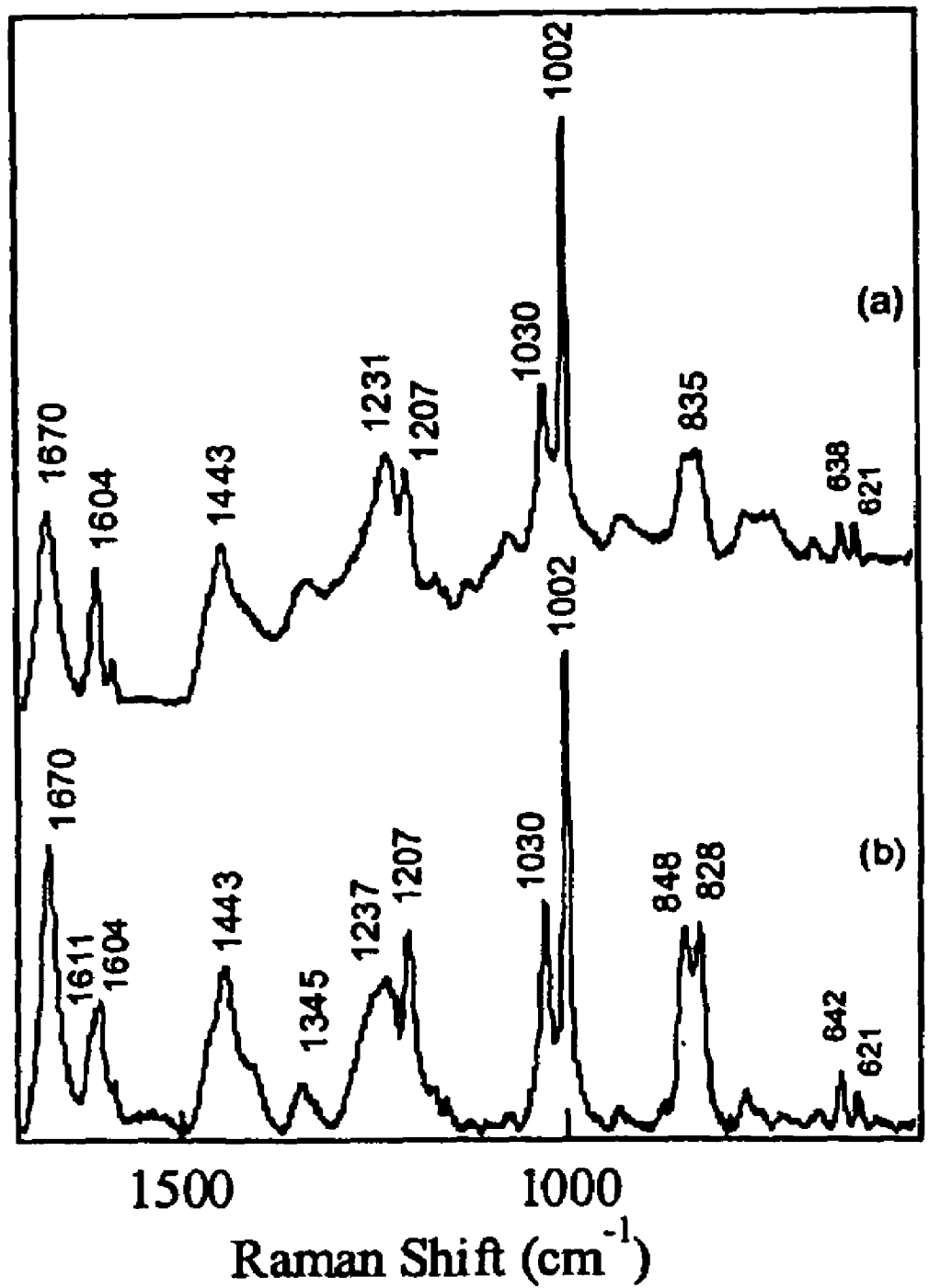
FIG. 12 shows the normal Raman spectra of (a) pY-216 and (b) Y-216 taken using the methods of the present invention. The volume of 5 µL and the concentration of 100 µM of the deposited solution is the same for both samples, as is the integration time, 100 seconds, and laser power, 12 mW.

FIG. 12 shows the Raman spectra of the src Y-216 peptide and the tyrosine-phosphorylated pY-216 derivative. The assignments of the prominent Y-216 Raman bands are: 1670 $cm^{-1}$ (amide I, C=O stretch 80%, N—H deformation and C—N stretch), 1611 $cm^{-1}$ and 1604 $cm^{-1}$ (benzene ring stretch of Tyr and Phe, respectively), 1443 $cm^{-1}$ ($CH_2$ scissoring mode), 1237 $cm^{-1}$ (ring-O stretch of Tyr and amide 111), 1207 $cm^{-1}$ (ring-C stretch of Tyr and Phe), 1030 $cm^{-1}$ and 1002 $cm^{-1}$ (Phe ring breathing mode), 848 $cm^{-1}$ and 828 $cm^{-1}$ (Tyr doublet), 642 $cm^{-1}$ (Tyr ring deformation) and 621 $cm^{-1}$ (Phe ring deformation). The pY-216 peptide has a generally similar spectrum except for the bands associated with the Tyr residue. The Raman band at 1611 $cm^{-1}$ and 1237 $cm^{-1}$ are shifted to 1604 $cm^{-1}$ and 1231 $cm^{-1}$ in pY-216 peptide, respectively, and the intensity of Raman band at 1207 $cm^{-1}$ is apparently reduced. The most pronounced change is the collapse of the 848 $cm^{-1}$ and 828 $cm^{-1}$ overlapping double in the Y-216 spectrum to a single broad band at 835 $cm^{-1}$ in pY-216. In addition a red shift of 642 $cm^{-1}$ to 638 $cm^{-1}$ is observed upon phosphorylation. The red-shift (lower frequency) of the 1611 $cm^{-1}$, 1237 $cm^{-1}$ and 642 $cm^{-1}$ bands may be due to the replacement of a lighter H atom with a heavier phosphate group. Similar observations have been reported in UV resonance Raman spectra upon tyrosine phosphorylation and crystalline Raman spectra upon the hydrogen bonding states of tyrosine phenolic hydroxyl group. The 1206 $cm^{-1}$ peak is assigned to the C-ring stretch of both Tyr and Phe residues. Comparison between the two spectra suggests an attenuation of the relative intensity of the 1206 $cm^{-1}$ band upon Tyr phosphorylation.

The tyrosine doublet at ~840 $cm^{-1}$ (which collapses to a single band upon phosphorylation) has been assigned to a Fermi resonance between the symmetric ring-breathing fundamental of Tyr and the overtone of the out-of-plane ring vibration of Tyr. Tyr phosphorylation appears to bring the two bands into nearly perfect resonance. Since the weak Fermi resonance splitting (of the order 20 $cm^{-1}$) is close to the width of each band (~20 $cm^{-1}$), the Fermi doublet appears to form a single broad, flat-topped peak upon phosphorylation.

Figure 13:
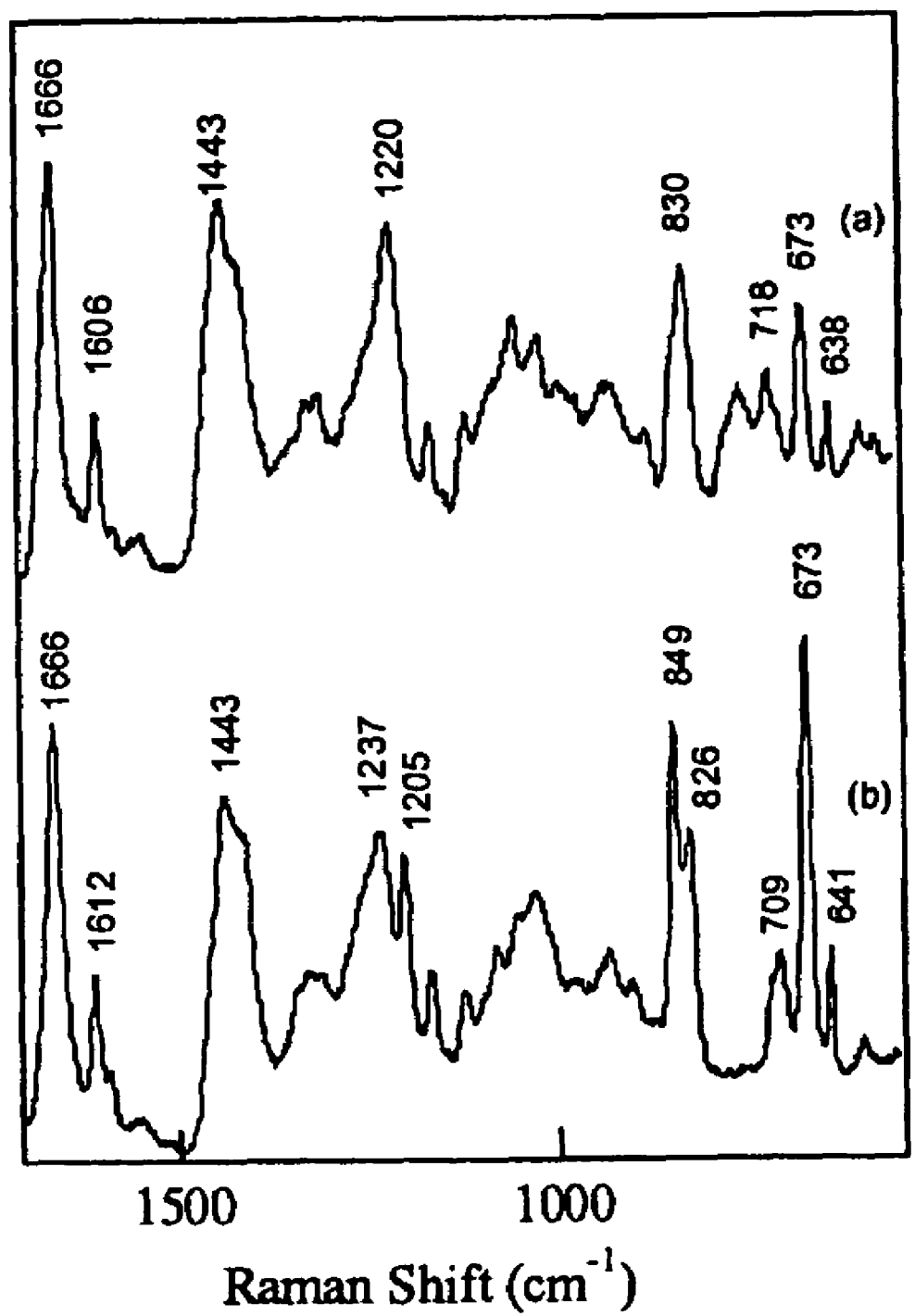
FIG. 13 shows the normal Raman spectra of (a) pY-419 and (b) Y-419 taken using the methods of the present invention. The experimental conditions are the same as in FIG. 12.

FIG. 13 shows the Raman spectra of the src Y-419 peptide and the tyrosine-phosphorylated derivative thereof. Unlike Y-216 the Y-419 peptide sequence does not contain Phe (F) residue (see FIG. 11B). The Phe residue has a strongly Raman active sharp peak at 1001~1002 $cm^{-1}$ (aromatic ring breathing mode), which appears in FIG. 12, but not in FIG. 13. The normal Raman spectrum of Y-419, like that of Y-216, shows the 1666 $cm^{-1}$ (amide 1) 1606 $cm^{-1}$ (benzene ring stretch of Tyr), 1443 $cm^{-1}$ ($CH_2$ scissoring mode), 1239 $cm^{-1}$ (ring-O stretch of Tyr and amide 111), 1205 $cm^{-1}$ (ring-C stretch of Tyr), 849 $cm^{-1}$ and 826 $cm^{-1}$ (Tyr doublet), and 641 $cm^{-1}$ (ring deformation of Tyr). In the normal Raman spectrum of pY-419 peptide, one again observes the replacement of the doublet peaks around 850-820 $cm^{-1}$ with a single broad band at 830 $cm^{-1}$. Without the interfering Phe features, the shift of 1612 $cm^{-1}$ to 1606 $cm^{-1}$, and the attenuation of 1205 $cm^{-1}$ peak becomes more apparent. The red shift of 641 $cm^{-1}$ to 638 $cm^{-1}$ is again observed upon phosphorylation. Those spectral changes are consistent with those observed in the Y-216/pY-216 peptides, and all appear to be general signatures of Tyr phosphorylation. The shift of 1237 $cm^{-1}$ to 1220 $cm^{-1}$ peak is 17 $cm^{-1}$ in src Y-419/pY-419 peptides, which is larger than 6 $cm^{-1}$ shift in Src Y-216/pY-216 peptides.

Figure 15:
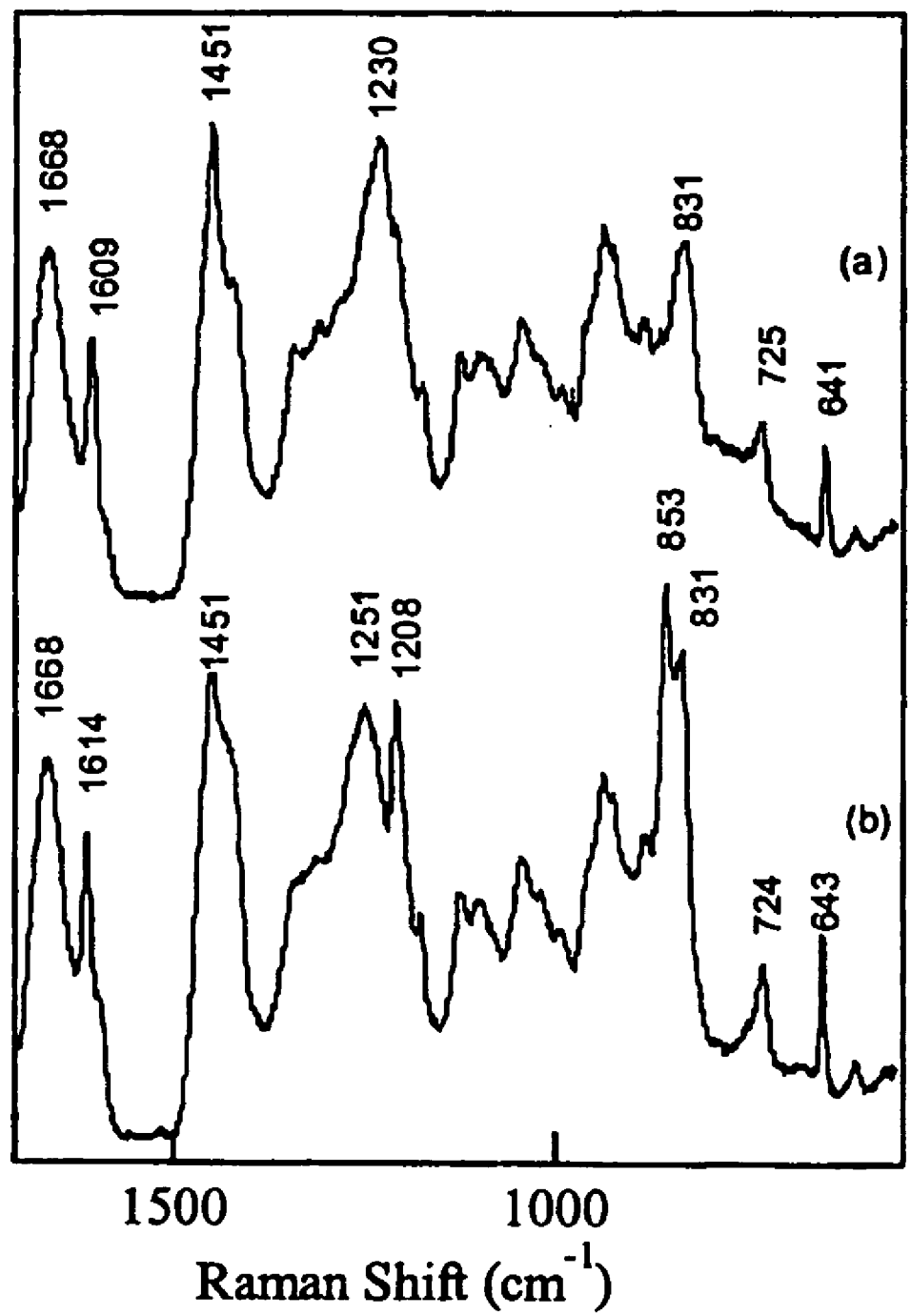
FIG. 15 shows the normal Raman spectra of (a) pY-530 [524-536] and (b) Y-530[524-536] taken using the methods of the present invention. The experimental condition is same as in FIG. 12.

A very similar phenomenon can also be found in the normal Raman spectra of Y-530/pY-530[524-536], as shown in FIG. 15 (and this peptide also lacks a Phe residue). The different wavenumbers of red-shift can not only be explained by the phosphorylation occurring at Tyr residue for the peptides with or without Phe residue in their sequences. Therefore, another explanation can be related with the amide III band that overlapped with ring-O stretch of Tyr. Amide III band is mainly contributed from C—N—H in plane bending, and the amide III band is sensitive to the structure change related with β-sheet-like (1227-1240 $cm^{-1}$) or random coil (1240-1250 $cm^{-1}$) peptides/proteins secondary structures than amide I band. Therefore, the Amide III band suggests the peptides without Phe residue follow the random coil to β-sheet-like structural change upon Tyr-phosphorylation, while peptides containing Phe residue remain the β-sheet-like structure during the phosphorylation process.

Figure 14:
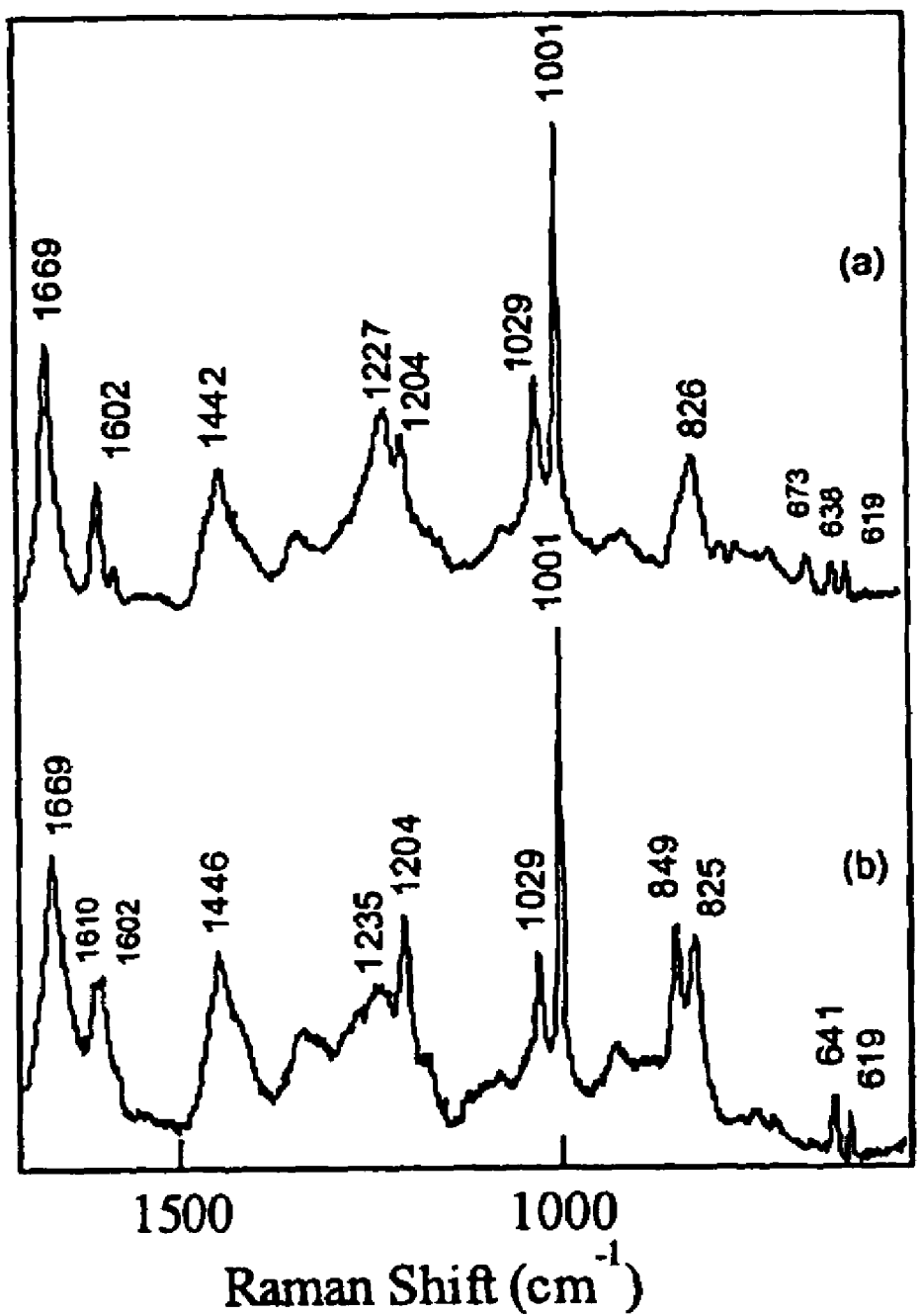
FIG. 14 shows the normal Raman spectra of (a) pY-530 [505-536] and (b) Y-530[505-536] taken using the methods of the present invention. Both peptides have concentration as 50 µM, and the other experimental condition are the same as FIG. 12.

The Raman spectrum for the src Y-530[505-536] peptide is shown in FIG. 14. The src Y-530[505-536] peptide sequence contains three Phe residues and three Tyr residues. Note that although this Y-530[524-536] peptide contains the sequence of src Y-530[524-536] peptide, the normal Raman spectra of the two peptides are quite different because the Y-530 [505-536] peptide contains nineteen additional amino acid residues. Only the Y-530 residue in the pY-530[505-536] peptide is phosphorylated under normal physiological conditions, and this is the peptide whose spectrum is shown in FIG. 12. In spite of the multiple Tyr and Phe residues in this peptide, the processes of the present invention again show that phosphorylation converts the doublet to a single peak at 826 $cm^{-1}$, as evident in FIG. 14. The spectrum of Y-530[505-536] is similar to that of Y-216 since they both contain Phe.

It should be noted that the amide I bands of all of peptides are around 1666-1670 $cm^{-1}$, which suggests that they all have either a β-sheet-like or random coil structure. Combined with the analysis of amide III bands, Y-216 and Y-530[505-524] may give β-sheet-like structure, but Y-419 and Y-530[524-536] stay as random coil structure, while all the phosphorylated peptides may give β-sheet-like structure. Thus, the methods of the present invention can be used to detect and quantify Tyr phosphorylation in tryptic digests of physiologically important proteins and provide information as to the conformational structure of peptides.

Figure 16:
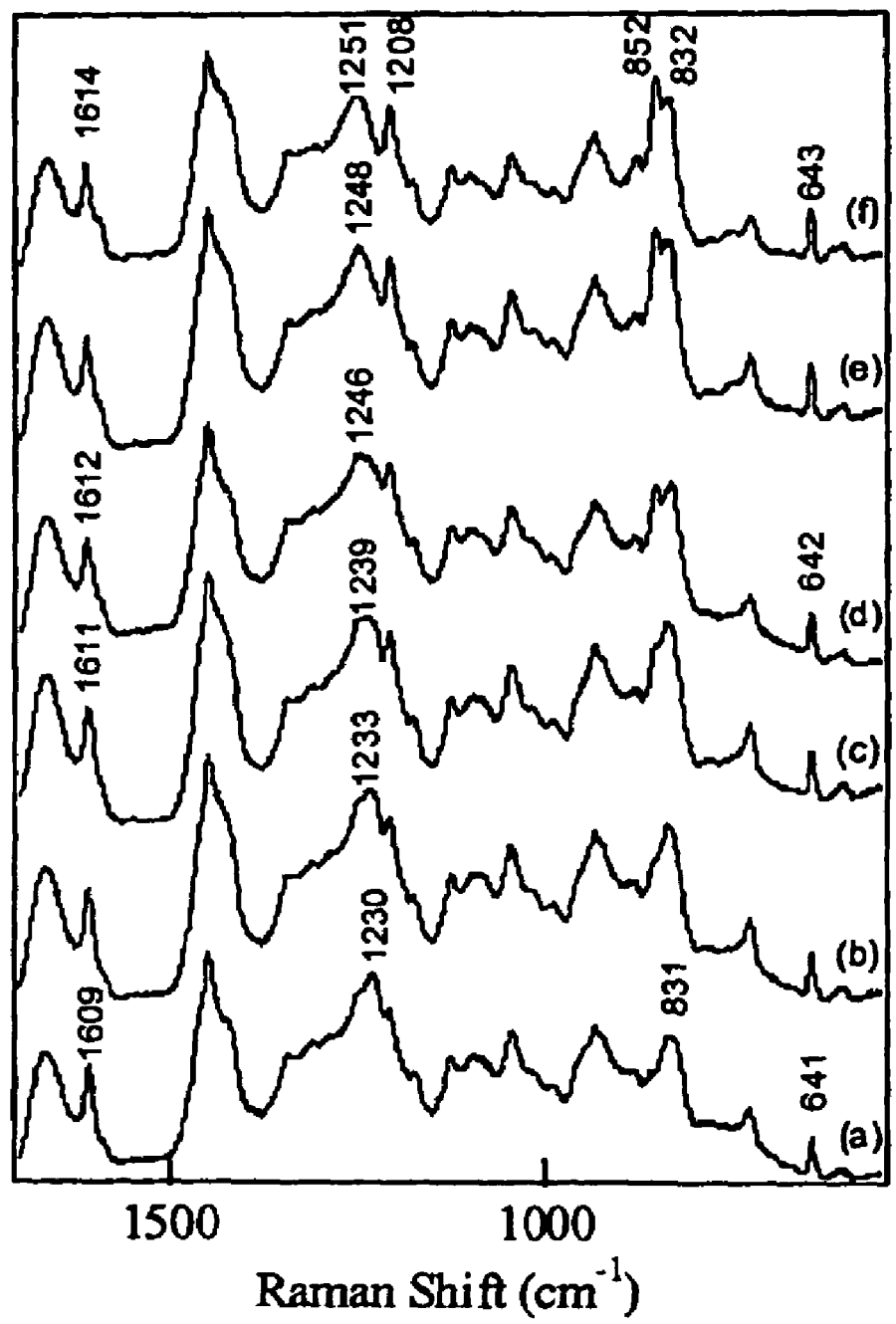
FIG. 16 shows the normal Raman spectra of Y-530[524-536] peptide mixtures with (a) 0%, (b) 20%, (c) 40%, (d) 60%, (e) 80% and (f) 100% phosphorylation at the Y-530 residue. The total peptide concentration and other conditions are the same as in FIG. 12.

By taking advantage of the normal Raman spectral changes associated with phosphorylation, the methods of the present invention can also be used to measure the composition of partially phosphorylated Y/pY peptide mixtures. To demonstrate this, mixtures of the src Y-530[524-536] and pY-530[524-536] peptides with various relative compositions were prepared and analyzed using PLS calibration. FIG. 16 shows the normal Raman spectra of src Y530[524-536], (f), src pY530[524-536], (a), and their mixtures, spectra (b)-(e).

Figure 17:
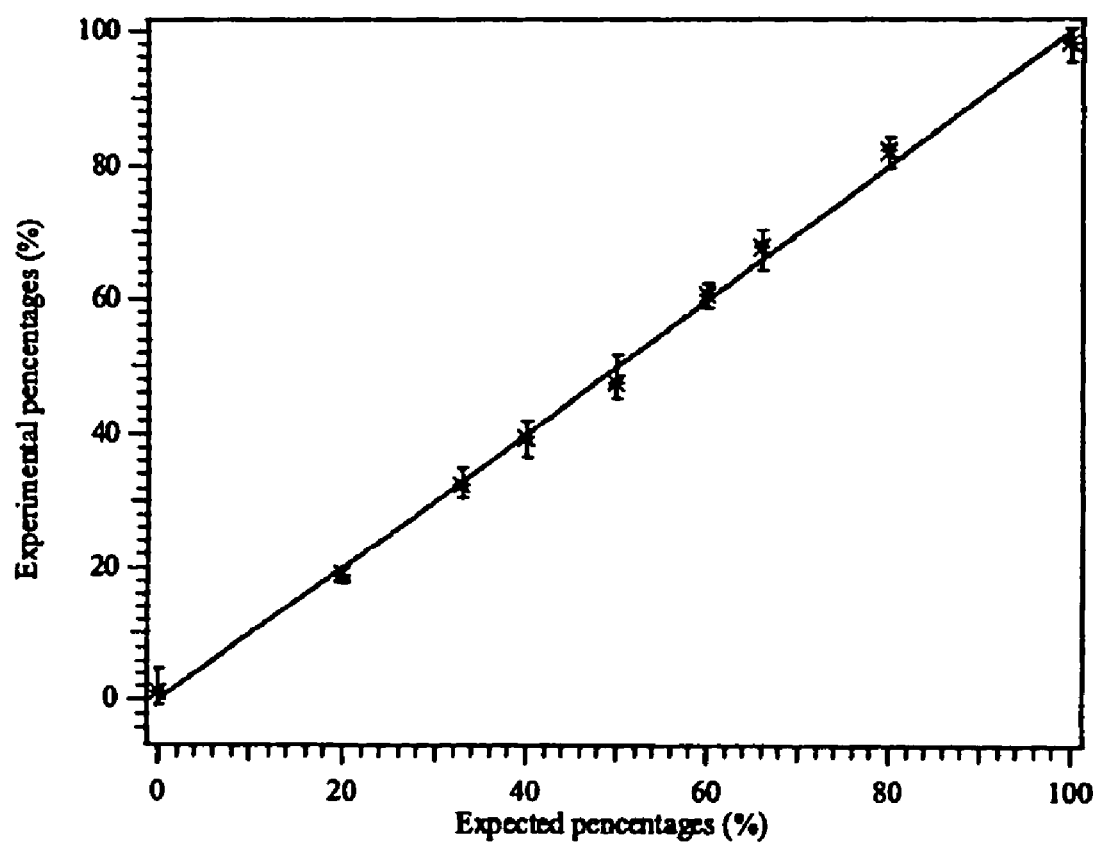
FIG. 17 shows the normal Raman/PLS derived predictions of percent phosphorylation of Y-530[524-536] peptide mixtures (see spectra in FIG. 14) plotted as a function of the actual percent phosphorylation. The error bars indicate the variation of predictions obtained from 20 independently collected spectra. The average standard deviation for all 180 measurements is ±2%.

Except for composition differences, the experimental conditions, including the total peptide concentration (100 μM), character of sample support, etc., were kept the same for each measurement. As shown in FIG. 16, the peaks at 1614 $cm^{-1}$, 850~820 $cm^{-1}$ (tyrosine doublet) and 643 $cm^{-1}$ in the normal Raman spectrum change gradually with increased phosphorylation to 1609 $cm^{-1}$, 831 $cm^{-1}$, and 641 $cm^{-1}$, while 1208 $cm^{-1}$ attenuates. To train and test the PLS algorithm (using the leave-one-batch-out method), 20 spectra of each composition were used. The resulting predicted percent phosphorylation for each mixture is shown in FIG. 17. The best-fit line shows the excellent linear correlation with the known compositions. The error bars indicate the maximum deviation of predicted percentages obtained from 20 independent measurements at each composition. The standard deviation between the predicted and actual composition for all 180 measurements is ±2%.

The present example set demonstrates that by using the methods of the present invention one can see that peptides with different sequences show consistent changes in normal Raman spectral features induced by tyrosine phosphorylation. The most prominent changes are the collapse of a Tyr Fermi resonance doublet and the attenuation of a Tyr aromatic ring-C stretch upon phosphorylation. These easily observable changes appear to be universal normal Raman signatures of tyrosine phosphorylation. In addition, more subtle red shifts of the Tyr ring breathing, deformation and ring-O stretch are also observed. Mixtures containing incompletely phosphorylated peptides produce Raman spectra whose shape can be used to quantify the degree of phosphorylation. This has been demonstrated using the sample supports and the methods of the present invention including a PLS multivariate calibration algorithm that is trained to recognize spectra produced by samples with various degrees of phosphorylation.

EXAMPLE SET D

Figure 18:
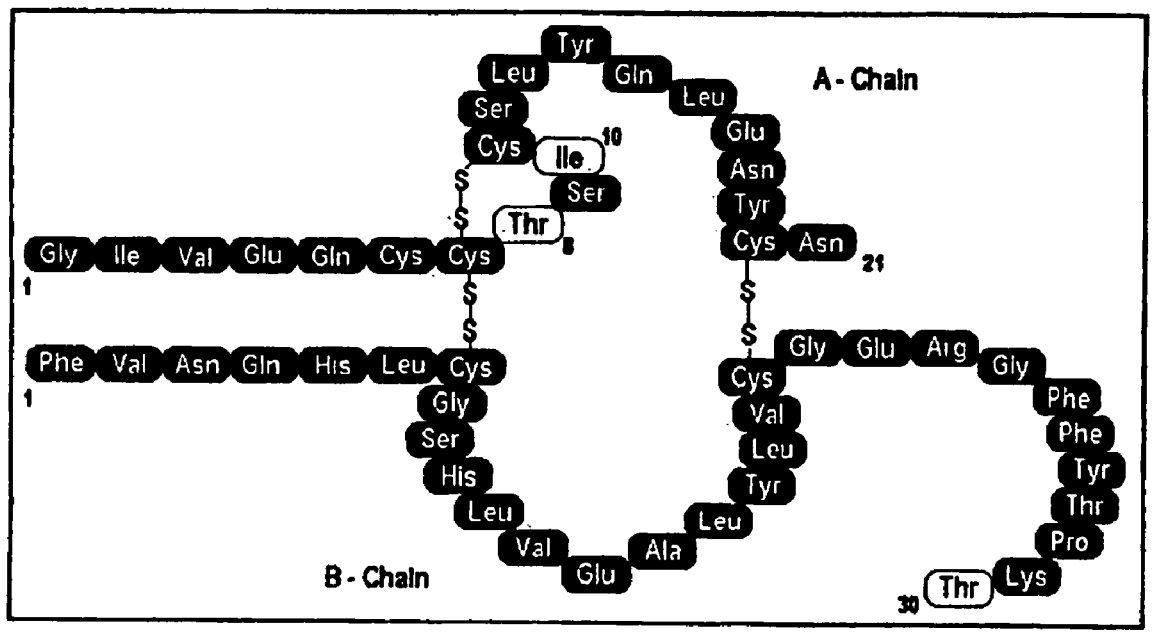
FIG. 18 shows the known sequence of human insulin with the amino acids represented in white being the only locations in which the human, bovine and porcine insulin variants differ, as indicated in Table 2.

It is well known that insulin is a hormone produced in the pancreas to decrease the level of sugar in the blood. The structure of insulin was completely elucidated in 1955 by Frederick Sanger, and was the first protein to be fully sequenced as shown in FIG. 18. Insulin is made up two peptide chains, A with 21 amino acid residues and B with 30 residues, linked by two disulfide bonds connecting cysteine residues A7 to B7 and A20 to B19. The A chain has an additional internal disulfide bond between residues A6 and A11. The primary structures of the bovine, porcine, and human insulins are very similar. Human and porcine insulin differ only by one amino acid at the B30 residue, which is threonine, Thr, or alanine, Ala, respectively. Bovine and human differ by three amino acids identified in Table 2. The three insulin variants have similar tertiary structures.

TABLE 2

Sequence Differences Between Various Insulins

| RESIDUE | Bovine | Human | Porcine |
|---|---|---|---|
| A8 | Ala | Thr | Thr |
| A10 | Val | Ile | Ile |
| B30 | Ala | Thr | Ala |

The normal Raman spectra of these insulin variants can be obtained using the methods of the present invention. Although the resulting spectra are very similar, they can be used to accurately and reproducibly distinguish these insulin variants, with the aid of data processing steps, namely: Savisky-Golay second derivative pre-processing and multivariate partial least squares (PLS) classification. This example also demonstrates the use of the protein isolation techniques of the present invention in combination with reverse-phase high performance liquid chromatorgraphy (RPHPLC).

Bovine, human and porcine insulin were purchased at Sigma. Trifluoroacetic acid (TFA) was procured at Acros and Acetonitrile at Mallinckrodt. Ultra pure water (Milli Q) was used to prepare all solutions. Solutions of bovine and human insulin with concentrations of 2 µg/µL were prepared using 0.1% TFA as solvent. The mobile phase of the RPHPLC was made up by two solutions: 0.1% TFA in 100% water or 0.1% TFA in 100% acetonitrile. The column used was a $C_4$ Microsorb-MV column (300 Å; 46×250 mm; Rainin), which was equilibrated in 0.1% TFA. The gradient applied went from 0% B to 60% B during 40 minutes and, then, to 100% B over 10 minutes. A UV detector (Milton Roy SpectraMonitor 3100) was set at 254 nm to detect the chromatographic peaks. The column was returned to the initial conditions of 0% B. The chromatographic peaks containing insulin were collected for further analysis. The concentration of the solution after RPHPLC was measured using a Cary 300 ultraviolet-visible (UV-VIS) spectrophotometer. Each sample was held in a quartz cell with a path length of 1 cm. The wavelength used for the concentration analysis was 280 nm. For the classification experiments, the insulin solutions were lyophilized after the purification step and re-dissolved in ultra pure water.

Gold coated glass substrates were prepared by pretreating glass microscope coverslips by sonicating for 30 minutes in a 10% ethanolamine solution. Chromium (20 nm) and gold (20 nm) layers were sequentially deposited on these glass slide covers with thermal deposition at <$10^{-5}$ Torr pressure using a Turbo vaccum evaporator (Fullam, EFFA). The deposition speed of 0.1 nm/s was monitored using a Cressington thickness monitor (MEM 10) equipped with a FTM-2 crystal (Ted Pella, Inc.). The sample support was then sonicated in a 50 part acetone and 50 part water solution for 5-10 minutes, rinsed thoroughly with ultra pure water, and dried using Argon gas. The gold substrates were further modified by forming a self assembled monolayer (SAM) by immersing the substrates for 24 hours in a 1 mM ethanolic solution of hexadecathiol.

Then, 10 µL of the RPHPLC insulin fractions were deposited onto the surface and dried in air at ambient temperature before collecting Raman spectra from the ring of protein precipitate around the edge of the deposited spot. The normal Raman spectra measurements were preformed after the samples appeared to have completely dried. However, since the resulting spectra of bovine insulin is essentially identical to that previously reported for native insulin in an aqueous solution and clearly differs from the reported spectra for denatured insulin, the deposits apparently retain sufficient water to hydrate the proteins and maintain them in native configuration.

To test the influence concentration differences on the Raman spectra, solutions of various concentrations, 3 µM to 400 µM, were deposited and spectroscopically analyzed. To test the effects of the chemical structure of the surface on the classification process, some of the solution volumes were deposited onto the modified-gold sample supports as described above. Other solution volumes were deposited onto either 50 nm PTFE coated stainless steel sample supports or on a 30 to 50 µm PTFE coated region of a commercial stainless steel MALDI sample support (Bruker Anchor Chip). The samples were dried in a desiccator before the Raman measurements were made. All the above sample supports produced essentially similar insulin Raman spectra, above a very small essentially featureless substrate spectral background. Neither the SAM nor the 50 nm PTFE substrate coatings are thick enough to produce any detectable Raman features, while the underlying polished gold or steel is highly reflective and also produces very little background signal. The background signal for the 30-50 μm PTFE coated commercial stainless steel MALDI sample support was greater than that of the 50 nm PTFE coated stainless steel sample support of the present invention, producing some Raman features with peaks around 1381 $cm^{-1}$ and 733 $cm^{-1}$.

The Micro-Raman system used for the Raman spectral measurements consisted of a 632.8 nm wavelength He—Ne laser (Spectra Physics model 127) with about 15 mW directed perpendicularly at an about 2 mm diameter laser spot on the deposited protein sample. The laser was focused onto the sample using a 80× microscope objective (Olympus MDPlan 80). The backscattered Raman signal was collected by the same microscope objective. After collimation and holographic filtering, the backscattered Raman signal was detected using a liquid nitrogen-cooled CCD detector (Princeton Instruments LN/CCD 1152E) mounted to a spectrograph (ISA HR320 f/4.2) with a 1200 grooves/mm ruled grating. An exposure time (CCD integration time) of 100 seconds was used to collect each Raman spectrum.

TABLE 3

| Frequencies ($cm^{-1}$) | Assignments |
| --- | --- |
| 516 | v(S—S) |
| 626 | Phe |
| 646 | Tyr |
| 673 | V(C—S) of C—S—S—C |
| 726 | Skeletal bending |
| 770 | Skeletal bending |
| 834 | Tr |
| 855 | Tyr |
| 898 | v(C—C) |
| 962 | v(C—C) |
| 1007 | Phe |
| 1035 | Phe |
| 1130 | v(C—N) |
| 1180 | Tyr |
| 1210 | Tyr & Phe |
| 1267 | Amide III (α-helical) |
| 1319 | CH deformation |
| 1341 | CH deformation |
| 1450 | $CH_2$ deformation |
| 1616 | Tyr |
| 1663 | Amide I (α-helical structure) |

Figure 19:
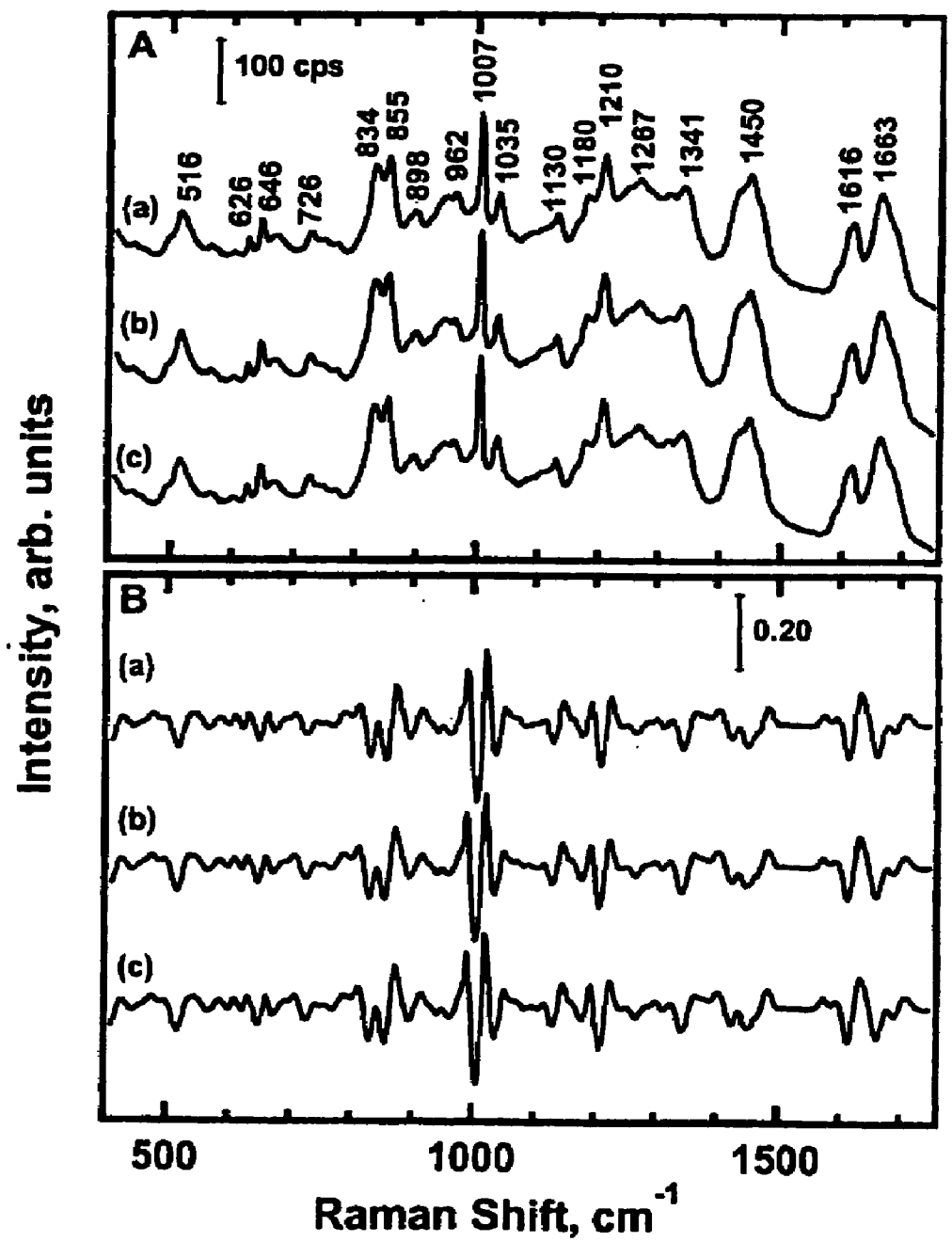
FIG. 19A shows the average Raman spectra of (a) human, (b) bovine, and (c) porcine insulin.
FIG. 19B shows the corresponding normalized second derivative (NSD) of the spectra shown in FIG. 19A.

FIG. 19A shows average Raman spectra of the three insulin variants collected after deposition of 10 μl of 100 μM solutions. Similar measurements using other concentrations and sample supports demonstrate that the spectral differences resulting from different deposition concentrations of from deposition on the three different types of sample supports are invariably smaller than the spectral differences between the insulin variants. More specifically, the concentration and substrate induced spectral changes are smaller than the noise in each spectrum, while differences between insulin variants are large enough to be reproducibly detected and used as the basis for multivariate spectral classification as described below. Table 3 lists previously reported assignments of some prominent insulin Raman bands. One can note that phenylalanine (Phe) and tyrosine (Tyr) residues produce many of these vibrational signatures. This is believed to be a result of the high Raman scattering cross section of the aromatic rings in these residues.

FIG. 19B shows the average normalized second derivative (NSD) pre-processed spectra of the three insulin variants. The NSD pre-processing was performed using a Savitsky-Golay second derivative algorithm with a 15 pixel window, and normalized so that the area under the square of each second derivative spectrum is equal to one. Thus each NSD spectrum corresponds to an N-dimensional unit vector where N is the number of pixels in the spectrum. This pre-processing procedure helps suppress both broadband background and pixel noise while retaining Raman spectral features.

Figure 20:
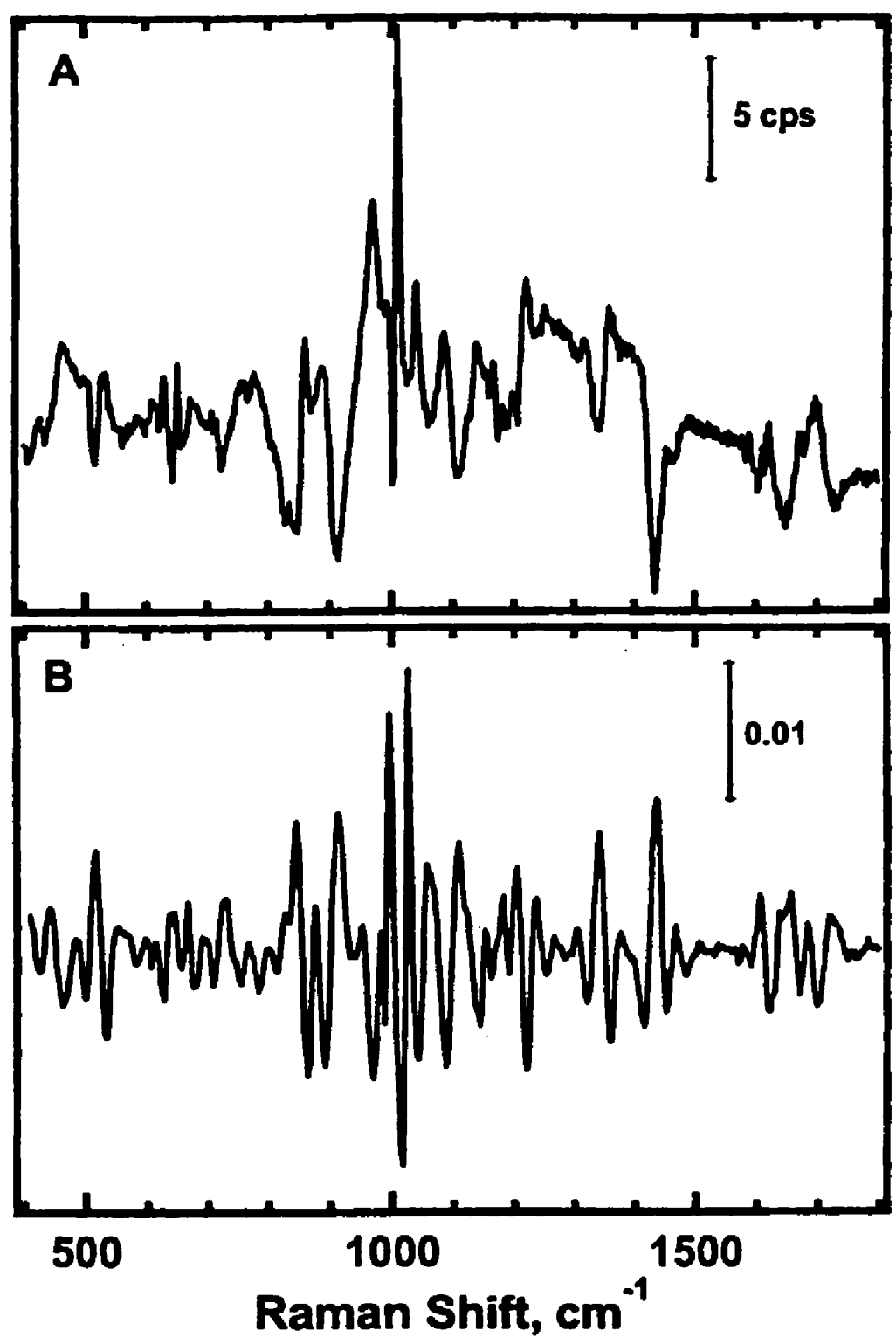
FIG. 20A shows the average Raman difference spectra for human minus porcine insulin.
FIG. 20B shows the average NSD difference spectra corresponding to FIG. 20A.

FIG. 20A shows the difference spectra for human minus porcine insulin obtained from the average Raman signal. FIG. 20B shows the corresponding NSD spectra for the same difference. The Raman difference spectra were obtained by manually minimizing the 1616 $cm^{-1}$ (Tyr) and 1663 $cm^{-1}$ (Amide I) spectral features while the NSD difference spectra were obtained by direct subtraction. The results reveal small spectral differences (approx. 5%) appearing as positive and negative features throughout the spectra. These difference spectra are qualitatively similar to those obtained using other pairs of insulin variants. The most pronounced features in the difference spectra are those associated with the aromatic Phe ring breathing mode around 1000 $cm^{-1}$, but a number of other prominent difference features are evident through out the spectra.

Figure 21:
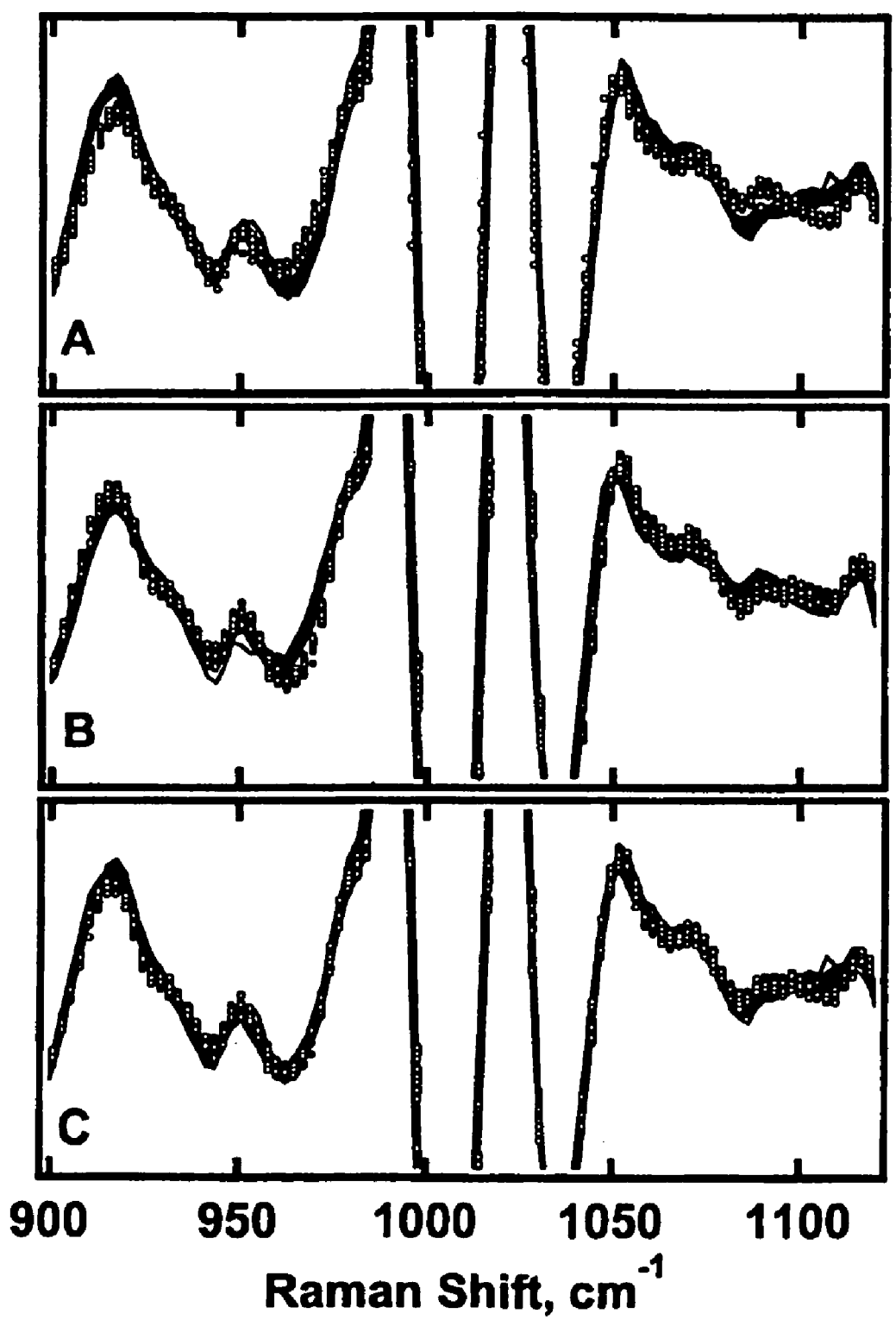
FIGS. 21A-C show a superposition of thirty individual NSD Raman spectra of insulin variants where (A) is human (black) and bovine (gray), (B) is bovine (black) and porcine (gray), and (C) is human (black) and porcine (gray).

FIG. 21 offers another view of the NSD spectral differences in the 900 $cm^{-1}$ to 1100 $cm^{-1}$ spectral region. In this case, 30 individual spectra obtained form each insulin variant are superposed to reveal the small systematic differences between the corresponding NSD spectra. These results are particularly noteworthy as they reveal that the variations between spectra obtained from a given insulin variant are smaller than the variations between different insulin variants. This reproducibility is maintained even when the initial concentration of the solutions, and the type of sample support used, are changed. This indicates that the spectral differences that are observed are indeed correlated with the structural differences between the insulin variants rather than deposition concentration or sample support structure. Such systematic spectral variations can be used as the basis for automated PLS training and classification of insulin variants.

Spectral differences are evident not only in the 1000 $cm^{-1}$ Phe stretch region, but also in the vicinity of the backbone C—C stretching (896, 918 and 960 $cm^{-1}$) and the C—N stretching region (1052 to 1116 $cm^{-1}$) bands. Other regions in the spectra, such as those shown in FIG. 20, containing S—S (516 $cm^{-1}$) and C—S (663 and 673 $cm^{-1}$) and backbone bending (726, 750 and 770 $cm^{-1}$) features also show small, yet reproducible, spectral differences between bovine and porcine insulin as seen in FIG. 21B. In addition, the difference spectrum shows variations in the 1341 $cm^{-1}$ and 1450 $cm^{-1}$ regions that represent the CH and $CH_2$ deformation modes, respectively. The degree of spectral difference between the insulin variants is roughly correlated with the corresponding chemical difference. In particular, the human and porcine insulins, which are the most similar chemically, also have the most similar NSD spectra, as shown in FIG. 21C, while the human and bovine insulins, which are the most chemically different, also have the most different NSD spectra, as can be seen in FIG. 21A.

Figure 22:
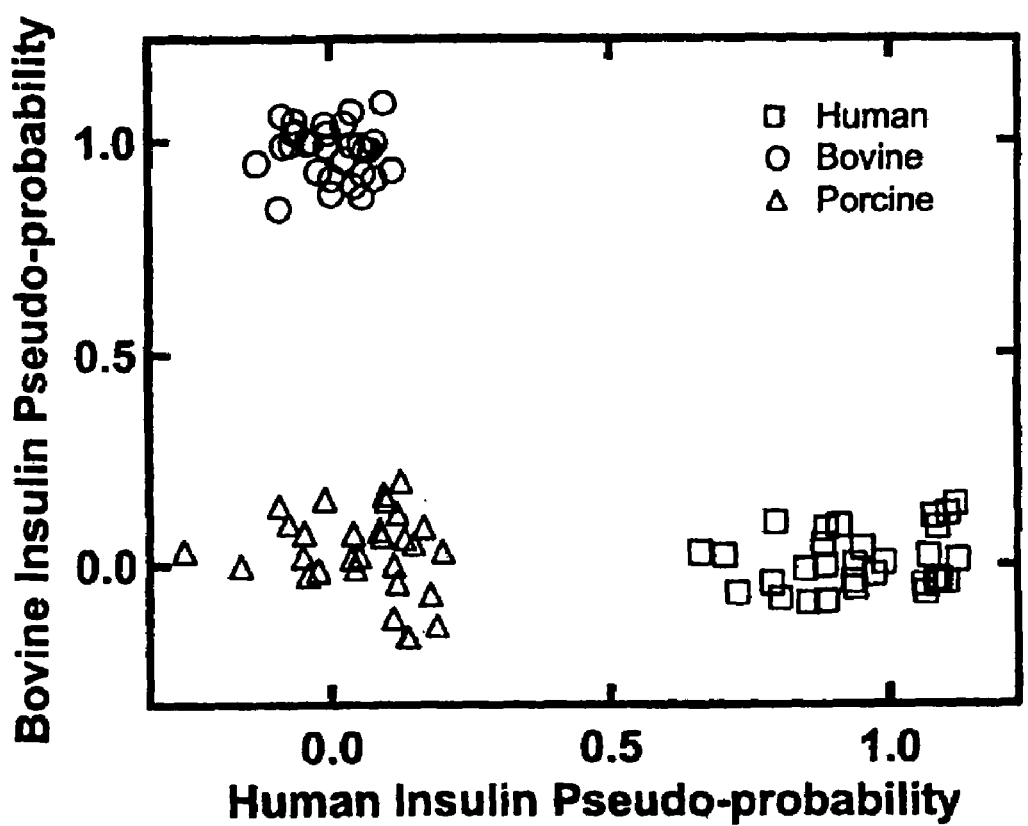
FIG. 22 is a psuedo-probability score plot for the classification of the three insulin variants.

For classification purposes, 30 spectra were taken from each variant (at two different concentrations), and each spectrum was pre-processed to produce the corresponding NSD spectrum. These pre-processed spectra were used to train and test a PLS classification algorithm. The leave-oneout (LOO) method was used for training and testing. In particular, 89 spectra were used for training and 1 for testing, the spectrum used for testing was never included in the spectra used to train the PLS algorithm. This training/testing process was repeated for all 90 spectra of the three insulin variants. The classification results demonstrate the ability to identify all three variants with no misidentification errors. FIG. 22 shows the corresponding PLS score plots indicating good separation of the spectra of the three insulin variants. Each point in this figure represents a score derived from a different spectrum, using independent PLS leave-one-out training and testing, as described above. The fact that the points cluster into three well-separated groups, corresponding to the three insulin isomers, provides a clear indication that the classification is very robust and accurate.

The Raman signal methods of the present invention can be used to analyze proteins, peptides, nucleotides and other molecules derived directly from chromatographic fractions without first lyophilizing and re-dissolving at higher concentration. Solutions of human and bovine insulin, with an initial concentration of 2 μg/μL, were first purified using RPHPLC as previously described. The retention times of the two insulin variants were 28.06 minutes for bovine and 27.91 minutes for human insulin. The concentrations of the solutions were measured by UV. The final concentrations, after RPHPLC, of bovine and human insulin were determined to be $3.0 \times 10^{-6}$ M and $2.1 \times 10^{-5}$ M, respectively.

Figure 23:
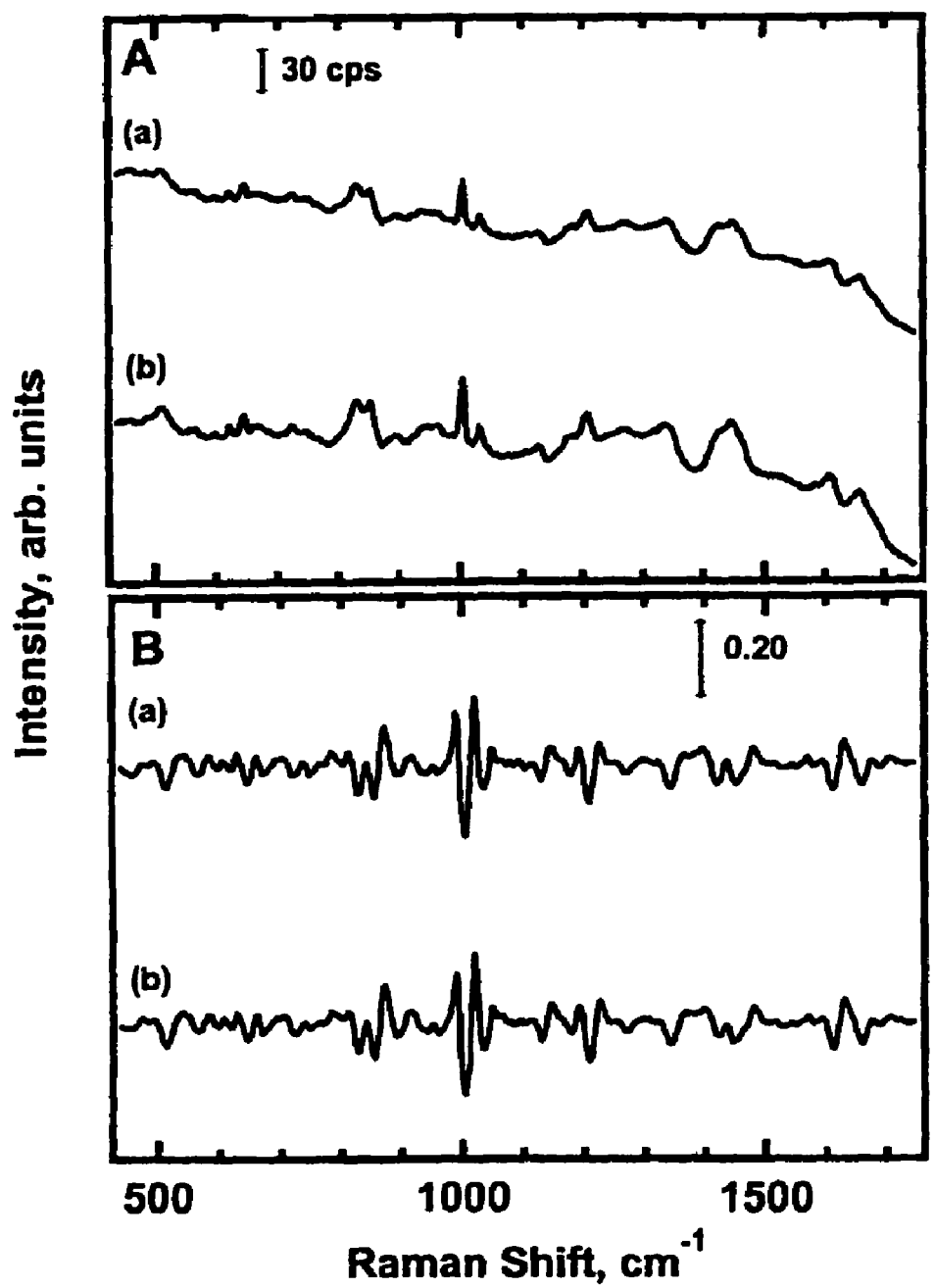
FIG. 23A is a graph of Raman spectra obtained from RPHPLC eluent fractions containing (a) bovine and (b) human insulin.
FIG. 23B is a graph of the spectra obtained from RPHPLC eluent fractions shown in FIG. 23A for the (a) bovine and (b) human insulin.

After chromatographic separation and without further preparation, the eluent of each variant was deposited on a PTFE coated stainless steel substrate for Raman spectral measurement. The resulting Raman spectra of both human and bovine insulin are displayed in FIG. 23. Due to the low concentrations of each sample, the signal-to-noise ratio of the raw Raman spectra is somewhat poorer than that obtained from higher concentration solutions. However, after NSD pre-processing, the background is suppressed and the signal-to-noise of the low concentration samples improves so that the resulting NSD spectra look very similar to those from higher concentration solutions as can be seen by comparing FIGS. 19B, 20B and 23B. Preliminary classification results produced one misclassification out of forty spectra when analyzing normal Raman spectra derived from these lower concentration solutions, which is remarkable accuracy given the clearly higher noise of the lower concentration NSD spectra.

EXAMPLE SET E

For this set of examples, two glycan isomers, 6'-N-Acetylneuraminyl-D-lactose sodium salt (6-NADL) and 3'-N-Acetylneuraminyl-D-lactose sodium salt (3-NADL), were provided by Dr. Novotny from Indiana University. Bovine insulin, human insulin and lysozyme were purchased from Sigma, and subsequently purified by RPHPLC in an acetonitrile/water elution solvent (with a 48:52 acetonitrile: water volume fraction). All other solutions were dissolved in ultrapure water (18.2MΩ) obtained using a Millpore MilliQ Plus system. A quartz substrate was purchased from Chemglass. Inc., both gold and silver foils were obtained from Sigma. Stainless steel (552768/14574 430 SS insert) and commercial Anchorchip sample supports were obtained from Bruker. The stainless steel was polished sequentially with alumina of particle sizes of 3 μm, 1 μm and 0.3 μm (Buehler). Silver and gold-coated glass sample supports were produced by sequentially evaporating 20 nm Cr and 20 nm Au or Ag onto a glass cover slip with a thermal deposition at $<10^{-5}$ torr pressure with a Turbo vacuum evaporator (Fullam, EFFA). The deposition speed was 0.1 nm/second as monitored with a Cressington thickness monitor (MEM 10) equipped with a FTM-2 crystal (TED PELLA Inc.). Prior to coating, the glass cover slip was sonicated in 10% ethanolamine for 30 minutes. Self-assembled monolayer (SAM) on gold-coated glass sample supports were prepared by dipping gold-coated glass into 1 mM hexadecanethiol solution in ethanol for 24 hours. Thin PTFE coatings (either on stainless steel or gold-coated glass) were produced by spin-coating (Model P6708, Cookson Electronics) Teflon AF® resin (Dupont) onto the substrates. The thickness of the resulting PTFE coating is about 50 nm as determined by atomic force microscopy (AFM) (Nanoscope IIIa, Digital Instruments/VEECO).

Manual deposits of specimens on the supports were performed using micropipettes to deposit 1-10 μl volumes and form spots of 0.5-5 mm diameter. The width of the protein ring produced after solvent evaporation scaled roughly with protein concentration, with rings of 10 μm-150 μm width produced when depositing solutions of 1 μM-100 μM concentration and 10 μl volume. Micro-printing of protein spots was performed using a micro-dispenser system (Model MD-K-130, Microdrop GmbH) with protein solutions of 3 μM concentration. The resulting spots of about 15-50 μm diameter were produced at about 150 μm separation by 40 co-depositions of 0.2 nl fluid volumes, for a total volume of 8 nl deposited on a single spot. Raman measurements on the micro-printed spots were performed after a drying period of about 2 minutes and occasionally thereafter during periods as long as several weeks.

Normal Raman spectra were acquired using a custom-built micro-Raman system similar to that described previously. The Raman excitation source used in this example set is a He—Ne laser (632.8 nm), with about 12 mW power focused to approximately a 2 μm diameter spot on the sample using an 80× microscope objective (Olympus MDplan 80). Back-scattered light was collected using the same objective, collimated, holographically filtered (Kaiser, Super-Notch Plus) and then imaged (using a 43 mm focal length achromat) onto the 75 μm entrance slit of an ISA HR320 (0.32 m) monochromator, equipped with an 1800 gr/mm grating and a Princeton Instruments LN/CCD-1152E CCD detector. Signal integration times of 50 seconds to 1000 seconds were used for all Raman measurements.

Figure 24:
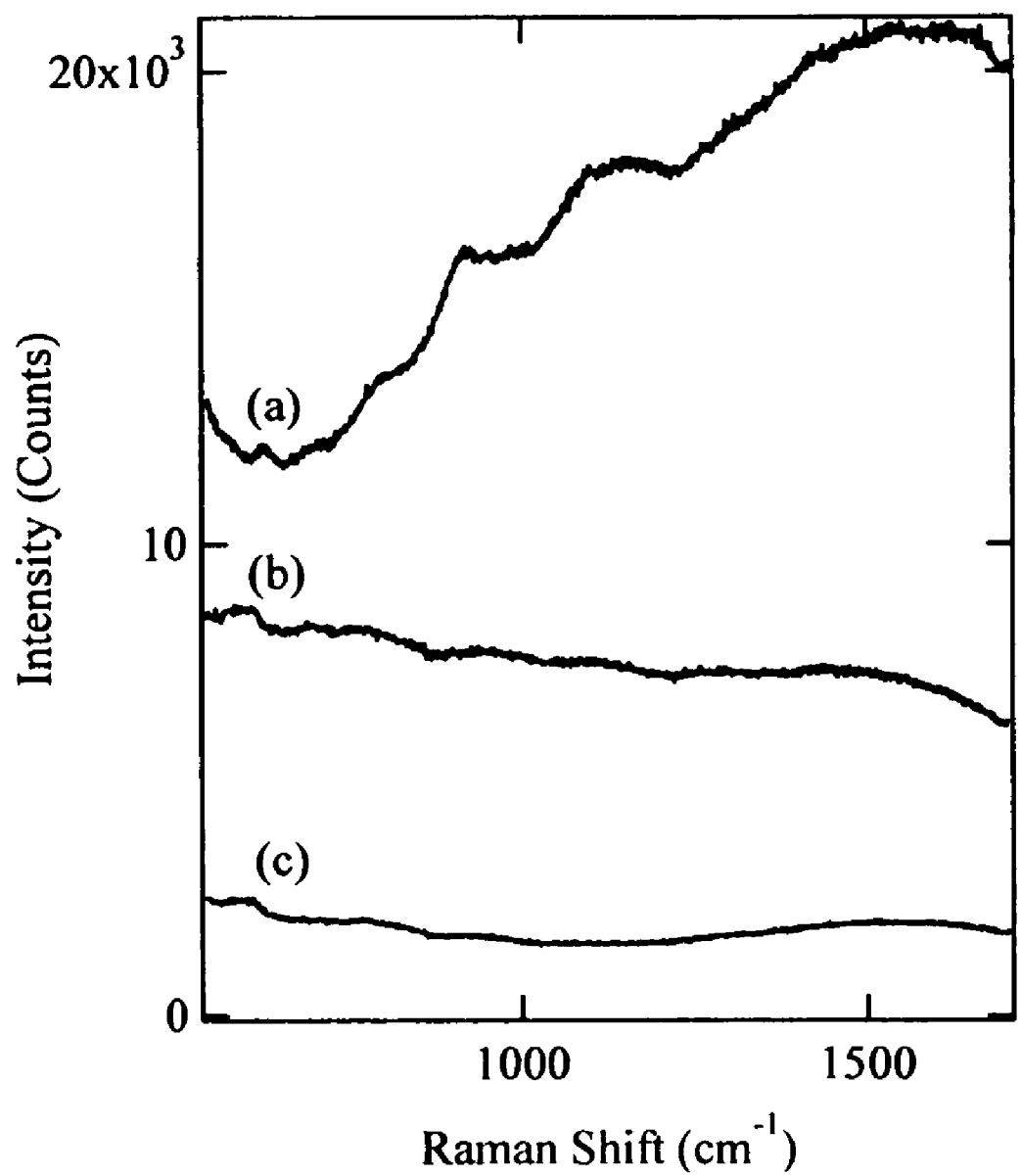
FIG. 24 is a graph of the background spectra from a glass cover slip before (a) and after (b) coating with 20 nm of gold, and from stainless steel coated with about 50 nm of PTFE (c). The integration time for all spectra is 200 seconds with a laser power of 12 mW.

FIG. 24 shows background spectra obtained from several different uncoated (blank) substrates: glass cover slip before (a) and after (b) coating with 20 nm of gold, and stainless steel coated with approximately 50 nm of PTFE (c). All the background spectra were taken with an integration time of 200 seconds and a laser power of 12 mW. It is evident that the glass cover slip (a) yields the highest background, and thus is less useful for the detection of small quantities of analyte using the methods of the present invention. The glass background, however, is markedly reduced after gold coating (b). The background of the gold foil, the SAM over gold-coated glass is essentially the same as that of the gold-coated glass, since hexadecanethiol monolayer is too thin to produce a detectable Raman signal. The same is true for the approximately 50 nm PTFE coating on stainless steel, which also produces no additional background (as has been observed with other polymers), while thicker PTFE coatings (>1 μm thick) produce Raman features with prominent peaks around 1381 $cm^{-1}$ and 733 $cm^{-1}$.

When sample solutions of the same volume are deposited on different sample supports, the diameter of the droplet on the surface depends on the degree of affinity (wetting) between the solution and the sample support. Table 4 lists the average initial (before drying) spot sizes produced when depositing 10 μL volumes of either $H_2O$, acetonitrile/water (48:52 v/v, HPLC solvent) or methanol onto quartz, PTFE-coated stainless steel, and SAM-coated gold. It will be noted that the smallest spot sizes are very close to the theoretical limit expected on a non-wetting sample support if the initially deposited drop has the shape of a half sphere, which corresponds to an attack angle of about 90°, in which case a 10 μl volume should produce a spot diameter of 3.4 mm.

TABLE 4

| Sample support | Average spot diameter (mm) produced when depositing 10 μl of solvent. | | |
|---|---|---|---|
| | Solvent | | |
| | Water | Acetonitrile/Water[a] | Methanol |
| Quartz | 4 | 5 | >10[b] |
| PTFE-SS | 3 | 3 | 5 |
| SAM-Au | 3 | 3 | 5 |

[a]HPLC solvent with 48:52 volume ratio.
[b]Spots of greater than 10 mm were also produced when depositing a 5 μl volume.

A suitable sample support should be resistant to chemical and thermal degradation. No evidence of damage to either the sample supports or the deposited analytes was observed when using SAM over gold-coated glass, and PTFE coated gold or stainless steel substrates. The only evidence for possible chemical degradation on any of the sample supports was observed with glycans (6-NADL and 3-NADL) deposited onto a silver foil sample support, whose Raman spectra were found to change with time. As discussed below, laser power dependent studies reveal no evidence for optical/thermal damage of either the analytes or sample supports used in this example set.

Figure 25:
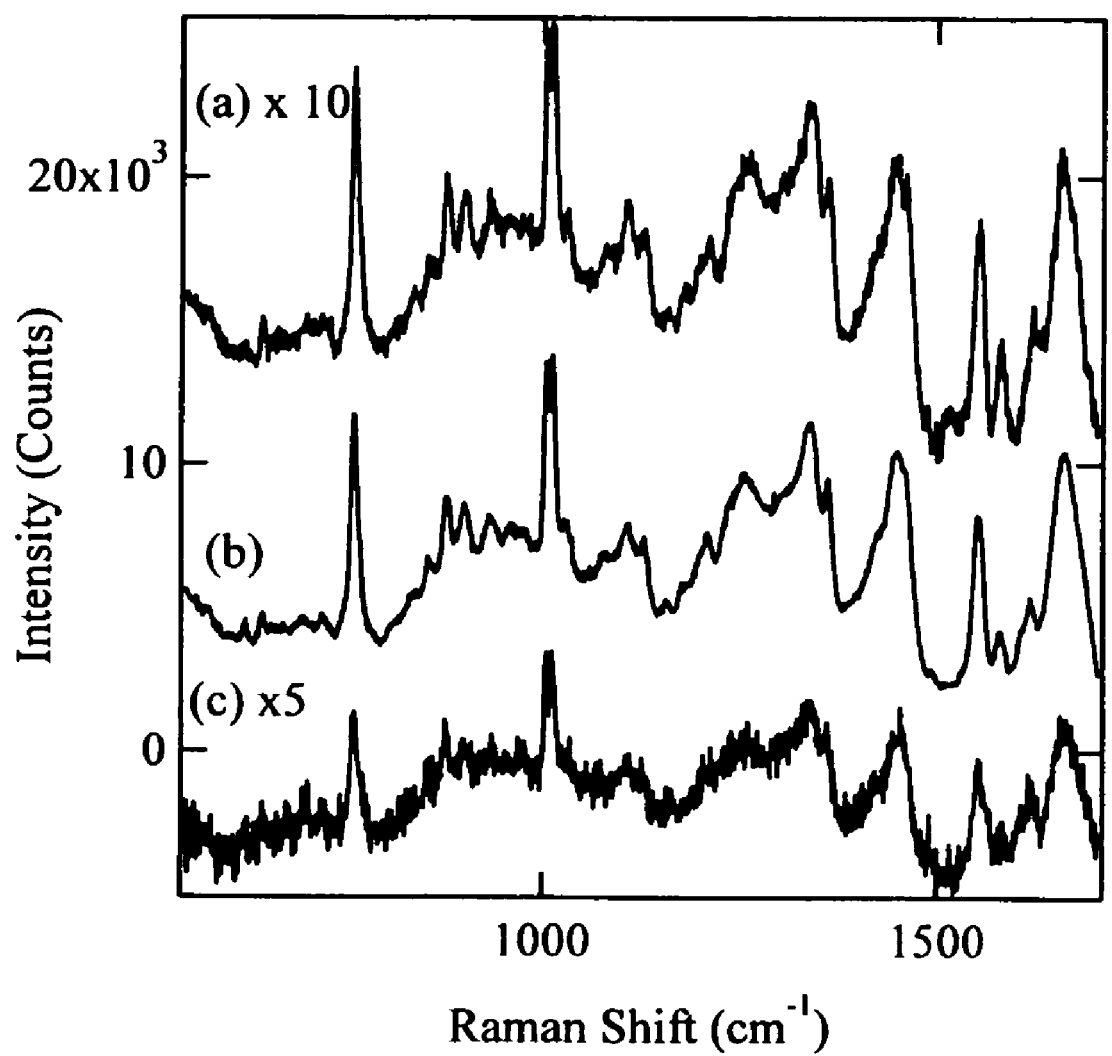
FIG. 25 is a graph of normal Raman spectra obtained after depositing lysozyme aqueous solutions on a PTFE-over-gold-coated glass substrate: (a) 2 µl, 100 µM deposit probed with a laser power of 0.3 mW and integration time of 600 seconds; (b) 2 µl, 100 µM deposit probed with a laser power of 12 mW and integration time of 100 seconds; (c) 8 nl, 3 µM deposit produced by ink-jet micro-printing using 40 co-additions with a total of 25 fmol of lysozyme deposited in a 15 µm diameter spot, probed with a laser power of 12 mW and an integration time of 400 seconds. The spectra are shifted vertically for clarity and spectrum (a) is scaled by a factor of 10 while (c) is scaled by a factor of 5 after subtracting the substrate background spectrum shown in FIG. 24.

To investigate whether there is any optical damage under various laser power conditions, Raman spectra of lysozyme were taken under different laser powers. Spectra (a) and (b) in FIG. 25 are both derived from spots produced using 2 μl of a 100 μM aqueous solution, deposited onto a sample support comprising PTFE-over-gold-coated glass. The laser power and the integration time used to produce spectrum (a) was 0.3 mW and 600 seconds, while 12 mW and 100 seconds was used to produce spectrum (b). Careful comparison of these two spectra shows no laser heating or photochemistry induced changes in spectral shape, thus indicating that 12 mW (which is about $4\times10^5$ W/cm$^2$) is below the optical damage threshold of this sample. The same laser intensity invariance was found in samples of insulin despite previous studies that suggested thermal denaturation of insulin would produce clearly visible Raman spectral changes, particularly in the 1200 cm$^{-1}$ to 1300 cm$^{-1}$ spectral region. The long-term stability of the insulin spots was investigated by acquiring Raman spectra, not shown here, after storing the sample for various periods of time in a refrigerator near 0° C. No visible variation of the insulin spectral features were observed after more than 3 weeks of cold storage and heating back up to room temperature. A comparison of our spectra with previous Raman spectra attributed to the native and denatured states of insulin, suggests that the insulin in the spots remains in its native conformation both immediately after deposition and after prolonged storage.

The spectrum (c) in FIG. 25 shows the spectral results obtained from the deposition of a total of about 25 fmol of lysozyme from a 3 μM solution using 40 micro-printing co-additions each of 0.2 nl volume. The strength of the Raman scattering from the micro-printed lysozyme is of the order of 10-100 times smaller than that from the deposits that produced the spectra (a) and (b) in FIG. 26, suggesting that the micro-printed protein deposit is at least 10 times thinner. Since the intensity of a normal Raman spectrum is proportional to the surface density of the analyte on the substrate for a given laser power, it is desirable to confine of the deposited sample to the smallest possible area so as to maximize the Raman signal to-noise ratio. A confocal micro-Raman system can achieve lateral and depth resolution of the order of 1 μm. Such as small collection volume is estimated to contain less than 0.1 fmol of deposited protein (less than 1 pg of a 10,000 Dalton protein), which may be taken as an estimate of the protein detection limit that could theoretically be achieved if all the protein of interest were deposited in a volume of a few μm$^3$. This theoretical detection limit is very close to the amount of micro-printed lysozyme that produced the spectrum in FIG. 25 (c), since only about 1/40 of the 25 fmol deposited in a 15 μm diameter spot was contained in the 2 μm diameter laser irradiated area. Furthermore, since the 20 mW laser power used is below the optical damage threshold of the deposited protein and glycan samples, there is room for further improvement in throughput and/or signal-to-noise using higher laser powers.

Figure 27:
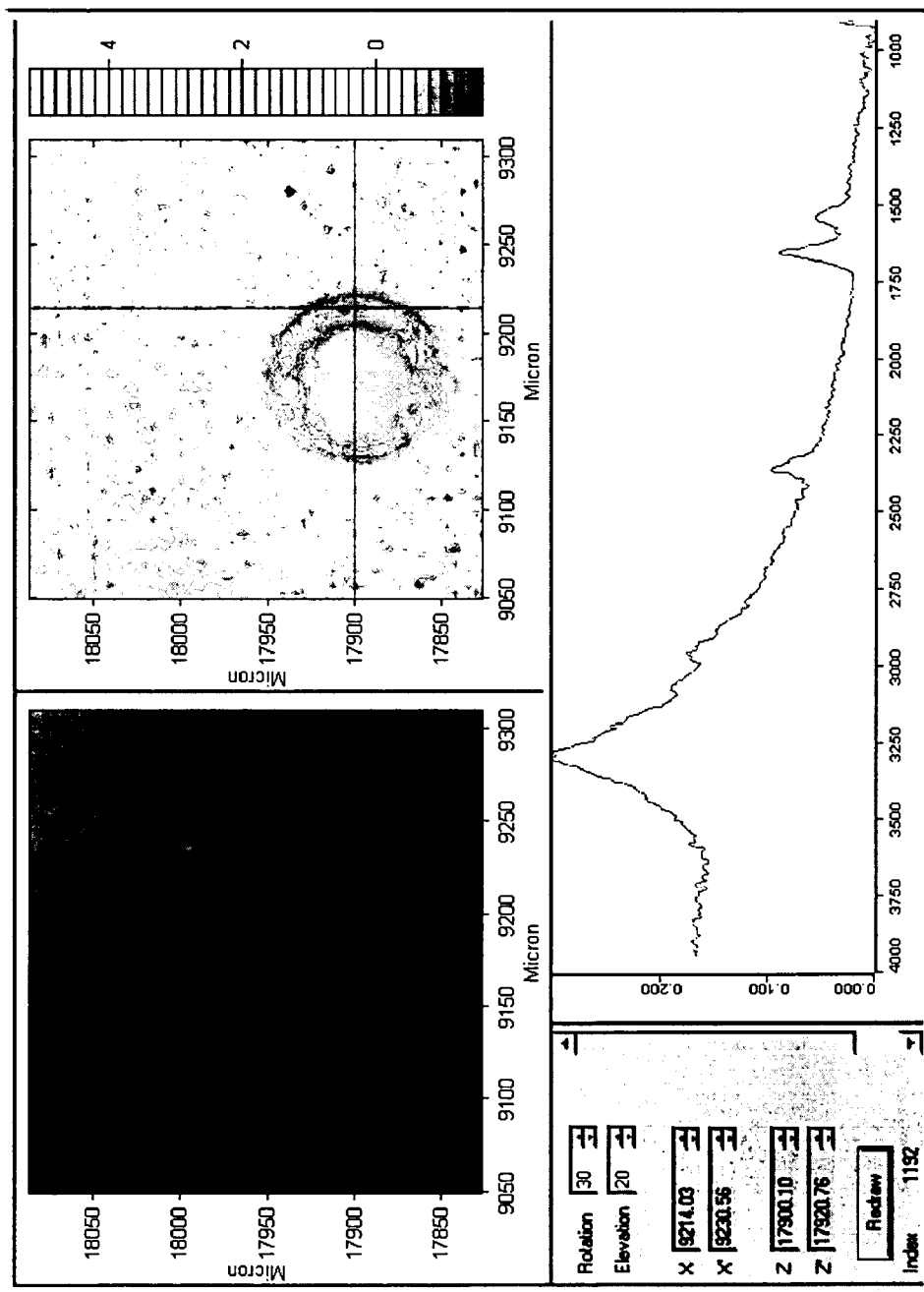
FIG. 27A is a white light image of the ring from which the spectrum shown in FIG. 26B was taken.
FIG. 27B is a FTIR "false color" image of the same ring shown in FIG. 27A with the "hot spot" in the ring overlaid by aiming cross-hairs.

In view of the low strength of the normal Raman signal from samples having low surface density of the analyte of interest, it is desirable to identify "hot spots" of sufficient surface density to provide reliable spectra. This can be accomplished by IR reflective or refractive microscopy to locate potential areas of high surface density. FTIR can then be employed to obtain a spectral scan of any located potential area followed by the collection of a normal Raman spectra to confirm the identity of the species forming the high surface density deposit. FIG. 26A is an about 200 μm×400 μm visible light image of a small section of a 64×64 spot array of micro-printed spots of about 50 μm diameter spaced from each other by about 150 μm. Each spot is estimated to contain only about 20 fmol of lysozyme, recognizably deposited in a "coffee ring" structure. If the lysozyme is uniformly deposited around the ring, then the surface density of the deposit is below the theoretical detection limit identified above. Despite this low average surface density the normal Raman spectra shown in FIG. 26 B was obtained from a point on one of the rings of the array. FIG. 27 A is a visible light image of the ring deposit from which the spectrum shown in FIG. 26 B was taken. This ring deposit was initially imaged with the aid of a FTIR "false color" (4096 cm$^{-1}$) image shown in FIG. 27 B, which shows a small area of high surface density located at the intersection of the cross-hairs. This scan for points of high surface density can be quickly performed, and a spectral scan conducted of any point that appears to be of possible interest. A FTIR spectral scan of this point, shown in FIG. 27 C has prominent peaks indicating the presence of a protein. FTIR spectral scans cannot be relied on to uniquely identify the proteins that might be present in a given specimen, although FTIR does provide additional information that can be useful in proteomics generally.

FIG. 28 A shows FTIR spectral scan of four points within the "hot spot" identified in FIG. 27 B, the spectra being off-set vertically with respect to each other to enhance visibility. It is to be noted that the wavelength axis in FIG. 28A is reversed from that shown in FIG. 27 C. All the spectra in FIG. 28 A again indicate the presence of a protein and the fine structure of the four spectra suggests that the "hot spot"

is a deposit of the same protein throughout. FIG. 28 B shows the normal Raman spectra collected from the same four points within the "hot spot", the spectra again being vertically off-set to enhance visibility. The four spectra show some intensity differences, but in each instance reflect the recognizable spectrum for lysozyme. It is important to realize that the information provided by the normal Raman spectra is quite different from the information provided by FTIR. This is visibly demonstrated by considering FIGS. 29 A and B which show four FTIR and Raman spectra, respectively, taken from micro-printed ring deposits of carbamazepine formed in a manner substantially identical to the ring deposits shown in FIG. 26 A. The normal Raman shift spectra for the four points show some amplitude variation but retain most if not all the spectral shape to be expected from carbamazepine. The FTIR absorbance spectra, on the other hand, show such dramatic differences that render interpretation of the spectra difficult. Other proteomic evaluative tools can be used in addition to FTIR and normal on a single specimen deposited on supports of the present invention.

Figure 30:
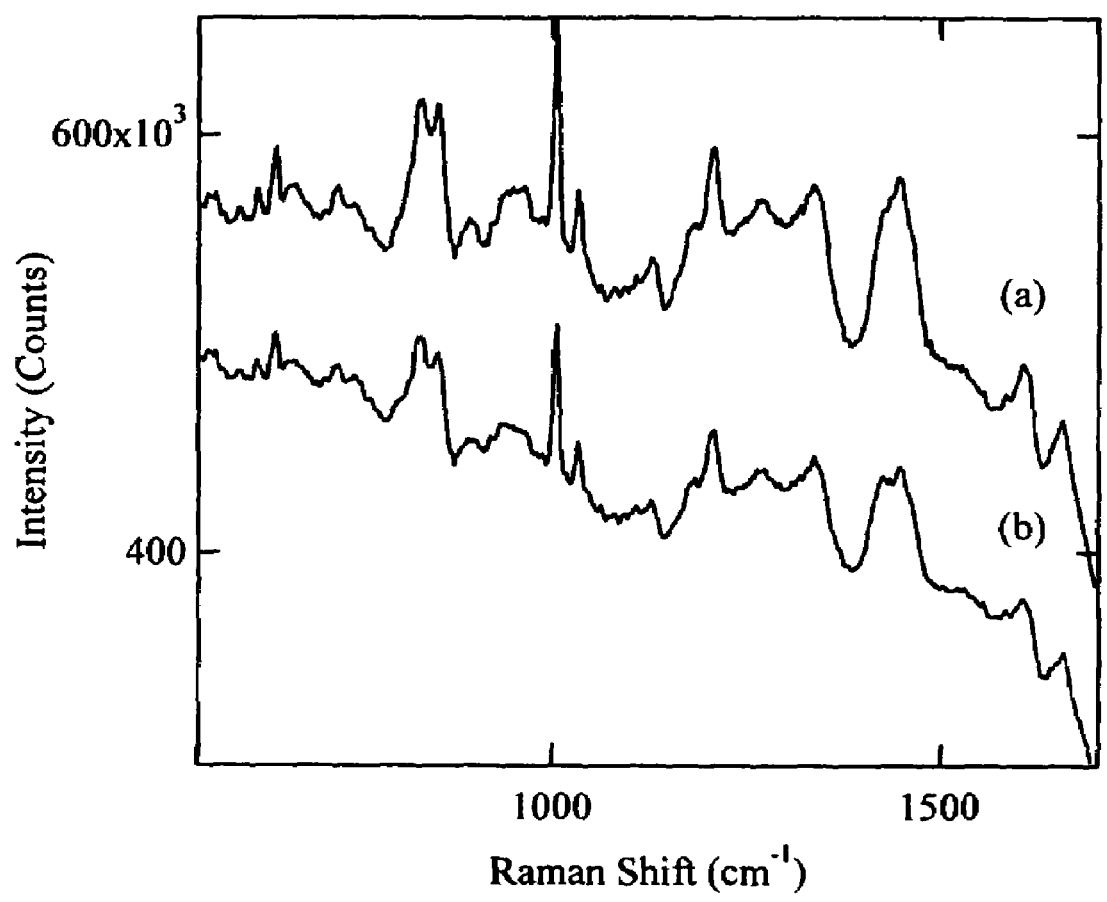
FIG. 30 is a normal Raman spectra derived from 10 µl of (a) 21 µM human insulin and (b) 3 µM bovine insulin, each derived from an HPLC fraction in acetonitrile/water with a 48:52 volume ratio, and using and integration time is 1000 seconds.

FIG. 30 shows normal Raman spectra for HPLC-purified human (a) and bovine (b) insulin obtained following deposition of 10 μL of their respected HPLC fractions onto the PTFE-coated stainless steel substrate with an integration time of 1000 seconds. The concentrations of these samples as determined by UV-VIS absorbance are 21 μM and 3 μM, respectively. Following the acquisition of the normal Raman spectra, MALDI-TOF spectra were obtained using a Brucker Reflex™ III instrument in linear mode, with 100 accumulated acquisitions, an acceleration voltage of 25 kV and a Nitrogen desorption laser of 337 nm wavelength. The MALDI matrix solution contained 10 mg/ml of 3,5-Dimethoxy-4-hydroxycinnamic acid in a mixture of solvent (50:50:0.1 water/actonitrile/trifluoroacetic acid). The sample support used for sequential normal Raman and MS spectral acquisition is PTFE-coated stainless steel. After deposition and normal Raman spectral measurement a 2 μl volume of the matrix solution was deposited over the top of the spot and MALDI-TOF spectra were recorded after the matrix solution visually dried.

Figure 31:
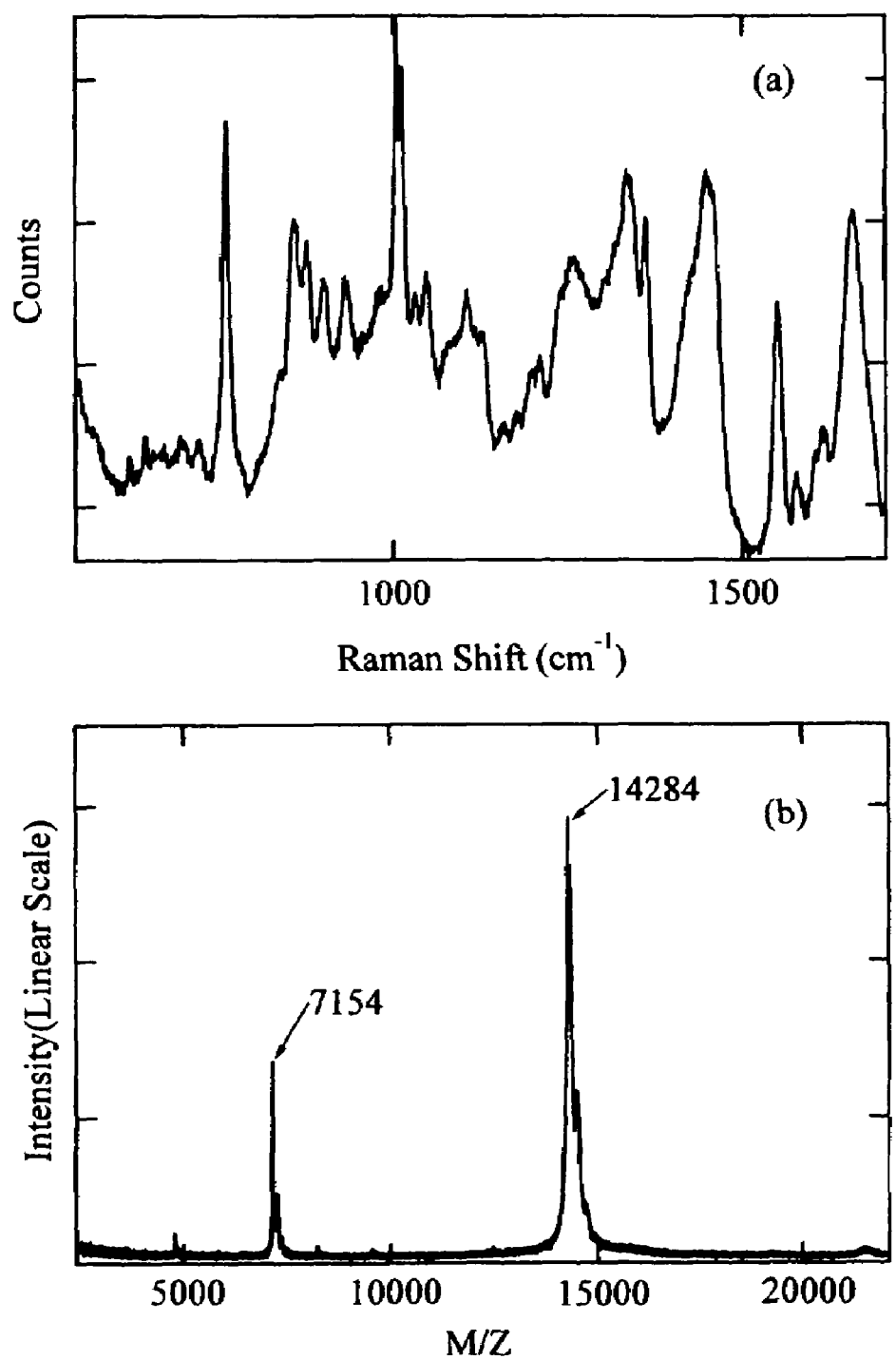
FIG. 31 are graphs of a normal Raman spectrum (a) and MALDI-TOF spectrum (b) obtained sequentially on the same deposit of 2 µl of 1 µM lysozyme solution. The integration time for spectrum (a) is 200 seconds with laser power of 12 mW. The MALDI-TOF spectrum is the sum of 100 accumulative acquisitions.

The normal Raman and MALDI-TOF spectra shown in FIG. 31 were collected from the same protein spot on a sample support of PTFE-coated stainless steel, with 2 μl, 1 μM of an aqueous lysozyme deposited. The normal Raman spectrum (upper panel) was obtained with the acquisition time of 100 seconds with a laser power of 12 mW. The spectrum (b) in the lower panel is the MALDI-TOF spectrum obtained after adding 2 μl of matrix solution. The two major peaks in the MALDI-TOF spectrum correspond to singly charged (M/Z 14284) and doubly charged (M/Z 7154) lysozyme ions. The MALDI-TOF spectrum was obtained without optimizing the experimental parameters for the MS spectral acquisition.

Figure 32:
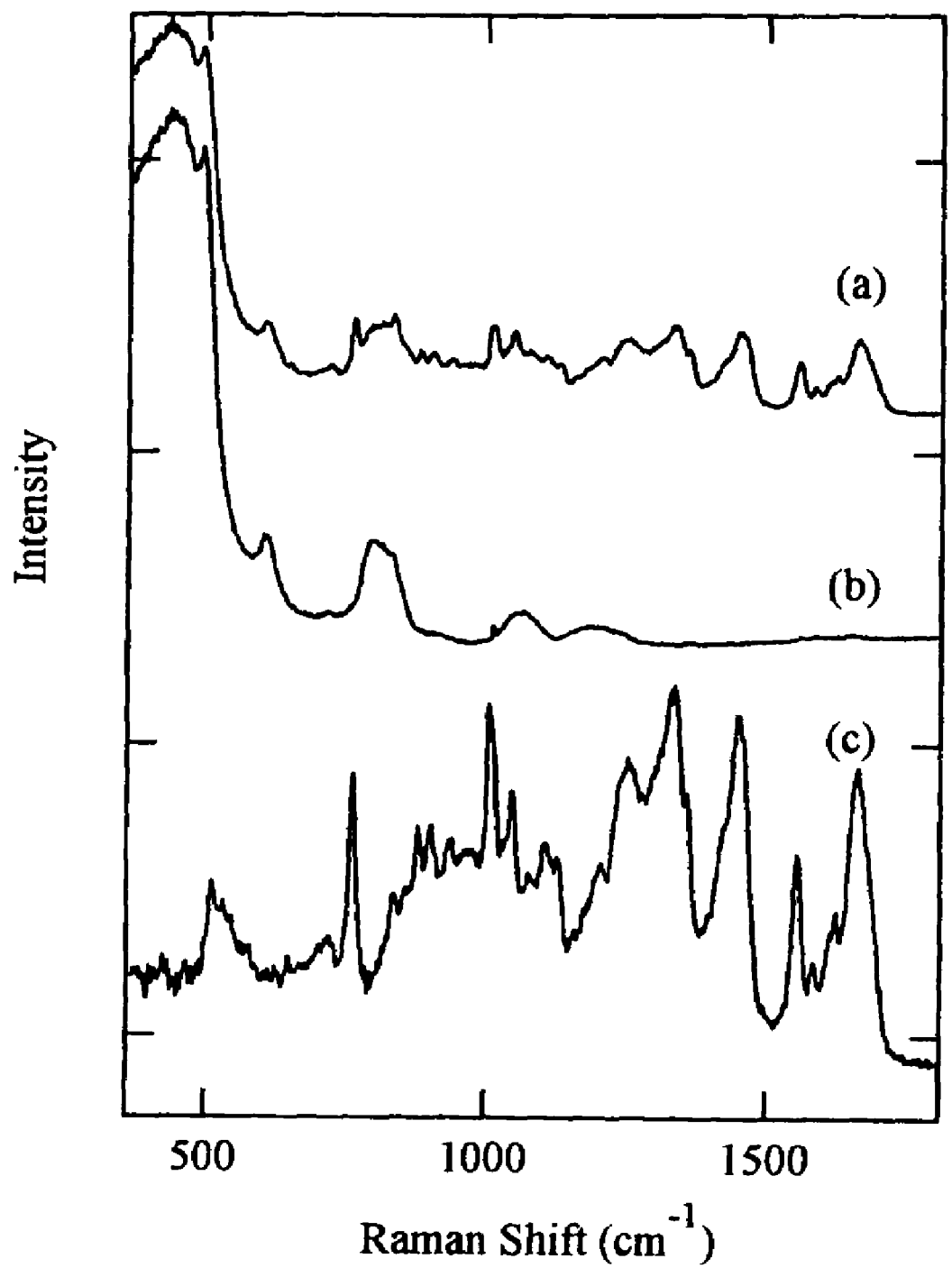
FIG. 32 are graphs taken from a deposit of lysozyme on PTFE coated quartz. Spectrum (a) is taken from a selected point on a ring deposit, spectrum (b) is taken from a region outside the ring reflecting the background for the specimen support, and spectrum (c) is the difference between spectra (a) and (b).

The normal Raman spectra of these HPLC fractions could not be detected on a quartz substrate, due to the stronger wetting interaction between latter substrate and the acetonitrile/water solvent, which increased the spot size and thus reduced the deposited protein surface density. Quartz can be used as a substrate for form a specimen support of the present invention that can be used in transmission as well as in reflection. FIG. 32 shows spectra shown here were obtained by depositing 5 uL of 10 uM lysozyme on a PTFE coated quartz surface, the PTFE coating being sufficiently thin and uniform as to not affect the FTIR or normal Raman spectra, either in transmission or reflection mode. Spectra (a) and (b) were acquired by focusing the excitation laser on the region with and without lysozyme respectively. Spectrum (c) is the difference between spectra (a) and (b). All the spectra were scaled and off-set for better visualization. The excitation laser is 632.8 nm, integration time of 200 s with 100× objective.

The methods of the present invention not only facilitate the measurement of Raman spectra of analytes derived from low concentration solutions, but also serve as effective methods for separating biological polymers, oligomers, and monomers including proteins, peptides, polysaccharides, glycans, nucleotides, and other molecules from other solution components including fluorescent impurities and buffers. Thus the present methods can produce much the same effect as a recrystalization or chromatographic purification processes. Both kinetics and thermodynamics may well contribute to the observed segregation.

Kinetics contributions to segregation can include the so-called "coffee ring" effect produced by convective streaming occurring during the evaporation of a liquid on solid sample support. This effect is presumed to be a significant driving force for the observed propensity of proteins, peptides, nucleotides and other larger oligomers and biological polymers to accumulate in a ring around the outer edge of the deposits achieved with the present method. The kinetics of crystallization can also contribute to segregation since compounds with a higher rate of nucleation and crystal growth would tend to deposit separately from those with lower crystallization rates.

Thermodynamics can also be expected to drive segregation since pure solids often have lower free energy than solid solutions, except perhaps when the compounds have very similar structure, or tend to deposit as amorphous solids, or in the relatively unusual circumstance that compounds of very different structure are able to efficiently co-crystallize.

The differential solubilities of various solution components may also play a role in segregation. For example, since proteins, peptides, nucleotides and larger oligomers and biological polymers are relatively insoluble they may generally fall out of solution early in the evaporation process. On the other hand, highly soluble compounds (such as buffers), or impurities present at very low initial concentration (such as fluorescent impurities), may remain dissolved in an evaporating drop far longer, and so tend to ultimately deposit somewhere inside the region encircled by the outer ring.

Although chemical segregation using the methods of the present invention should be widely applicable, the methods are certainly not expected to be universal. The methods are useful in conection with some, but not all, soluble solids. Examples in which the segregation methods of the present invention may not work include systems that do not easily crystallize, such as sugars, particularly complex carbohydrates, which tend to form viscous hydrates upon evaporation, or which may tend to retain fluorescent impurities. In addition, compounds with a strong chemical affinity for each other are not expected to segregate in accordance with the present method. For example, preliminary studies have indicated that solutions containing lysozyme (10 μM) and Rhodamine-6-G (10 nM) do not segregate upon deposition, presumably indicating a strong association between these two molecules. Such negative segregation results may in fact prove to have practical applications in screening for interactions between proteins, peptides, glycans, nucleotides, and various other compounds of environmental or pharmaceutical importance.

Normal Raman spectra collected using the methods of the present invention can be used to measure and analyze various phosphorylation states of proteins such as tyrosine kinase peptide. Thus, Raman combined with PLS can be used to accurately detect the site of phosphorylation on a peptide. Although phosphorylation of tyrosine is most easily detectable, the weaker signatures associated with serine and threonine phosphorylation are sufficiently reproducible to facilitate highly reliable spectral classification. Since the methods of the present invention are non-destructive, they can also be used in combination with MALDI-MS to reap the synergistic benefits of multi-spectral analysis.

Thus, Raman spectroscopy can be used to detect subtle differences between proteins of similar amino-acid composition. The methods of the present invention can be used to collect high quality Raman spectra from small volumes of low concentration protein solutions. A multivariate PLS classification algorithm can used reliably identify insulin variants from small differences between their Raman spectral features. Moreover, Raman spectra obtained from RPHPLC fractions demonstrate the application of the present invention as a chromatographic detection method.

The exquisite structural sensitivity demonstrated by the present results suggests that Raman spectroscopy can be used with the methods of the present invention to add a valuable dimension of information to current proteomic diagnostic methods. Raman spectroscopy contains fingerprint information that is sensitive to the chemical bonding structure of proteins, peptides and other molecule of interest, and thus can be complimentary to and used in combination with information obtained from chromatographic, other spectrographic, and mass spectral analysis. The combined use of Raman with the methods of the present invention and other analytical tools promises to facilitate the enhanced detection of subtle differences between individual proteins and/or protein-peptide mixtures, such as those associated with biomarkers for disease states as well as genetically, environmentally, or pharmaceutically induced physiological responses.

What is claimed is:

1. A method of obtaining structural characteristic information from molecular specimens present in a solvent comprising the steps of:

providing a substantially planar solvophobic sample support having optically smooth substrate with a top surface covered by a solvophobic coating, applying a droplet of a specimen-containing solvent to the sample support surface, evaporating the solvent from the droplet at a rate permitting formation of a ring-like region of enhanced specimen deposit on the sample support surface, irradiating a portion of the region of enhanced specimen deposit with a beam directed by an optical system aligned substantially normal to the sample support surface, collecting radiation from the irradiated portion, and detecting a selected spectra segment of the collected radiation.

2. The method of claim 1 wherein the providing step comprises the step of covering a metallic surface having a roughness of less than one-tenth the wavelength of the irradiating beam with the solvophobic enhancing layer to a thickness of about one-quarter the wavelength of the irradiating beam.

3. The method of claim 2 further comprising the step of forming the solvophobic enhancing layer to a thickness of between about 10 nm and about 300 nm from a fluorinated polymer, fluorinated hydrocarbon, or thiol derivative of a hydrocarbon.

4. The method of claim 3 further comprising the steps of diluting the material forming the solvophobic enhancing layer with a solvent and applying the diluted material to the metallic surface while the substrate is spinning.

5. The method of claim 1 wherein the applying step includes the step of forming the specimen-containing solvent into a droplet having a volume of between about 10 nl and about 10 μl, the specimen being present in the droplet at less than about 100 μM concentration.

6. The method of claim 5 wherein the applying step includes the steps of chromatographically concentrating the specimen to a selected fraction of a flow of liquid and depositing a droplet from the selected fraction onto the sample support surface.

7. The method of claim 6 further comprising the steps of arranging an array of droplets on the sample support surface and comparing the selected spectra segments of the droplets forming the array.

8. The method of claim 7 further comprising the step of forming the array of droplets from specimens collected from a single source at different times to provide a history of the single source.

9. The method of any of claims 5-8 comprising the step of micro printing the droplets onto the sample support surface.

10. The method of claim 1 further comprising the steps of situating the sample support within an environmental control chamber and controlling the vapor pressure of the solvent within the chamber.

11. The method of claim 1 further comprising the step of focusing the irradiating beam onto a spot having a diameter of between about 1 μm and 100 μm, and positioning the irradiating beam within about 100 μm of an edge of said specimen deposit.

12. The method of claim 1 further comprising the steps of forming the irradiating beam with an excitation laser having a output power of less than 100 mWatts and integrating the collected radiation for a time of between 5 seconds and 500 seconds.

13. The method of claim 1 further comprising the steps of forming the irradiating beam with an excitation laser having an output power of between about 1 and 100 Watts and integrating the collected radiation for a time of between about 0.01 and 1 seconds.

14. The method of claim 12 or 13 further comprising the step of collecting the collected radiation back through a portion of the optical system delivering the excitation laser output.

15. The method of claim 14 further comprising the step of processing the detected spectra using a Savistky-Golay second derivative algorithm.

16. The method of claim 14 further comprising the step of classifying the processed spectra with a partial least square discriminant program.

17. The method of claim 16 further comprising the step of plotting the classified spectra as a pseudo probability.

18. The method of claim 15 further comprising the step of normalizing the output of the second derivative algorithm.

19. The method of claim 18 further comprising the step of subtracting the normalized spectral outputs of two specimens to detect any spectral differences.

20. The method of claim 1 wherein the detecting step comprises the steps of analyzing the collected radiation in the IR range followed by analyzing the normal Raman spectra from an identical irradiated portion of the specimen.

21. The method of claim 20 further comprising the step of subjecting the identical irradiated portion of the specimen to a MALDI TOF MS evaluation.

22. A molecular sample support to facilitate exposure of a specimen present in a solvent to radiation of a selected wavelength, the holder comprising a substantially planar substrate, a surface on the substrate having a roughness of less than about one-tenth the wavelength of the radiation, and a solvophobic enhancement layer of less than about one-quarter the wavelength of the radiation covering the substrate surface.

23. The molecular sample support of claim 22 wherein the solvophobic enhancement layer consists essentially of a fluorinated polymer, a fluorinated hydrocarbon, or a thiol derivative of a hydrocarbon.

24. The molecular sample support of claim 22 wherein the solvophobic enhancement layer consists essentially of polytetrafluoroethylene deposited on the substrate while the substrate is spinning.

25. The molecular sample support of claim 22 wherein the substrate comprises a layer of metal selected from gold, stainless steel, silver, platinum, titanium, and aluminum, and alloys of these metals.

26. The molecular sample support of claim 25 further comprising a glass surface supporting the layer of metal.

27. The molecular sample support of claim 22 wherein the substrate comprises a layer of quartz, germanium, galium arsenide, or zinc sulfide.

28. The molecular sample support of claim 22 wherein the substrate comprises a layer of a polymeric material selected from polyethylene, polypropylene, polycarbonate, polyacrylate, polymethacrylate, and polystyrene.

29. A method of reducing interference in Raman spectra taken from a specimen containing an analyte and a contaminant comprising the steps of:
forming a solution of the specimen in a solvent,
providing a substantially planar solvophobic sample support having optically smooth substrate with a top surface covered by a solvophobic coating,
applying a droplet of a specimen-containing solvent to the sample support surface,
evaporating the solvent from the droplet at a rate permitting formation of a ring-like region of enhanced specimen deposit on the sample support surface,
irradiating a portion of the region of enhanced specimen deposit with a beam directed by an optical system aligned substantially normal to the sample support surface,
collecting radiation from the irradiated portion, and
detecting a selected spectral segment of the collected radiation.

30. The method of claim 29 wherein the contaminant is one generating fluorescence interference and the method further comprises the step of photo-bleaching the portion of the region of enhanced specimen deposit by pre-exposing the portion of the region to a beam from a Raman excitation laser.

31. The method of claim 29 wherein the contaminant is a buffer and the collecting step is from a portion of the ring-like region so as to minimize the spectral interference of the buffer.

32. The method of claim 1 or 29 further comprising the step of comparing the detected spectral segment to other similarly acquired spectral segments of known compositions.

33. The method of claim 32 wherein the comparing step includes the steps of calculating the second derivative of each spectral curve, and classifying the derivative curves into clusters of similar specimen composition.

34. The method of claim 32 wherein the comparing step includes assigning commonly observed spectral features to known structural features of the known compositions and looking for such commonly observed spectral features in spectra of at least partially unknown compositions to detect physiological or conformational structure similarities therein.

35. The method of claim 34 further comprising the step of quantifing the fractional portion of the sample population exhibiting a given physiological or conformational structure.

36. A method of obtaining structural characteristic information from molecular specimens present in a solvent comprising the steps of:
   providing a substantially planar solvophobic sample support having optically smooth substrate with a top surface covered by a solvophobic coating,
   micro-printing an array of droplets of a specimen-containing solvent to the sample support surface,
   evaporating the solvent from each droplet at a rate permitting formation of a ring-like region of enhanced specimen deposit on the sample support surface at each droplet location,
   scanning the ring-like regions to locate hot spots of significant specimen deposit, and
   collecting radiation from the hot spots to detect a selected spectra segment of the collected radiation.

37. The method of claim 36 wherein the scanning step is performed using FTIR.

38. The method of claim 37 wherein the radiation collected is Raman scattering.

39. The method of claim 36 wherein the micro-printing step is repeated to co-deposit additional droplets on each ring-like deposit in the array.

40. The method of claim 39 wherein the evaporating step is repeated after each repetition of the micro-printing step.

* * * * *